US012797388B2

(12) United States Patent
Waldman

(10) Patent No.: US 12,797,388 B2
(45) Date of Patent: Nov. 17, 2026

(54) COMPOSITIONS AND METHODS OF USE FOR MODIFIED RELEASE MINOXIDIL

(71) Applicant: Veradermics, Incorporated, New Haven, CT (US)

(72) Inventor: Reid Waldman, West Hartford, CT (US)

(73) Assignee: Veradermics, Incorporated, New Haven, CT (US)

( * ) Notice: Subject to any disclaimer, the term of this patent is extended or adjusted under 35 U.S.C. 154(b) by 0 days.

(21) Appl. No.: 19/315,441

(22) Filed: Aug. 29, 2025

(65) Prior Publication Data

US 2025/0387394 A1 Dec. 25, 2025

Related U.S. Application Data

(63) Continuation of application No. 19/094,703, filed on Mar. 28, 2025, which is a continuation of application No. 18/437,724, filed on Feb. 9, 2024, now Pat. No. 12,268,688, which is a continuation of application No. PCT/US2023/035920, filed on Oct. 25, 2023.

(60) Provisional application No. 63/433,203, filed on Dec. 16, 2022, provisional application No. 63/419,155, filed on Oct. 25, 2022.

(51) Int. Cl.

| | |
|---|---|
| ***A61K 31/506*** | (2006.01) |
| ***A61K 9/00*** | (2006.01) |
| ***A61K 9/20*** | (2006.01) |
| ***A61K 9/28*** | (2006.01) |
| ***A61P 17/14*** | (2006.01) |

(52) U.S. Cl.

CPC .......... *A61K 31/506* (2013.01); *A61K 9/0053* (2013.01); *A61K 9/2013* (2013.01); *A61K 9/2018* (2013.01); *A61K 9/2054* (2013.01); *A61K 9/28* (2013.01); *A61P 17/14* (2018.01)

(58) Field of Classification Search

CPC .................................................... A61K 31/506
USPC ......................................................... 514/275
See application file for complete search history.

(56) References Cited

U.S. PATENT DOCUMENTS

| | | | |
|---|---|---|---|
| 6,383,471 | B1 | 5/2002 | Chen et al. |
| 6,448,323 | B1 | 9/2002 | Jordan |
| 6,485,950 | B1 | 11/2002 | Kumar et al. |
| 6,849,661 | B2 | 2/2005 | Kelly et al. |
| 7,037,697 | B2 | 5/2006 | Kumar et al. |
| 7,749,533 | B2 | 7/2010 | Fu et al. |
| 7,776,844 | B2 | 8/2010 | Yu et al. |
| 7,871,643 | B2 | 1/2011 | Lizio et al. |
| 7,915,247 | B1 | 3/2011 | Arnold et al. |
| 8,173,161 | B2 | 5/2012 | Bunick et al. |
| 8,231,902 | B2 | 7/2012 | Solomon et al. |
| 8,263,125 | B2 | 9/2012 | Vaya et al. |
| 8,268,352 | B2 | 9/2012 | Vaya et al. |
| 8,349,297 | B2 | 1/2013 | Brown et al. |
| 8,383,155 | B2 | 2/2013 | Bar-shalom et al. |
| 8,394,409 | B2 | 3/2013 | Odidi et al. |
| 8,414,919 | B2 | 4/2013 | Gervais et al. |
| 8,529,939 | B2 | 9/2013 | Masters et al. |
| 8,591,945 | B2 | 11/2013 | Vandecruys et al. |
| 8,613,285 | B2 | 12/2013 | Fuisz |
| 8,835,376 | B2 | 9/2014 | Shen et al. |
| 8,858,993 | B2 | 10/2014 | Gold et al. |
| 8,920,834 | B2 | 12/2014 | Rahmouni et al. |
| 8,927,014 | B2 | 1/2015 | Rahmouni et al. |
| 8,962,064 | B2 | 2/2015 | Kolter et al. |
| 9,011,907 | B2 | 4/2015 | Ravishankar et al. |
| 9,023,386 | B2 | 5/2015 | Benita et al. |
| 9,029,427 | B2 | 5/2015 | Endo et al. |
| 9,060,936 | B2 | 6/2015 | Berndl et al. |
| 9,161,917 | B2 | 10/2015 | Faure et al. |
| 9,205,047 | B2 | 12/2015 | Shoichet et al. |
| 9,237,760 | B2 | 1/2016 | Ravishankar et al. |

(Continued)

FOREIGN PATENT DOCUMENTS

| | | | |
|---|---|---|---|
| AU | 2011100917 | A4 | 9/2011 |
| AU | 2011100917 | B4 | 5/2013 |

(Continued)

OTHER PUBLICATIONS

Vahabi-Amlashi et. al. "A randomized clinical trial on therapeutic effects of 0.25 mg oral minoxidil tablets on treatment of female pattern hair loss" Dermatologic Therapy, Sep. 2021, https://doi.org/10.1111/dth.15131.

Panchaprateep et al., "Efficacy and Safety of Oral Minoxidil 5 mg Once Daily in the Treatment of Male Patients with Androgenetic Alopecia: An Open-Label and Global Photographic Assessment" Dermatol Ther (Heidelb) (2020) 10:1345-1357.

Rodrigues-Barata et. al. "Low-Dose Oral Minoxidil for Female Pattern Hair Loss: A Unicenter Descriptive Study of 148 Women" Skin Appendage Disord. Feb. 21, 2020;6(3):175-176. doi: 10.1159/000505820.

(Continued)

*Primary Examiner* — Raymond J Henley, III
(74) *Attorney, Agent, or Firm* — PROCOPIO, CORY, HARGREAVES & SAVITCH LLP; Brent Johnson; "Ralph" Younghoon Kim

(57) ABSTRACT

The compositions and methods provided herein include a pharmaceutical formulation for oral administration comprising a daily dose of a modified release formulation of minoxidil or a pharmaceutically acceptable salt thereof. Also provided herein are pharmaceutical formulations for oral administration comprising a daily dose of a modified release formulation of minoxidil or a pharmaceutically acceptable salt thereof and one or more additional active agents. Also provided herein are methods of treating hair loss by administering to a subject in need thereof a daily dose of a modified release formulation of minoxidil or a pharmaceutically acceptable salt thereof. Further provided herein is a kit including a slow modified release vehicle comprising oral minoxidil or a pharmaceutically acceptable salt thereof.

19 Claims, 7 Drawing Sheets

(56) References Cited

U.S. PATENT DOCUMENTS 9,254,268 B2 2/2016 Temtsin Krayz et al.
9,283,192 B2 3/2016 Mullen et al.
9,351,940 B2 5/2016 Salman et al.
9,371,330 B2 6/2016 Kahn et al.
9,402,909 B2 8/2016 Liepold et al.
9,468,644 B2 10/2016 Kalem
9,474,719 B2 10/2016 Mullen et al.
9,554,989 B2 1/2017 Kaplan et al.
9,555,006 B2 1/2017 Petereit et al.
9,687,451 B2 6/2017 Rubino et al.
9,730,866 B2 8/2017 Hashimoto et al.
9,730,899 B2 8/2017 Bar et al.
9,750,701 B2 9/2017 Jans et al.
9,839,644 B2 12/2017 Kumar
9,974,753 B2 5/2018 Salman et al.
9,993,439 B2 6/2018 Gu et al.
10,076,500 B2 9/2018 Grenier et al.
10,092,568 B2 10/2018 Kahn et al.
10,143,626 B2 12/2018 Li
10,272,086 B2 4/2019 Hsu
10,314,787 B2 6/2019 Odidi et al.
10,500,282 B2 12/2019 Desai et al.
10,512,670 B2 12/2019 Song et al.
10,561,593 B2 2/2020 Wu
10,624,858 B2 4/2020 Odidi et al.
10,653,718 B2 5/2020 Joanny Menvielle-bourg
10,933,024 B2 3/2021 Baer et al.
11,065,205 B2 7/2021 Mullen et al.
11,116,770 B2 9/2021 Sinclair
11,147,766 B2 10/2021 Zalit et al.
11,207,511 B2 12/2021 Barman et al.
11,278,499 B2 3/2022 Li
11,285,102 B2 3/2022 Menachem et al.
11,318,088 B2 5/2022 Popov
11,318,107 B2 5/2022 Vasisht et al.
11,337,923 B2 5/2022 Yu
11,504,342 B2 11/2022 Vasisht et al.
11,547,839 B2 1/2023 Menachem et al.
11,819,576 B2 11/2023 Damm et al.
12,263,323 B2 4/2025 Barman et al.
12,268,688 B2 4/2025 Waldman
12,491,184 B2 12/2025 Waldman
2002/0035070 A1 3/2002 Gardlik et al.
2002/0119174 A1 8/2002 Gardlik et al.
2003/0064494 A1 4/2003 Kumar
2003/0091630 A1 5/2003 Louie-helm et al.
2003/0092765 A1 5/2003 Kelly et al.
2003/0124191 A1 7/2003 Besse et al.
2003/0133985 A1 7/2003 Louie-helm et al.
2003/0152622 A1 8/2003 Louie-helm et al.
2004/0063784 A1 4/2004 Kelly et al.
2004/0096499 A1 5/2004 Vaya et al.
2005/0013857 A1 1/2005 Fu et al.
2005/0118272 A1 6/2005 Besse et al.
2005/0276836 A1 12/2005 Wilson et al.
2006/0280791 A1 12/2006 Ju et al.
2007/0020331 A1 1/2007 Gold et al.
2007/0148234 A1 6/2007 Ju et al.
2007/0212416 A1 9/2007 Rubino et al.
2008/0292560 A1 11/2008 Tamarkin et al.
2009/0004281 A1 1/2009 Nghiem et al.
2009/0098200 A1 4/2009 Temtsin et al.
2009/0269684 A1 10/2009 Fu et al.
2010/0028439 A1 2/2010 Jenkins et al.
2010/0047322 A1 2/2010 Hoffman et al.
2010/0104639 A1 4/2010 Williams et al.
2010/0159001 A1 6/2010 Cardinal et al.
2010/0172993 A1 7/2010 Singh et al.
2010/0310607 A1 12/2010 Ju et al.
2010/0316678 A1 12/2010 Goodchild et al.
2011/0256239 A1 10/2011 Shapiro
2012/0171262 A1 7/2012 Ju et al.
2012/0238608 A1 9/2012 Ali et al.
2012/0301546 A1 11/2012 Hassan
2013/0004444 A1 1/2013 Baudouin
2013/0017262 A1 1/2013 Mullen et al.
2013/0022676 A1 1/2013 Mullen et al.
2013/0022677 A1 1/2013 Mullen et al.
2013/0078284 A1 3/2013 Ju et al.
2013/0203766 A1 8/2013 Mendla et al.
2013/0280233 A1 10/2013 Kahn et al.
2015/0231069 A1 8/2015 Modi
2015/0232468 A1 8/2015 Kahn et al.
2016/0067217 A1 3/2016 Kumar
2016/0213694 A1 7/2016 Kumar
2016/0220505 A1 8/2016 Temtsin Krayz et al.
2018/0042945 A1 2/2018 Kumar
2019/0269684 A1 9/2019 Sinclair
2019/0381296 A1 12/2019 Barman et al.
2020/0108008 A1 4/2020 Gan et al.
2020/0121681 A1 4/2020 Loose
2020/0214958 A1 7/2020 Goren et al.
2021/0030693 A1 2/2021 Vasisht et al.
2021/0085622 A1 3/2021 Vasisht et al.
2021/0161820 A1 6/2021 Sei et al.
2021/0186880 A1 6/2021 Mathiowitz et al.
2021/0299044 A1 9/2021 Fossel
2021/0338671 A1 11/2021 Williams et al.
2022/0047608 A1 2/2022 Dharmarajan
2022/0054425 A1 2/2022 Choi et al.
2022/0160872 A1 5/2022 Yadavalli et al.
2022/0296486 A1 9/2022 Goren et al.
2023/0181468 A1 6/2023 Di Miguel et al.
2023/0355643 A1 11/2023 Chan et al.
2024/0000746 A1 1/2024 Minakar et al.
2024/0009192 A1 1/2024 Zhang
2024/0252495 A1 8/2024 Waldman
2024/0325350 A1 10/2024 Dandiker
2024/0374594 A1* 11/2024 Sinha .................. A61K 9/0053
2025/0064807 A1 2/2025 Sinclair
2025/0073161 A1 3/2025 Sheu et al.
2025/0221993 A1 7/2025 Waldman
2025/0221994 A1 7/2025 Waldman
2025/0302835 A1 10/2025 Waldman
2025/0302836 A1 10/2025 Waldman
2025/0312346 A1 10/2025 Waldman
2025/0319082 A1 10/2025 Waldman
2025/0319083 A1 10/2025 Waldman
2025/0319085 A1 10/2025 Waldman
2025/0319086 A1 10/2025 Waldman
2025/0319087 A1 10/2025 Waldman
2025/0325546 A1 10/2025 Waldman
2025/0332108 A1 10/2025 Waldman
2025/0332109 A1 10/2025 Waldman
2025/0332168 A1 10/2025 Waldman
2025/0332169 A1 10/2025 Waldman
2025/0339430 A1 11/2025 Waldman
2025/0339431 A1 11/2025 Waldman
2025/0345330 A1 11/2025 Waldman
2025/0360131 A1 11/2025 Waldman
2025/0367194 A1 12/2025 Waldman
2025/0367195 A1 12/2025 Waldman
2025/0367196 A1 12/2025 Waldman
2025/0367197 A1 12/2025 Waldman
2025/0367198 A1 12/2025 Waldman
2025/0367199 A1 12/2025 Waldman
2025/0367200 A1 12/2025 Waldman
2025/0375448 A1 12/2025 Waldman
2025/0381186 A1 12/2025 Waldman
2025/0387394 A1 12/2025 Waldman
2026/0007670 A1 1/2026 Waldman
2026/0014150 A1 1/2026 Waldman
2026/0014151 A1 1/2026 Waldman
2026/0014152 A1 1/2026 Waldman
2026/0034129 A1 2/2026 Waldman
2026/0053800 A1 2/2026 Waldman
2026/0083737 A1 3/2026 Waldman
2026/0083738 A1 3/2026 Waldman
2026/0091034 A1 4/2026 Waldman
2026/0091035 A1 4/2026 Waldman
2026/0097035 A1 4/2026 Waldman
2026/0102398 A1 4/2026 Waldman
2026/0102399 A1 4/2026 Waldman
2026/0108516 A1 4/2026 Waldman

(56) References Cited

U.S. PATENT DOCUMENTS

2026/0108517 A1 4/2026 Waldman
2026/0108518 A1 4/2026 Waldman
2026/0108519 A1 4/2026 Waldman
2026/0108520 A1 4/2026 Waldman
2026/0115193 A1 4/2026 Waldman
2026/0124206 A1 5/2026 Waldman
2026/0124207 A1 5/2026 Waldman
2026/0124208 A1 5/2026 Waldman
2026/0130909 A1 5/2026 Waldman
2026/0130911 A1 5/2026 Waldman
2026/0130912 A1 5/2026 Waldman
2026/0130913 A1 5/2026 Waldman
2026/0130914 A1 5/2026 Waldman
2026/0130915 A1 5/2026 Waldman
2026/0130916 A1 5/2026 Waldman
2026/0137683 A1 5/2026 Waldman
2026/0144790 A1 5/2026 Waldman
2026/0144791 A1 5/2026 Waldman
2026/0151393 A1 6/2026 Waldman
2026/0158034 A1 6/2026 Waldman
2026/0158035 A1 6/2026 Waldman
2026/0158036 A1 6/2026 Waldman
2026/0158037 A1 6/2026 Waldman
2026/0166034 A1 6/2026 Waldman
2026/0174752 A1 6/2026 Waldman
2026/0174753 A1 6/2026 Waldman
2026/0174754 A1 6/2026 Waldman
2026/0174755 A1 6/2026 Waldman
2026/0174756 A1 6/2026 Waldman
2026/0174758 A1 6/2026 Waldman
2026/0174759 A1 6/2026 Waldman
2026/0183289 A1 7/2026 Waldman
2026/0183290 A1 7/2026 Waldman
2026/0183291 A1 7/2026 Waldman
2026/0183292 A1 7/2026 Waldman
2026/0183293 A1 7/2026 Waldman
2026/0199337 A1 7/2026 Waldman
2026/0199338 A1 7/2026 Waldman
2026/0207593 A1 7/2026 Waldman
2026/0207594 A1 7/2026 Waldman
2026/0207595 A1 7/2026 Waldman
2026/0207596 A1 7/2026 Waldman
2026/0207597 A1 7/2026 Waldman
2026/0207598 A1 7/2026 Waldman
2026/0207599 A1 7/2026 Waldman
2026/0216185 A1 7/2026 Waldman
2026/0216186 A1 7/2026 Waldman
2026/0248790 A1 8/2026 Waldman
2026/0256783 A1 9/2026 Waldman
2026/0256784 A1 9/2026 Waldman
2026/0256785 A1 9/2026 Waldman
2026/0263466 A1 9/2026 Waldman
2026/0272927 A1 9/2026 Waldman
2026/0272928 A1 9/2026 Waldman
2026/0284047 A1 9/2026 Waldman

FOREIGN PATENT DOCUMENTS

CA 2576556 C 4/2014
CA 2579382 C 5/2015
CA 2705083 C 9/2017
CN 110755286 A 2/2020
CN 113413405 A 9/2021
CN 114129527 A 3/2022
CN 118304268 A 7/2024
EP 976395 A1 2/2000
EP 1695708 A2 8/2006
EP 2863896 B1 9/2016
EP 3689324 A1 8/2020
IN 208784 B 5/2007
IN 3053/MUM/2010 A 6/2013
IN 202211025909 A 5/2022
IN 202421055307 A 10/2024
JP 2009531461 A 9/2009
JP 2014500275 A 1/2014
JP 2017533265 A 11/2017
JP 2019172655 A 10/2019
JP 2020527146 A 9/2020
JP 2021031438 A 3/2021
JP 7118743 B2 8/2022
JP 7222236 B2 2/2023
KR 20080026754 A1 3/2008
KR 20090029255 A 3/2009
KR 102003606 A 4/2019
KR 102003606 B1 7/2019
KR 20200028403 A 3/2020
MX 2010005067 A 11/2011
WO 8302558 A1 8/1983
WO 200006129 A1 2/2000
WO 2000059475 A1 10/2000
WO 2002007685 A2 1/2002
WO 2002007700 A2 1/2002
WO 2003055464 A1 7/2003
WO 2004032919 A1 4/2004
WO 2004058229 A1 7/2004
WO 2004100857 A2 11/2004
WO 2005017134 A1 2/2005
WO 2006057637 A1 6/2006
WO 2007014061 A2 2/2007
WO 2007144082 A2 12/2007
WO 2009000038 A1 12/2008
WO 2009040818 A1 4/2009
WO 2009040818 A9 5/2010
WO 2012059936 A1 5/2012
WO 2012059936 A4 5/2012
WO 2012068299 A2 5/2012
WO 2012068299 A9 6/2012
WO 2016040462 A2 6/2012
WO 2016065426 A1 5/2016
WO 2019165208 A1 8/2019
WO 2021107926 A1 6/2021
WO 2023055740 A1 4/2023
WO 2024091572 A1 5/2024
WO 2024124206 A1 6/2024
WO 2024125086 A1 6/2024
WO 2024189607 A1 9/2024
WO 2024199216 A1 10/2024
WO 2024254056 A1 12/2024
WO 2025226875 A1 10/2025

OTHER PUBLICATIONS

Vañó-Galván et. al. "Safety of low-dose oral minoxidil for hair loss: A multicenter study of 1404 patients" Journal of the American Academy of Dermatology, vol. 84, Issue 6, Jun. 2021, pp. 1644-1651.
International Search Report and Written Opinion for Application PCT/US2023/035920 dated Feb. 27, 2024.
Junqueira et al. "Coupling of Fused Deposition Modeling and Inkjet Printing to Produce Drug Loaded 30 Printed Tablets" 2022, Pharmaceutics 14(159): 1-13.
"Reynolds et al. "Investigation of the Effect of TabletSurface Area/Volume on Drug Releasefrom Hydroxypropylmethylcel-luloseControlled-Release Matrix Tablets"" Drug Development and Industrial Pharmacy, 28(4), 457-466 (2002).
Fleishaker et al., "The Pharmacokinetics of 2.5- to 10-mg Oral Doses of Minoxidil in Healthy Volunteers", 1989, J. Clin. Pharma-cology 29:162-167.
Fan et al., "An Artificial Neural Network for Multi-objective Simultaneous Optimization of HPMC Sustained Release Tablet Formulations", Journal of Chinese Pharmaceutical Sciences, vol. 39, No. 10, Oct. 2004, pp. 768-771, English Abstract Attached.
Loniten Minoxidil 10 mg Tablet Bottle, Pfizer Australia Pty Ltd, Australian Register of Therapeutic Goods (ARTG) Entry: 12309, Available online at URL<https://www.tga.gov.au/resources/artg/12309>, Aug. 2, 1991, 2 pages.
Ramirez-Marin et al., "Role of Oral Minoxidil in Patterned Hair Loss", Indian Dermatology Online Journal, Oct. 12, 2022, vol. 13, No. 6, p. 729-733, DOI: 10.4103/idoj.idoj_246_22.
Randolph et al., "Oral minoxidil treatement for hair loss: A review of efficacy and safety", Journal of the American Academy of

(56) References Cited

OTHER PUBLICATIONS

Dermatology, vol. 84, No. 3, Mar. 2021 (Mar. 2021), pp. 737-746, XP093332243, US, ISSN: 0190-9622, DOI: 10-1016/j.jaad 2020-06-1009.
Jimenez-Cauhe et al., Safety of low-dose oral minoxidil treatment for hair loss. A systematic review and pooled-analysis of individual patient data, Dermatologic Therapy, vol. 33, No. 6, Sep. 7, 2020, CP093332241, US ISSN: 1396-0296, DOI: 10-1111/dth.14106.
York et al., "A review of the treatment of male pattern hair loss", Expert Opinion Pharmacotherapy, vol. 21, No. 5, Mar. 23, 2020 (Mar. 23, 2020), pp. 603-612, XP055845339, London, UK, ISSN: 1465-6566, DOI:10.1080/14656566.2020.1721463, pp. 605-606.
Lowenthal et al., "Pharmacology and Pharmacokinetics of Minoxidil", Journal of Cardiovascular Pharmacology, vol. 2 (Suppl. 2): S93-S106.
Gupta et al., "There Is a Positive Dose-Dependent Association between Low-Dose Oral Minoxidil and Its Efficacy for Androgenetic Alopecia: Findings from a Systematic Review with Meta-Regression Analyses", Systematic Review and Meta-Analysis, Skin Appendage Disorders 2022;8:355-361, DOI: 10.1159/000525137, Published online: Jun. 30, 2022.
Gupta et al., "Low-Dose Oral Minoxidil for Alopecia: A Comprehensive Review", Guidelines, Skin Appendage Disorders 2023;9:423-437, DOI: 10.1159/000531890, Published online: Sep. 27, 2023.
Jain et al., "The influence of hydroxypropyl methylcellulose (HPMC) molecular weight, concentration and effect of food on in vivo erosion behavior of HPMC matrix tablets", Journal of Controlled Release 187 (2014) 50-58, journal homepage: www.elsevier.com/locate/jconrel.
Buhl et al., "Potassium Channel Conductance as a Control Mechanism in Hair Follicles", The Journal of Investigative Dermatology vol. 101, No. 1, Supplement, Jul. 1993, 148S-152S.
Buhl et al., "Potassium Channel Conductance: A Mechanism Affecting Hair Growth both in Vitro and In Vivo", The Journal of Investigative Dermatology vol. 98, No. 3, Mar. 1992, 315-319.
Messenger et al., "Minoxidil: mechanisms of action on hair growth", British Journal of Dermatology 2004: 150: 186-194.
Shorter et al., "Human hair follicles contain two forms of ATP-sensitive potassium channels, only one of which is sensitive to minoxidil", The FASEB Journal vol. Jun. 22, 2008, 1725-1736.
Mehta et al., "Minoxidil sulfotransferase enzymatical activity in plants: A novel paradigm in increasing minoxidil response in androgenetic alopecia", Journal of Cosmetic Dermatology, 2024;23:339-343.
Villani et al., "Review of Oral Minoxidil As Treatment of Hair Disorders: In Search of the Perfect Dose", Journal of the European Academy of Dermatology and Venereology, vol. 35, 2021, pp. 1485-1492.
Ramos et al., "Minoxidil 1 mg oral versus minoxidil 5% topical solution for the treatment of female-pattern hair loss: A randomized clinical trial", J. Am Acad Dermatol, Jan. 2020, 82(1):252-253. doi: 10.1016/j.jaad.2019.08.060. Epub Aug. 29, 2019.
Pharmacia & Upjohn /Pfizer, Minoxidil (LONITEN) tablets - Prescribing Information (FDA label, rev. 2015). 2015., https://www.accessdata.fda.gov/drugsatfda_docs/label/2015/018154s026lbl.pdf, 16 pgs.
International Search Report and Written Opinion for Application PCT/US2025/026067 dated Jul. 9, 2025, 13 pgs.
Bokhari et al., "Sublingual minoxidil for the treatment of male and female pattern hair loss: a randomized, double-blind, placebo-controlled, phase 1B clinical trial" JEADV. 2022, PMID 34420241doi:10.1111/jdv. 17623, 6 pgs.
Health Canada Drug Product Database, Minoxidil topical Product Monograph (Rogaine 2% and equivalents), Clinical Pharmacology—Systemic Effects. https://pdf.hres.ca/dpd_pm/00040937.PDF, 59 pgs.
Sobota, "Review of cardiovascular findings in humans treated with minoxidil", Toxicol Pathol. 1989. PMID 2665032doi: 10.1177/019262338901700115, 10 pgs.
Fonseca et al., "Oral minoxidil 2.5 mg versus 5 mg for male androgenetic alopecia: a double-blind randomized clinical trial", J Am Acad Dermatol. 2025. DOI: 10.1016/j.jaad.2025.09.031. PMID: 40962189, 3 pgs.
Sanabria et al., "Oral minoxidil 7.5 mg for hair loss increases heart rate with No. change in blood pressure in 24-h Holter and 24-h ABPM", An Bras Dermatol. 2024. DOI: 10.1016/j.abd.2023.08.016., 3 pgs.
Sanabria et al., "Prospective 24-h Holter and ABPM in 34 men using 5 mg/day oral minoxidil for androgenetic alopecia", J Am Acad Dermatol. 2023;88(2):436-437. DOI: 10.1016/j.jaad.2022.05.026.
Gupta et al., "Low-Dose Oral Minoxidil and Associated Adverse Events: Analyses of the FDA Adverse Event Reporting Sytem (FAERS) With a Focus on Pericardial Effusions", J Cosmet Dermatol. 2025;24:e16574. DOI: 10.1111/jocd.16574, 10 pgs.
Buhl et al., "Minoxidil sulfate is the active metabolite that stimulates hair follicles", J Invest Dermatol. 1990;95 (5):553-557. DOI: 10.1111/1523-1747.ep12504905. PMID: 2230218.
Roberts et al., "Sulfotransferase activity in plucked hair follicles predicts response to topical minoxidil in the treatment of female androgenetic alopecia", Dermatologic Therapy 27(4) (2014): 252-254. DOI: 10.1111/dth. 12130.
Bakst et al., "Food-dependent prolonged-release oral minoxidil suppresses peak systemic exposure: dissolution and pilot pharmacokinetic characterization", Anagen General Intelligence. 2026, https://anagen.xyz/treatment-science/minx#s2, last accessed on Jul. 10, 2026.
Donovan Hair Clinic, "Top 10 things you need to know about oral minoxidil for hair loss", https://donovanmedical.com/hair-blog/oral-minoxidil-top-10, accessed Jul. 10, 2026, 9 pgs.
Salas et al., "Characterizing low-dose oral minoxidil-induced peripheral edema in alopecia patients", Journal of the American Academy of Dermatology, Brief Report vol. 92, Issue 3, Mar. 2025, last accessed on Jul. 20, 2026, 5 pgs.
International Search Report and Written Opinion for Application PCT/US2026/026628 dated Jul. 14, 2026, 16 pgs.
*Anagen LLC, Petitioner*, v. *Veradermics, Incorporated, Patent Owner*, Petition for Post-Grant Review of Claims 1-20 of U.S. Pat. No. 12,491,184 under 35 U.S.C §§ 321-329 and 37 CFR. § 42.200, Sep. 1, 2026, U.S. Patent Trial and Appeal Board.
*Anagen LLC, Petitioner*, v. *Veradermics, Incorporated, Patent Owner*, Declaration of Hossein Omidian, Ph.D., Petition for Post-Grant Review of U.S. Pat. No. 12,491,184, Sep. 1, 2026, U.S. Patent Trial and Appeal Board.
Gottlieb et al., Pharmacokinetic studies of minoxidil, Clin. Pharmacol. Ther., 13(3): 436-441, 1972.
Beach et al., Low-dose oral minoxidil for treating alopecia: A 3-year North American retrospective case series, J. Am. Acad. Dermatol. 84(3):761-763, 2021.
Rowe, "Hypromellose", Handbook of Pharmaceutical Excipients, 5th Edition, Jan. 1, 2006, Pharmaceutical Press, Chicago, London, XP055781217, pp. 346-349.

* cited by examiner

COMPOSITIONS AND METHODS OF USE FOR MODIFIED RELEASE MINOXIDIL

CROSS-REFERENCE TO RELATED APPLICATIONS

This Application is a continuation under 35 U.S.C. § 111(a) of U.S. patent application Ser. No. 19/094,703 filed Mar. 28, 2025, which is a continuation under 35 U.S.C. § 111(a) of U.S. patent application Ser. No. 18/437,724 filed on Feb. 9, 2024, now U.S. Pat. No. 12,268,688 issued on Apr. 8, 2025, which is a continuation under 35 U.S.C. § 111(a) of International Patent Application No. PCT/US2023/035920 filed on Oct. 25, 2023, which claims priority to U.S. Provisional Application No. 63/419,155 filed on Oct. 25, 2022, and to U.S. Provisional Application No. 63/433,203 filed on Dec. 16, 2022, which are incorporated herein by reference in their entirety.

BRIEF DESCRIPTION OF THE DRAWINGS

For a fuller understanding of the nature and advantages of the present embodiments, reference should be made to the following detailed description taken in connection with the accompanying drawings, in which.

SUMMARY

Figure 1:
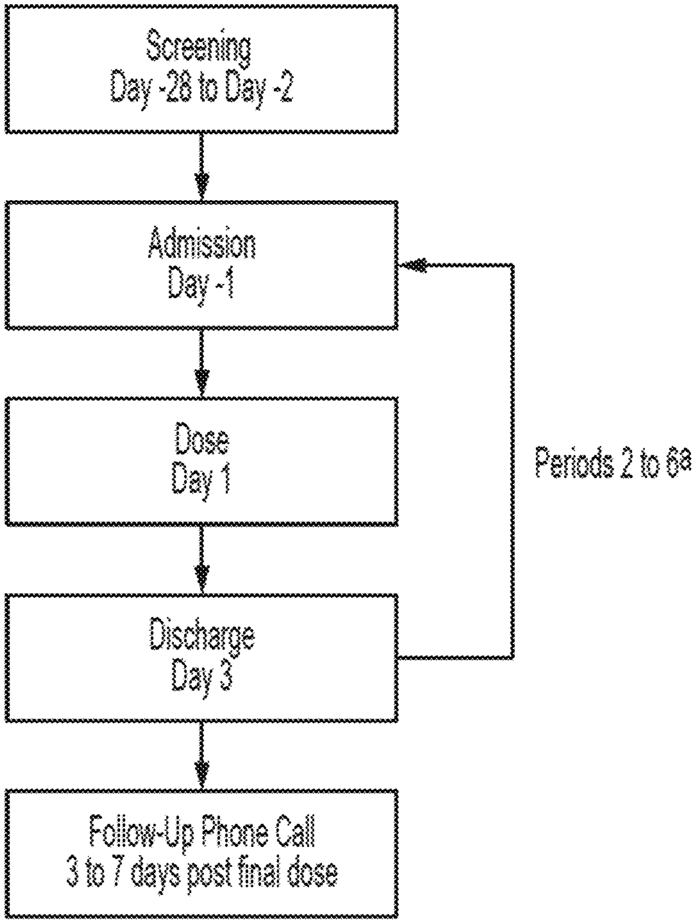
FIG. 1 depicts a study design: Between each investigational medicinal product (IMP) administration, there will be a minimum washout of 7 days and also sufficient time to permit the decision process and product manufacture.

In some aspects, the techniques described herein relate to a pharmaceutical formulation for oral administration, including a daily dose of minoxidil or a pharmaceutically acceptable salt thereof, wherein the pharmaceutical formulation is a modified release formulation.

In some aspects, the techniques described herein relate to a pharmaceutical formulation comprising a modified release formulation of minoxidil or a pharmaceutically acceptable salt thereof, wherein the modified release formulation releases about 50% to about 98% of the daily dose of minoxidil or a pharmaceutically acceptable salt thereof within about 12 hours after oral administration.

In some aspects, the techniques described herein relate to a pharmaceutical formulation comprising a modified release formulation of minoxidil or a pharmaceutically acceptable salt thereof, wherein the modified release formulation has a Tmax of about 30 to about 360 minutes.

In some aspects, the techniques described herein relate to a pharmaceutical formulation comprising a modified release formulation of minoxidil or a pharmaceutically acceptable salt thereof, wherein the modified release formulation has a Cmax of about 0.25 ng/ml to about 20 ng/ml.

In some aspects, the techniques described herein relate to a method of treating hair loss, including administering to a subject in need thereof a daily dose of a composition including a modified release formulation of minoxidil or a pharmaceutically acceptable salt thereof.

In some aspects, the techniques described herein relate to a method of treating hair loss, comprising administering to a subject in need thereof a modified release formulation of minoxidil or a pharmaceutically acceptable salt thereof, wherein the modified release formulation releases about 50% to about 98% of the daily dose of minoxidil or a pharmaceutically acceptable salt thereof within about 12 hours after oral administration.

In some aspects, the techniques described herein relate to a method of treating hair loss, comprising administering to a subject in need thereof a modified release formulation of minoxidil or a pharmaceutically acceptable salt thereof, wherein the modified release formulation has a Tmax of about 30 to about 360 minutes.

In some aspects, the techniques described herein relate to a method of treating hair loss, comprising administering to a subject in need thereof a modified release formulation of minoxidil or a pharmaceutically acceptable salt thereof, wherein the modified release formulation has a Cmax of about 0.25 ng/ml to about 20 ng/ml.

In some aspects, the techniques described herein relate to a kit including, a slow modified release vehicle including oral minoxidil or a pharmaceutically acceptable salt thereof.

DETAILED DESCRIPTION

This disclosure is not limited to the particular systems, devices and methods described, as these may vary. The terminology used in the description is for the purpose of describing the particular versions or embodiments only, and is not intended to limit the scope. Such aspects of the disclosure be embodied in many different forms; rather, these embodiments are provided so that this disclosure will be thorough and complete, and will fully convey its scope to those skilled in the art.

The present disclosure is not to be limited in terms of the particular embodiments described in this disclosure, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or disclosure. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

All percentages, parts and ratios are based upon the total weight of the compositions and all measurements made are at about 25° C., unless otherwise specified.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art. Where the context of the disclosure indicates otherwise, or is inconsistent with such an interpretation, the above-stated interpretation may be modified as would be readily apparent to a person skilled in the art. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The terms "administer," "administering," and "administration" as used herein refer to either directly administering a compound (also referred to as an agent of interest) or pharmaceutically acceptable salt of the compound (agent of interest) or a composition to a subject.

The term "adverse effect" as use herein refers to undesired harmful effect resulting from the administration of a pharmaceutical formulation. An adverse effect can be selected from peripheral edema, tachycardia, hypotension, lightheadedness, and hirsutism. An "adverse effect" can also be referred to as a side effect.

The term "animal" as used herein includes, but is not limited to, humans and non-human vertebrates such as wild, domestic, and farm animals.

The term "cardiac condition" as used herein refers to any condition related to the heart or vascular system. A cardiac condition can be selected heart disease, hypotension (including orthostatic hypotension), chronic congestive heart failure, cardiomyopathy, tachyarrhythmia (including atrial fibrillation, premature ventricular contractions, supraventricular tachycardia, ventricular fibrillation, etc.), renal disease, preexisting pulmonary hypertension, and chronic congestive heart failure not secondary to hypertension.

The term "cardiac effect" as used herein refers to any effect on the heart or the vascular system as a result of the administration of a pharmaceutical formulation. A cardiac effect can be a hemodynamic change in blood pressure. A cardiac effect can be selected from tachycardia, hypotension, premature ventricular contractions, and other tachyarrhythmias.

The terms "clinical significance" or "clinically significant" as used herein refer to the practical importance of a treatment effect on daily life.

The term "composition" as used herein refers to a combination or a mixture of two or more different ingredients, components, or substances.

The term "daily" as used herein refers to administration within a single day.

The term "disorder" as used herein refers to an abnormal condition of the human or animal body or of one of its parts that impairs normal functioning, is typically manifested by distinguishing signs and symptoms, and causes the human or animal to have a reduced duration or quality of life. The term "disorder" can be used interchangeably with the terms "disease," "condition," or "illness," unless otherwise indicated.

The term "excipients" as used herein encompasses carriers and diluents, meaning a material, composition or vehicle, such as a liquid or solid filler, diluent, excipient, solvent or encapsulating material involved in carrying or transporting a pharmaceutical, cosmetic or other agent across a tissue layer such as the stratum corneum or stratum *spinosum.*

The term "first order release" as used herein, refers to the rate of drug release, wherein the drug release rate is proportional to the concentration of one of the reactants. In a first order release, the rate law is: rate=k[A] (or B instead of A), with k having the units of sec-1.

The term "hair loss" as used herein refers to excessive hair loss. Hair loss can be from the scalp. Hair loss can be male pattern hair loss, female pattern hair loss, hereditary hair loss, telogen effluvium, anagen effluvium, alopecia areata, cicatricial alopecia (including central centrifugal cicatricial alopecia, lichen planopilaris, frontal fibrosing alopecia, etc.), or traction alopecia.

The term "hair regrowth" as used herein refers to the growth of hair to restore hair after hair loss. Hair regrowth can be measured with commonly accepted measurements including a target area hair count (TAHC) and pattern hair loss specific grading systems (e.g. Hamilton Norwood scale, Sinclair scale, Ludwig scale, etc.).

The term "improvement" as used herein refers to a state that is better than another state.

The term "modified release" as used herein refers to pharmaceutical compositions that do not otherwise release the entirety of the active ingredient immediately. For example, it may release the active ingredient at a sustained or controlled rate over an extended period of time, or may release the active ingredient after a lag time after administration, or may be used optionally in combination with an immediate release composition. Modified release includes extended release, sustained release, controlled release, and delayed release. The term "extended release" or "sustained release" as used herein is a dosage form that makes a drug available over an extended period of time after administration relative to a dose delivered in an entirely immediate release form. The term "delayed release" as used herein is a dosage form that releases a drug at a time other than immediately upon administration. The terms "orally" and "oral" and "oral administration" as used herein refer to the route of administration where a substance is taken through the mouth.

The term "pharmaceutical formulation" as used herein refers to a substance that contains a combination of excipients and an active pharmaceutical ingredient to create a medicinal product. As used herein, the term "pharmaceutical agent" or "compound" refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "pharmacokinetics" as used herein refers to the movement of a drug within a body and the elimination of a drug from a body. The term "pharmacokinetic profile" as used herein refers to the measurements of the pharmacokinetic properties of a drug, a compound, or a formulation. A pharmacokinetic profile the following measurements: half-life, Cmax, Tmax and area under the plasma concentration-time curve (AUC). The term "half-life" as used herein refers to the time required for a drug, a compound, or a formulation to be reduced to half of the initial amount. The term "effective half-life" as used herein refers the rate of accumulation or elimination of a biochemical or pharmacological substance in an organism; it is the analogue of biological half-life when the kinetics are governed by multiple independent mechanisms. The term "plasma concentration versus time" as used herein refers to the measurement of the concentration of the active ingredient in the plasma over time. The term "Cmax" as used herein refers to maximum serum concentration that a drug, a compound, or a formulation achieves after administration of a single dose. The term "Tmax" as used herein refers to the time it takes for a drug, a compound, or a formulation to reach the maximum concentration after administration of a single dose. The term "AUC" as used herein refers to the total drug exposure in the plasma over time.

The term "pseudo zero order release," as used herein, refers to the rate of drug release, wherein the drug release appears to follow zero order kinetics, but is actually a result of a first order reaction with a large excess of one of the reactants. In a zero order reaction, the rate of the reaction is independent of the concentration of the reactants.

The term "pseudo first order release," as used herein, refers to the rate of drug release, wherein the drug release is a second order or bimolecular reaction that is made to behave like a first-order reaction. This reaction occurs when one reacting material is present in great excess or is maintained at a constant concentration compared with the other substance.

The term "second order release," as used herein, refers to the rate of drug release, wherein the drug release has a rate proportional to the concentration of the square of a single reactant or the product of the concentration of two reactants. In a second order release, the rate law is: rate=k[A]2 (or substitute B for A or k multiplied by the concentration of A times the concentration of B), with the units of the rate constant M-1 sec-1.

The term "skin" as used herein refers to the thin layer of tissue forming the natural outer covering of the body of a person or animal. The skin is made of the epidermis and dermis. The term "scalp" as used herein refers to the skin on a patient's head.

The term "steady state" as used here in refers to when the quantity of drug eliminated in the unit of time equals the quantity of the drug that reaches the systemic circulation in the unit of time. The term "steady state blood level" as used herein refers to the time when the amount of drug in the blood is constant. This occurs when the amount of the drug being absorbed is the same amount being cleared from the body when a drug is being administered repeatedly.

The term "subject" and "patient" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

The term "subtherapeutic" or "subtherapeutically effective amount" of a compound or composition is a dose or concentration of a drug that is lower than what is usually prescribed to treat a disease effectively.

As used herein, the term "therapeutic" or "therapeutic agent" or "pharmaceutically active agent" or "active agent" means an agent utilized to treat, combat, ameliorate, prevent or improve an unwanted condition or disease of a patient.

A "therapeutically effective amount" or "effective amount" of a compound or composition is a predetermined amount calculated to achieve the desired effect, i.e., to inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range. However, it will be understood that the effective amount administered will be determined by the physician in the light of the relevant circumstances including the condition to be treated, the choice of compound to be administered, and the chosen route of administration, and therefore the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The term "treat," "treated," or "treating" as used herein refers to both therapeutic treatment and prophylactic or preventative measures, wherein the object is to reduce the frequency of, or delay the onset of, symptoms of a medical condition, enhance the texture, appearance, color, sensation, or hydration of the intended tissue treatment area of the tissue surface in a subject relative to a subject not receiving the compound or composition, or to otherwise obtain beneficial or desired clinical results. For the purposes of this invention, beneficial or desired clinical results include, but are not limited to, reversal, reduction, or alleviation of symptoms of a condition; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

The term "zero order release" as used herein, refers to the rate of drug release, wherein the drug release is constant and independent of the concentration of the reactants. In a zero order release, the rate law is: rate=k, with k having the units of M/sec.

In some embodiments, the compounds and methods disclosed herein can be utilized with or on a subject in need of such treatment, which can also be referred to as "in need thereof" As used herein, the phrase "in need thereof" means that the subject has been identified as having a need for the particular method or treatment and that the treatment has been given to the subject for that particular purpose.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, structures, or groups thereof, or any members of a claimed group, less than the full measure of this disclosure can be claimed for any reason. Throughout this disclosure, various patents, patent applications and publications are referenced. The disclosures of these patents, patent applications and publications are incorporated into this disclosure by reference in their entireties in order to more fully describe the state of the art as known to those skilled therein as of the date of this disclosure. This disclosure will govern in the instance that there is any inconsistency between the patents, patent applications and publications cited and this disclosure.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

Pharmaceutical Formulation

Embodiments described herein are directed to a pharmaceutical formulation for oral administration, comprising a daily dose of minoxidil or a pharmaceutically acceptable salt thereof, wherein the pharmaceutical formulation is a modified release formulation.

In some embodiments, the pharmaceutical formulation described herein comprises minoxidil or a pharmaceutically acceptable salt thereof, a release modifier, a filler, a glidant, a lubricant, and combinations thereof.

In some embodiments, the pharmaceutical formulation described herein comprises minoxidil or a pharmaceutically acceptable salt thereof in an amount of about 0.075% to about 33% (w/w) of the total formulation. In some embodiments, the pharmaceutical formulation described herein comprises minoxidil or a pharmaceutically acceptable salt thereof in an amount of about 0.083% to about 33% (w/w) of the total formulation. In some embodiments, the pharmaceutical formulation described herein comprises minoxidil or a pharmaceutically acceptable salt thereof in an amount of about 0.1% to about 20% (w/w) of the total formulation. In some embodiments, the pharmaceutical formulation comprises minoxidil or a pharmaceutically acceptable salt thereof or a pharmaceutically acceptable salt thereof in an amount of about 1% to about 10% (w/w) of the total formulation. In some embodiments, the pharmaceutical formulation comprises minoxidil or a pharmaceutically acceptable salt thereof in an amount of about 1% to about 5% (w/w) of the total formulation. In some embodiments, the pharmaceutical formulation comprises minoxidil or a pharmaceutically acceptable salt thereof in an amount of about 1% to about 1.5% (w/w) of the total formulation. In some embodiment, the pharmaceutical formulation comprises minoxidil or a pharmaceutically acceptable salt thereof or a pharmaceutically acceptable salt thereof in an amount (w/w) of about 0.075%, about 0.1%, about 0.25%, about 0.5%, about 0.75%, about 1%, about 1.5%, about 2%, about 2.5%, about 3%, about 3.5%, about 4%, about 5%, about 6%, about 7%, about 8%, about 9%, about 10%, about 12%, about 14%, about 15%, about 16%, about 18%, about 20%, about 25%, about 30%, about 33%, or any range within these values.

In some embodiments, the pharmaceutical formulation described herein comprises a release modifier in an amount of about 20% to about 95% (w/w) of the total formulation. In some embodiments, the pharmaceutical formulation comprises a release modifier in an amount of about 50% to about 80% (w/w) of the total formulation. In some embodiments, the pharmaceutical formulation comprises a release modifier in an amount (w/w) of about 20%, about 25%, about 30%, about 40%, about 45%, about 50%, about 55%, about 60%, about 65%, about 70%, about 75%, about 80%, about 85%, about 90%, about 95%, or any range within these values.

In some embodiments, the pharmaceutical formulation described herein comprises a glidant in an amount of about 0.01% to about 2% (w/w) of the total formulation. In some embodiments, the pharmaceutical formulation comprises glidant in an amount of about 0.1% to about 0.3% (w/w) of the total formulation. In some embodiments, the pharmaceutical formulation comprises glidant in an amount (w/w) of about 0.01%, about 0.02%, about 0.03%, about 0.04%, about 0.05%, about 0.06%, about 0.07%, about 0.08%, about 0.09%, about 0.1%, about 0.15%, about 0.2%, about 0.25%, about 0.35%, or any range within these values.

In some embodiment, the pharmaceutical formulation described herein comprises a lubricant in an amount of about 0.1% to about 1% (w/w) of the total formulation. In some embodiments, the pharmaceutical formulation comprises lubricant in an amount of about 0.4% to about 0.6% (w/w) of the total formulation. In some embodiments, the pharmaceutical formulation comprises lubricant in an amount (w/w) of about 0.1%, about 0.2%, about 0.3%, about 0.4%, about 0.5%, about 0.6%, about 0.7%, about 0.8%, about 0.9%, about 1%, or any range within these values.

In some embodiments, the release modifier is hydroxy propyl methylcellulose (HPMC) or lactose monohydrate. In some embodiments, the hydroxypropyl methylcellulose is HPMC K4M or HPMC K200M. In some embodiments, the HPMC K4M is in an amount of 0 mg to about 45 mg in a 150 mg formulation. In some embodiments, the HPMC K4M is 0% to about 30% (w/w) of the total formulation. In some embodiments, the HPMC K200M is in an amount of 0 mg to about 120 mg in a 150 mg formulation. In some embodiments, the HPMC K200M is about 0% to about 80% of the total formulation. In some embodiments, the lactose monohydrate is in an amount of about 0 mg to about 55 mg in a 150 mg formulation. In some embodiments, the lactose monohydrate is about 0 to about 40% of the total formulation.

In some embodiments, the filler is microcrystalline cellulose. In some embodiments, the microcrystalline cellulose is in an amount of about of about 25 mg to about 55 mg in a 150 mg formulation. In some embodiments, the microcrystalline cellulose is about 15% to about 40% (w/w) of the total formulation.

In some embodiments, the glidant is silica (colloidal anhydrous), starch, talc, magnesium stearate, calcium stearate, zinc stearate, dibasic calcium phosphate, magnesium carbonate, magnesium oxide, calcium silicate, silicon dioxide, silicon dioxide, colloidal silicon dioxide, talc, sodium lauryl sulfate, native starch, or combinations thereof. In some embodiments, the glidant is silica. In some embodiments the silica is colloidal anhydrous. In some embodiments, the glidant is in an amount of about 0.3 mg to about 5 mg in a 150 mg formulation. In some embodiments, the glidant is about 0.001% to about 0.04% (w/w) of the total formulation.

In some embodiments, the lubricant is magnesium stearate, calcium stearate, zinc stearate, stearic acid, hydrogenated vegetable oils, sterotex, polyoxyethylene, monostearate, talc, polyethyleneglycol, sodium benzoate, sodium lauryl sulfate, magnesium lauryl sulfate, light mineral oil, or combinations thereof. In some embodiments, the lubricant is in an amount of about 0.75 mg to about 1.5 mg in a 150 mg formulation. In some embodiments, the lubricant is about 0.005% to about 0.01% (w/w) of the total formulation.

In some embodiments, the pharmaceutical formulation described herein further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2a analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof. In some embodiments, the pharmaceutical formulation further comprises medrogestone, cetirizine, setipiprant, valproic acid, and combinations thereof.

In any embodiment of the pharmaceutical formulation described herein, the non-steroid anti-androgen is selected from flutamide, clascoterone, bicalutamide, pyrilutamide, enzualutamide, nilutamide, apalutamide, proxilutamide, cimetidine, topalutamide, and combinations thereof. In any embodiment, the 17α-hydroxyprogesterone derivative is selected from chlormadinone acetate, cyproterone acetate, megestrol acetate, osaterone acetate, and combinations thereof. In any embodiment, the 19-norprogesterone derivative is nomegestrol acetate. In any embodiment, 19-nortestosterone derivative is selected from dienogest, oxendolone, and combinations thereof. In any embodiment, the 17α-spirolactone derivative is selected from drospirenone, spironolactone, and combinations thereof. In any embodiment, the 5-alpha reductase inhibitor is selected from alfatradiol, dutasteride, epristeride, finasteride, saw palmetto extract, bexlosteride, izonsteride, epigallocatechin, fluridil, and combinations thereof. In any embodiment, the estrogen is selected from estradiol, estradiol esters, ethinylestradiol, conjugated estrogens, diethylstilbestrol, and combinations thereof. In any embodiment, the GnRH analog is a GnRH agonist wherein the GnRH agonist is selected from goserelin, buserelin, leuprorelin, and combinations thereof. In any embodiment, the GnRH analog is a GnRH antagonist wherein the GnRH antagonist is cetrorelix. In any embodiment, the prostaglandin F2α analog is latanoprost, travoprost, tafluprost, unoprostone, dinoprost, AS604872, BOL303259X, PF3187207, carboprost, and combinations thereof. In any embodiment, the prostamide is bimatoprost. In any embodiment, the prostanoid receptor agonist is fluprostenol, cicaprost, and combinations thereof. In any embodiment, the prostaglandin D2 receptor antagonist is laropiprant, AM211, and combinations thereof. In any embodiment, the prostaglandin E2 analog is sulprostone. In any embodiment, the EP2 receptor agonist is butaprost, diazoxide, kopexil, pinacidil, ET-02, and combinations thereof. In any embodiment, the JAK inhibitor is abrocitinib, baricitinib, brepocitinib, decernotinib, delgocitinib, deuruxolitinib, deucravacitinib, fedratinib, filgotinib, gusacitinib, itacitinib, oclacitinib, pacritinib, peficitinib, ritlecitnib, ruxolitinib, tofacitinib, upadacitinib, SHR0302, ATI-2138, jacktinib, and combinations thereof. In any embodiment, the alopecia areata medication is selected from etrasimod, fingolimod, ozanimod, siponimod, ponesimod, and combinations thereof. In any embodiment, the supplement is selected from biotin, zinc, selenium, caffeine, sodium chloride, marine collagen, and combinations thereof.

In some embodiments of the pharmaceutical formulation described herein, the modified release formulation is selected from an extended release formulation, a sustained release formulation, a controlled release formulation, or a delayed release formulation. In some embodiments, the modified release formulation may release the minoxidil or a pharmaceutically acceptable salt thereof a pharmaceutically acceptable salt thereof at a sustained or controlled rate over an extended period of time, or may release it after a lag time after administration. For example, it may be released from the composition 4 hours after administration, 8 hours after administration, 12 hours after administration, 16 hours after administration, or 24 hours after administration. Modified release formulations include extended release, sustained release, a controlled release formulation, and delayed release compositions. In some examples, the modified release compositions may release about 10% in about 2 hours, about 20% in 2 hours, about 40% in about 2 hours, about 50% in about 2 hours, about 10% in about 3 hours, about 20% in 3 hours, about 40% in about 3 hours, about 50% in about 3 hours, about 10% in about 4 hours, about 20% in 4 hours, about 40% in about 4 hours, about 50% in about 4 hours, about 10% in about 6 hours, about 20% in 6 hours, about 40% in about 6 hours, or about 50% in about 6 hours.

In some embodiments of the pharmaceutical formulation described herein, the extended release formulation releases about 50% to about 98% of the daily dose of minoxidil or a pharmaceutically acceptable salt thereof within about 12 hours after the oral administration. In some embodiments of the pharmaceutical formulation described herein, the extended release formulation releases about 50% to about 98% of the daily dose of minoxidil or a pharmaceutically acceptable salt thereof within about 18 hours after the oral administration. In some embodiments described herein, the extended release formulation releases about 50%, about 55%, about 60%, about 65%, about 70%, about 75%, about 80%, about 85%, about 90%, about 95%, about 98% of the daily dose of minoxidil or a pharmaceutically acceptable salt thereof within about 12 to about 18 hours after the oral administration, or any range within these values.

In some embodiments of the pharmaceutical formulation described herein, the controlled release formulation releases about 50% to about 98% of the daily dose of minoxidil or a pharmaceutically acceptable salt thereof within about 12 hours after the oral administration. In some embodiments, the controlled-release formulation releases about 50%, about 55%, about 60%, about 65%, about 70%, about 75%, about 80%, about 85%, about 90%, about 95%, about 98% of the daily dose of minoxidil or a pharmaceutically acceptable salt thereof within about 12 hours after the oral administration, or any range within these values.

In some embodiments of the pharmaceutical formulation described herein, the delayed release formulation releases the daily dose of minoxidil or a pharmaceutically acceptable salt thereof within about 6 hours after the oral administration. In some embodiments, the delayed release formulation releases the daily dose of minoxidil or a pharmaceutically acceptable salt thereof in multiple distinct releases each within about 18 hours after the oral administration.

In some embodiments, the pharmaceutical formulation described herein, exhibits a dissolution profile wherein about 25% of the formulation dissolves in a neutral pH solution in less than about 2 hours or less than about 4 hours. In some embodiments, about 25% of the formulation dissolves in a neutral pH solution at about 0.5 hours, about 0.75 hours, about, 1 hour, about 1.5 hours, about 2 hours, about 2.5 hours, about 3 hours, or about 4 hours.

In some embodiments, the pharmaceutical formulation described herein, exhibits a dissolution profile wherein about 50% of the formulation dissolves in a neutral pH solution in less than about 2 hours, less than about 6 hours, or less than about 12 hours. In some embodiments, about 50% of the formulation dissolves in a neutral pH solution at about 1 hour, about 1.5 hours, about 2 hours, about 3 hours, about 4 hours, about 6 hours, about 8 hours, or about 10 hours.

In some embodiments, the pharmaceutical formulation described herein, exhibits a dissolution profile wherein about 75% of the formulation dissolves in a neutral pH solution in less than about 4 hours, less than about 8 hours, less than about 12 hours, or less than about 18 hours. In some embodiments, about 75% of the formulation dissolves in a neutral pH solution at about 3 hours, about 3.5 hours, about 4 hours, about 4.5 hours, about 5 hours, about 6 hours, about 8 hours, about 10 hours, about 12 hours, about 14 hours, or about 16 hours.

In some embodiments, the pharmaceutical formulation described herein, exhibits a dissolution profile wherein about 100% of the formulation dissolves in a neutral pH in less than about 12 hours, less than about 24 hours, or less than about 48 hours. In some embodiments, about 100% of the formulation dissolves in a neutral pH at about 10 hours, about 12 hours, about 14 hours, about 16 hours, about 18 hours, about 20 hours, about 22 hours, about 24 hours, about 26 hours, or about 28 hours.

In some embodiments, the pharmaceutical formulation described herein exhibits a zero order release of minoxidil or a pharmaceutically acceptable salt thereof, a pseudo zero order release of minoxidil or a pharmaceutically acceptable salt thereof, a first order release of minoxidil or a pharmaceutically acceptable salt thereof, a pseudo first order release of minoxidil or a pharmaceutically acceptable salt thereof, or a second order release of minoxidil or a pharmaceutically acceptable salt thereof.

In some embodiments of the pharmaceutical formulation described herein, the minoxidil or a pharmaceutically acceptable salt thereof is in a therapeutically effective amount. In some embodiments, the one or more active agents are in a therapeutically effective amount. In some embodiments, the pharmaceutical formulation comprises minoxidil or a pharmaceutically acceptable salt thereof in a subtherapeutic amount. In some embodiments, the pharmaceutical formulation comprises one or more active agents in a subtherapeutic amount. In some embodiments, the pharmaceutical formulation comprises minoxidil or a pharmaceutically acceptable salt thereof and one or more active agents wherein the minoxidil or a pharmaceutically acceptable salt thereof and the one or more active agents are each in subtherapeutic amounts.

In some embodiments of the pharmaceutical formulation described herein, the daily dose of minoxidil or a pharmaceutically acceptable salt thereof is in an amount of about 0.25 mg to about 50 mg. In some embodiments, the daily dose of minoxidil or a pharmaceutically acceptable salt thereof is in an amount of about 0.5 mg to about 2.5 mg. In some embodiments, the daily dose of minoxidil or a pharmaceutically acceptable salt thereof is in an amount of about 0.625 mg to about 7.5 mg. In some embodiments, the daily dose of minoxidil or a pharmaceutically acceptable salt thereof is in an amount of about 0.5 mg to about 10 mg. In some embodiments, the daily dose of minoxidil or a pharmaceutically acceptable salt thereof is about 0.25 mg to about 20 mg. In some embodiments, the daily dose of minoxidil or a pharmaceutically acceptable salt thereof is in an amount of about 0.125 mg to about 100 mg. In some embodiments, the daily dose of minoxidil or a pharmaceutically acceptable salt thereof is about 2.5 mg. In some embodiments, the daily dose of minoxidil or a pharmaceutically acceptable salt thereof is in an amount of about 0.125 mg, about 0.25 mg, about 5 mg, about 0.625 mg, about 0.75 mg, about 1 mg, about 1.25 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 9 mg, about 10 mg, about 12 mg, about 15 mg, about 18 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, or any range within these values.

In some embodiments of the pharmaceutical formulation described herein, the daily dose of minoxidil or a pharmaceutically acceptable salt thereof is administered to a subject in an amount of about 0.000625 mg/kg/day to about 1.25 mg/kg/day. In some embodiments of the pharmaceutical formulation described herein, the daily dose of minoxidil or a pharmaceutically acceptable salt thereof is administered to a subject in an amount of about 0.00625 mg/kg/day to about 0.5 mg/kg/day. In some embodiments, the daily dose of the minoxidil or a pharmaceutically acceptable salt thereof is about 0.00625 mg/kg/day to about 0.375 mg/kg/day. In some embodiments, the daily dose of the minoxidil or a pharmaceutically acceptable salt thereof is about 0.000625 mg/kg/day; about 0.00125 mg/kg/day, about 0.0025 mg/kg/day, about 0.00375 mg/kg/day, about 0.005 mg/kg/day, about 0.00625 mg/kg/day, about 0.0125 mg/kg/day, about 0.025 mg/kg/day, about 0.0375 mg/kg/day, about 0.05 mg/kg/day, about 0.0625 mg/kg/day, about 0.075 mg/kg/day, about 0.0875 mg/kg/day, about 0.1 mg/kg/day, about 0.125 mg/kg/day, about 0.25 mg/kg/day, about 0.5 mg/kg/day, about 0.75 mg/kg/day, about 1 mg/kg/day, about 1.25 mg/kg/day, or any range within these values.

In some embodiments of the pharmaceutical formulation described herein, the pharmaceutical formulation is administered only once daily. In some embodiments, the pharmaceutical formulation is administered at least once daily. In some embodiments, the pharmaceutical formulation is administered four times per day. In some embodiments, the pharmaceutical formulation is administered three times per day. In some embodiments, the pharmaceutical formulation is administered two times per day.

In some embodiments of the pharmaceutical formulation described herein, the oral administration of the daily dose of minoxidil or a pharmaceutically acceptable salt thereof results in a steady state blood level of the minoxidil or a pharmaceutically acceptable salt thereof of about 1 ng/ml to about 20 ng/ml. In some embodiments, the steady state blood level of the daily dose of minoxidil or a pharmaceutically acceptable salt thereof is maintained for at least about 12 hours. In some embodiments, the steady state blood level of the daily dose of minoxidil or a pharmaceutically acceptable salt thereof is maintained for at least about 6 hours, at least about 8 hours, at least about 10 hours, or any range within these values.

In some embodiments of the pharmaceutical formulation described herein, the oral administration of the daily dose minoxidil or a pharmaceutically acceptable salt thereof results in a Cmax of about 0.25 ng/ml to about 20 ng/ml. In some embodiments, the oral administration of the daily dose minoxidil or a pharmaceutically acceptable salt thereof results in a Cmax that is devoid of cardiac effects.

In some embodiments of the pharmaceutical formulation described herein, the oral administration of the daily dose of minoxidil or a pharmaceutically acceptable salt thereof results in a Tmax of about 30 to about 360 minutes. In some embodiments, the oral administration of the daily dose of minoxidil or a pharmaceutically acceptable salt thereof results in a delayed release that results in a Tmax between both 30 to 360 minutes and between 390 minutes and 1080 minutes.

In some embodiments of the pharmaceutical formulation described herein, the oral administration of the daily dose of modified release minoxidil or a pharmaceutically acceptable salt thereof results in an AUC that is greater than an equivalent dose of an immediate release formulation. In some embodiments of the pharmaceutical formulation described herein, the oral administration of the daily dose of the modified release minoxidil or a pharmaceutically acceptable salt thereof results in an AUC that is less than an equivalent dose of immediate release formulation. In some embodiments of the pharmaceutical formulation described herein, the oral administration of the daily dose of the modified release minoxidil or a pharmaceutically acceptable salt thereof results in an AUC that is equal to an equivalent dose of immediate release formulation.

Embodiments described herein are directed to a pharmaceutical formulation comprising a modified release formulation of minoxidil or a pharmaceutically acceptable salt thereof, wherein the modified release formulation releases about 50% to about 98% of the daily dose of minoxidil or a pharmaceutically acceptable salt thereof within about 12 hours after oral administration.

In some embodiments, the pharmaceutical formulation further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof. In some embodiments, the pharmaceutical formulation further comprises medrogestone, cetirizine, setipiprant, valproic acid, and combinations thereof.

Embodiments described herein are directed to a pharmaceutical formulation comprising a modified release formulation of minoxidil or a pharmaceutically acceptable salt thereof, wherein the modified release formulation has a Tmax of about 30 to about 360 minutes.

In some embodiments, the pharmaceutical formulation further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof. In some embodiments, the pharmaceutical formulation further comprises medrogestone, cetirizine, setipiprant, valproic acid, and combinations thereof.

Embodiments described herein are directed to a pharmaceutical formulation comprising a modified release formulation of minoxidil or a pharmaceutically acceptable salt thereof, wherein the modified release formulation has a Cmax of about 0.25 ng/ml to about 20 ng/ml.

In some embodiments, the pharmaceutical formulation further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof. In some embodiments, the pharmaceutical formulation further comprises medrogestone, cetirizine, setipiprant, valproic acid, and combinations thereof.

In some embodiments of the pharmaceutical formulation described herein, the oral administration results in a half-life or effective half-life of the daily dose of minoxidil or a pharmaceutically acceptable salt thereof of about 1 hour to about 24 hours. In some embodiments, the oral administration results in a half-life or effective half-life of the daily dose of minoxidil or a pharmaceutically acceptable salt thereof of about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, about 24 hours, or any range within these values.

In some embodiments of the pharmaceutical formulation described herein, the subject has a minoxidil or a pharmaceutically acceptable salt thereof plasma concentration versus time curve with a Tmax of about 30 to about 360 minutes.

In some embodiments, the pharmaceutical formulation is an inert solid vehicle, or matrix, in which a drug is uniformly suspended, including in the form of tablets or small beads. In some embodiments, the matrix is a gelling material including gelatin, methylcellulose, gum tragacanth, Veegum, and alginic acid. In some embodiments, the matrix is a polymer including polylactic acid copolymer, polyacrylate, methacrylate, polyester, ethylene-vinyl acetate copolymer (EVA), polyglycolide, polylactide, and silicone. In some embodiments, the modified release formulation is a slow-release pellet, bead, or granule. In some embodiments, the modified release formulation is an extended release tablet where the solubility of a drug is modified for extended release. In some embodiments, the extended release tablet is formed by using the nonionized base or acid form of the drug. In some embodiments, the extended release tabled is formed by granulating the drug with excipients (including stearic acid, castor wax, high-molecular-weight polyethylene glycol (Carbowax), glyceryl monosterate, white wax, spermaceti oil, magnesium stearate and hydrogenated vegetable oil (Sterotex)) to decrease the aqueous solubility of the drug. In some embodiments, the modified release formulation is an ion-exchange preparation whereby an anionic or cationic drug is complexed with an oppositely charged ionic resin to form an insoluble nonabsorbable resin-drug complex.

In some embodiments of the pharmaceutical formulation described herein, the pharmaceutical formulation is a tablet. In some embodiments, the tablet is a sustained release or controlled release tablet. The sustained release or controlled release tablet may be an osmotic pump type controlled release tablet, a matrix type controlled release tablet or a sustained and controlled release tablet based on sustained release pellets. Among them, the osmotic pump type controlled release tablets include osmotic pump controlled release tablets and osmotic pump immediate and sustained double-release tablets, and the matrix type controlled release tablets include matrix type sustained release tablets, matrix type immediate and sustained double-release double layer tablets and matrix type immediate and sustained double-release coated tablets, etc. The sustained and controlled release tablets based on sustained release pellets include sustained release tablets based on sustained release pellets, and immediate and sustained double-release tablets based on sustained release pellets and immediate release pellets. The sustained and controlled release tablet described above can specifically achieve the drug release behavior of the present invention in the following manners: osmotic pump type controlled release tablets, matrix type controlled release tablets, or sustained release tablets based on sustained release pellets.

The osmotic pump controlled release tablet of the invention may be a single layer osmotic pump tablet, a single layer osmotic pump immediate and sustained double-release tablet, a double layer osmotic pump controlled release tablet or a double layer osmotic pump immediate and sustained double release tablet. The double-layer osmotic pump controlled release tablet of the invention mainly comprises: 1) a controlled release drug layer, which is formed by a controlled release drug layer composition, located in a rigid film shell and adjacent to the drug release pore; 2) a push layer (also referred to as a boost layer), which is formed by a push layer composition, located in a rigid film shell, and away from the side of the drug release pore; 3) an optional seal coat layer located between the inner surface of the rigid film shell and the core composed of the drug layer and the push layer, and prepared from the seal coating composition by drying; 4) a rigid film shell having moisture permeability, which is obtained by drying a controlled release coating solution and has one or more drug release pores at one end of the film shell; 5) an optional non-limiting aesthetic outer coat; 6) an optional non-limiting immediate release drug layer formed by an immediate release drug composition, located outside the rigid film shell/or the optional aesthetic outer coat. Further description of the controlled release formulations can be found in U.S. Publication No. 20200108008, which is incorporated herein by reference in its entirety.

The matrix type controlled release tablets of the present invention can have an immediate and sustained double release behavior. The controlled release matrix type tablet of the invention mainly consists of a sustained release phase and an optional immediate release phase. The double-layer tablet composed of the sustained release phase and immediate release phase is an immediate and sustained double release matrix type tablet, and the single-layer tablet composed only of the sustained release phase is an ordinary sustained release matrix type tablet. The sustained release phase comprises 100 to 900 parts by weight, preferably 150 to 700 parts by weight, more preferably 200 to 600 parts by weight, of the minoxidil or pharmaceutically acceptable salt thereof in an improved dissolution form, 10 to 300 parts by weight, preferably 30 to 150 parts by weight of a release rate adjusting matrix polymer, 0 to 50 parts by weight of a diluent, and 0.2 to 30 parts by weight, preferably 1 to 30 parts by weight, of other common additives for tablets. The sustained release phase was prepared by thoroughly mixing the components and pressing through common methods well known for those skilled in the art. The release rate adjusting matrix polymer may be one or a combination of two or more selected from the group consisting of polyoxyethylene, hydroxypropyl cellulose, hypromellose, methyl cellulose, hydroxyethyl cellulose, ethyl cellulose, sodium alginate, povidone, copolyvidone, acrylic resin, carbomer; preferably one or a combination of two or more selected from the group consisting of hydroxypropylcellulose, sodium alginate, hypromellose, and carbomer.

The sustained release tablets based on sustained release pellets of the present invention can be a sustained release tablet based on sustained release pellets, or an immediate and sustained double release tablet based on an immediate release matrix/sustained release pellets.

In some embodiments of the pharmaceutical formulation described herein, the pharmaceutical formulation is a capsule. In some embodiments, the capsule is a controlled release capsule preparation which is selected from the group consisting of a pellet-based sustained and controlled release capsule and a tablet-based sustained and controlled release capsule. In some embodiments, the capsule is a microtablet based controlled release capsule. The pellet-based sustained and controlled release capsule of the present invention is a controlled release capsule composed of sustained release pellets, or an immediate and sustained double release capsule composed of sustained release pellets and immediate release pellets, and may include capsules containing matrix type sustained release pellets, capsules containing coated sustained release pellets, capsules containing sustained release pellets having immediate release coat, immediate and sustained double-release capsules containing immediate release pellets and matrix type sustained release pellets, and immediate and sustained double-release capsules containing immediate release pellets and coated sustained release pellets.

The microtablet based sustained and controlled release capsules of the invention is controlled release capsules composed of sustained release microtablets or immediate and sustained double release capsules composed of sustained release microtablets and immediate release microtablets, and may include capsules containing matrix type sustained release microtablets, capsules containing matrix type sustained release microtablets with immediate release coat, and capsules containing immediate release microtablets and matrix type sustained release microtablets. In general, for the filling of hard capsules, the produced microtablets have a small diameter of typically <5 mm.

In some embodiments of the pharmaceutical formulation described herein, the pharmaceutical formulation further comprises an enteric coating. One or more coatings can comprise an enteric coating, which is a coating on tablets that delays digestion of the tablets until they pass from the stomach into the intestines. Enterically coated formulations bypass the acidic environment of the stomach in order to eliminate the effect of acidic pH on the solubility of minoxidil. Enteric coatings typically comprise pH sensitive polymers. The polymers can be carboxylate and generally interact very little with water at low pH. At a high pH, however, the polymers ionize, thereby causing dissolving of the polymer. Coatings can thus be designed to remain intact in the acidic environment of the stomach, but to dissolve in the more alkaline environment of the intestine. Examples include cellulose acetate phthalate, hydroxypropylmethylethylcellulose succinate, hydroxypropylmethylcellulose phthalate, polyvinyl acetate phthalate, and methacrylic acid-methyl methacrylate copolymer. In one aspect, the first surface coating comprises polyvinyl alcohol. In a further aspect, the first surface coating comprises methacrylic acid-ethyl acrylate copolymer. In a further aspect, the first surface coating comprises polyvinyl alcohol and methacrylic acid-ethyl acrylate copolymer. In a further aspect, the first surface coating is an enteric coating comprising one or more of polyvinyl alcohol or methacrylic acid-ethyl acrylate copolymer. In a further aspect, the first surface coating is an enteric coating comprising one or more of CAP, PVAP, acrylic polymers, acrylic copolymers, HPMCAS, HPMCP, or shellac. Further description of the enteric coating can be found in U.S. Publication No. 20170020920, which is incorporated herein by reference in its entirety.

In some embodiments of the pharmaceutical formulation described herein, the pharmaceutical formulation further comprises one or more pharmaceutically acceptable excipients. Examples of pharmaceutically acceptable excipients that may be present in the composition include but are not limited to fillers/vehicles, solvents/co-solvents, preservatives, antioxidants, suspending agents, surfactants, antifoaming agents, buffering agents, chelating agents, sweeteners, flavoring agents, binders, extenders, disintegrants, diluents, lubricants, fillers, wetting agents, glidants, and combinations thereof.

In some embodiments of the pharmaceutical formulation described herein, the pharmaceutical formulation can further comprise one or more exemplary fillers. Examples of exemplary fillers include cellulose and cellulose derivatives such as microcrystalline cellulose, powdered cellulose; dextrates; starches such as dry starch, hydrolyzed starch, and starch derivatives such as corn starch; cyclodextrin; sugars such as powdered sugar and sugar alcohols such as lactose, mannitol, sucrose and sorbitol; inorganic fillers such as aluminum hydroxide gel, calcium carbonate (granules or powder), precipitated calcium carbonate, carbonate, magnesium aluminometasilicate, dibasic calcium phosphate; and sodium chloride, silicon dioxide, silicic acid, titanium dioxide, titanium oxide, dicalcium phosphate dihydrate, calcium sulfate, alumina, kaolin, talc, or combinations thereof. Fillers may be present in the composition from about 20 wt % to about 65 wt %, about 20 wt % to about 50 wt %, about 20 wt % to about 40 wt %, about 45 wt % to about 65 wt %, about 50 wt % to about 65 wt %, or about 55 wt % to about 65 wt % of the total weight of the composition, or any value between these ranges.

In some embodiments of the pharmaceutical formulation described herein, the pharmaceutical formulation further comprises one or more disintegrants. Examples of disintegrants include starches, alginic acid, crosslinked polymers such as crosslinked polyvinylpyrrolidone, croscarmellose sodium, potassium starch glycolate, sodium starch glycolate, clays, celluloses, starches, gums, or combinations thereof. Disintegrants may be present in the composition from about 1 wt % to about 10 wt %, about 1 wt % to about 9 wt %, about 1 wt % to about 8 wt %, about 1 wt % to about 7 wt %, about 1 wt % to about 6 wt %, or about 1 wt % to about 5 wt % of the total weight of the composition, or any value between these ranges.

In some embodiments of the pharmaceutical formulation described herein, the pharmaceutical formulation further comprises one or more binders, including but not limited to celluloses such as hydroxypropylcellulose, methyl cellulose, and hydroxypropylmethylcellulose; starches such as corn starch, pregelatinized starch, and hydroxypropyl starch; waxes and natural and synthetic gums such as acacia, tragacanth, sodium alginate; synthetic polymers such as polymethacrylates and polyvinylpyrrolidone; and povidone, dextrin, pullulane, agar, gelatin, tragacanth, macrogol, or combinations thereof. Binders may be present in the composition from about 0.5 wt % to about 5 wt %, about 0.5 wt % to about 4 wt %, about 0.5 wt % to about 3 wt %, about 0.5 wt % to about 2 wt %, or about 0.5 wt % to about 1 wt % of the total weight of the composition, or any value between these ranges.

In some embodiments of the pharmaceutical formulation described herein, the pharmaceutical formulation further comprises one or more wetting agents, including but not limited to oleic acid, glyceryl monostearate, sorbitan monooleate, sorbitan monolaurate, triethanolamine oleate, polyoxyethylene sorbitan mono-oleate, polyoxyethylene sorbitan monolaurate, sodium oleate, sodium lauryl sulfate, poloxamers, poloxamer 188, polyoxyethylene ethers, polyoxyethylene sorbitan fatty acid esters, polyoxyethylene fatty acid esters, polyethylene glycol fatty acid esters, polyoxyethylene hardened castor oil, polyoxyethylene alkyl ethers, polysorbates, cetyl alcohol, glycerol fatty acid esters (for example, triacetin, glycerol monostearate, etc.), polyoxymethylene stearate, sodium lauryl sulfate, sorbitan fatty acid esters, sucrose fatty acid esters, benzalkonium chloride, polyethoxylated castor oil, and combinations thereof. Wetting agents may be present in the composition from about 0.1 wt % to about 1 wt %, about 0.1 wt % to about 2 wt %, about 0.1 wt % to about 3 wt %, about 0.1 wt % to about 4 wt %, or about 0.1 wt % to about 5 wt % of the total weight of the composition, or any value between these ranges.

In some embodiments of the pharmaceutical formulation described herein, the pharmaceutical formulation further comprises one or more lubricants, including but not limited to stearic acid, magnesium stearate, calcium hydroxide, talc, corn starch, sodium stearyl fumarate, alkali-metal and alkaline earth metal salts, waxes, boric acid, sodium benzoate, sodium acetate, sodium chloride, leucine, polyethylene glycol (PEG), a methoxypolyethylene glycol, propylene glycol, sodium oleate, glyceryl behenate, glyceryl palmitostearate, glyceryl benzoate, magnesium lauryl sulfate, sodium lauryl sulfate, and combinations thereof. Lubricants may be present in the composition from about 0.1 wt % to about 5 wt %, about 0.1 wt % to about 4 wt %, about 0.1 wt % to about 3 wt %, about 0.1 wt % to about 2 wt %, or about 0.1 wt % to about 1 wt % of the total weight of the composition, or any value between these ranges.

In some embodiments, the glidant is silica (colloidal anhydrous), starch, talc, magnesium stearate, calcium stearate, zinc stearate, dibasic calcium phosphate, magnesium carbonate, magnesium oxide, calcium silicate, silicon dioxide, silicon dioxide, colloidal silicon dioxide, talc, sodium lauryl sulfate, native starch, and combinations thereof. Glidants may be present in the composition from about 0.05 wt % to about 1 wt %, about 0.05 wt % to about 0.9 wt %, about 0.05 wt % to about 0.8 wt %, about 0.05 wt % to about 0.5 wt %, or about 0.05 wt % to about 0.1 wt % of the total weight of the composition, or any value between these ranges.

In some embodiments of the pharmaceutical formulation described herein, the pharmaceutical formulation is a tablet and further comprises a top coat, such as hydroxypropylmethylcellulose coating or polyvinyl alcohol coating, and are available under the trade name Opadry, such as Opadry White, Opadry II (Opadry is a registered trademark of BPSI Holdings LLC, Wilmington, DE, USA). Top coats may be present in the composition from about 1 wt % to about 10 wt %, about 1 wt % to about 9 wt %, about 1 wt % to about 8 wt %, about 1 wt % to about 7 wt %, about 1 wt % to about 6 wt %, or about 1 wt % to about 5 wt % of the total weight of the composition, or any value between these ranges.

In some embodiments of the pharmaceutical formulation described herein, the pharmaceutical formulation can further comprise one or more preservative agents. Examples of preservative agents include sodium benzoate, paraoxybenzoic acid esters, methyl, ethyl, butyl, and propyl parabens, chlorobutanol, benzyl alcohol, phenylethylalcohol, dehydroacetic acid, sorbic acid, benzalkonium chloride (BKC), benzethonium chloride, phenol, phenylmercuric nitrate, thimerosal, or combinations thereof. Preservative agents can be included in the liquid dosage form. The preservative agents can be in an amount sufficient to extend the shelf-life or storage stability, or both, of the liquid dosage form. Preservatives may be present in the composition from about 0.05 wt % to about 1 wt %, about 0.05 wt % to about 0.9 wt %, about 0.05 wt % to about 0.8 wt %, about 0.05 wt % to about 0.5 wt %, or about 0.05 wt % to about 0.1 wt % of the total weight of the composition, or any value between these ranges.

In some embodiments of the pharmaceutical formulation described herein, the pharmaceutical formulation can further comprise one or more flavoring agents. Examples of flavoring agents include synthetic flavor oils and flavoring aromatics and/or natural oils, extracts from plants leaves, flowers, fruits, and so forth and the like or any combinations thereof. Additional examples include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil and the like or any combinations thereof. Also useful as flavors are vanilla, citrus oil, including lemon, orange, grape, lime and grapefruit, and fruit essences, including apple, banana, pear, peach, strawberry, raspberry, cherry, plum, pineapple, apricot, strawberry flavor, tutti-fruity flavor, mint flavor, or any combinations thereof. Flavoring agents may be present in the composition from about 0.1 wt % to about 5 wt %, about 0.1 wt % to about 4 wt %, about 0.1 wt % to about 3 wt %, about 0.1 wt % to about 2 wt %, or about 0.1 wt % to about 1 wt % of the total weight of the composition, or any value between these ranges.

The pharmaceutical formulation can generally be in any physical form suitable for use in treating a subject. These forms can be referred to as a unit dosage form, such as an individual pill or tablet. In some examples, the pharmaceutical compositions can be formulated as tablets, capsules, granules, powders, liquids, suspensions, gels, syrups, slurries, suppositories, patches, nasal sprays, aerosols, injectables, implantable sustained-release formulations, or mucoadherent films. In some examples, the pharmaceutical formulation may be formed as a tablet, a bi-layer tablet, a capsule, a multiparticulate, a drug coated sphere, a matrix tablet, or a multicore tablet. A physical form can be selected according to the desired method of treatment.

Pharmaceutical formulation can be manufactured by various conventional methods such as conventional mixing, dissolving, granulating, dragee-making, levigating, emulsifying, encapsulating, entrapping, or lyophilizing processes. Pharmaceutical formulations can be formulated in a conventional manner using one or more physiologically acceptable carriers, diluents, excipients or auxiliaries that facilitate processing of the active agent into preparations that can be used pharmaceutically. Proper formulation can be selected upon the oral route of administration chosen.

In some embodiments, the pharmaceutical formulation is a core tablet, or a tablet within a tablet, whereby the inner core is used for the slow-drug-release component, and the outside shell contains a rapid-release dose of drug. In some embodiments, pharmaceutical formulation is achieved via microencapsulation whereby microscopic drug particles are encapsulated with a special coating material, such as ethylcellulose. In some embodiments, the pharmaceutical formulation is an osmotic drug delivery system in the form of a tablet which contains an outside semipermeable membrane and an inner core filled with a mixture of drug and osmotic agent (salt solution). In some embodiments, the pharmaceutical formulation is a gastroretentive system that can remain in the gastric region for several hours and prolong the gastric residence time of a drug. In some embodiments, the pharmaceutical formulation is a combination of any of the above-described embodiments.

For oral administration, the pharmaceutical formulation can combine minoxidil or a pharmaceutically acceptable salt thereof with another pharmaceutical agent with one or more pharmaceutically acceptable carriers well known in the art. Such carriers facilitate formulation as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added. For buccal administration, the compositions may take the form of tablets, lozenges, etc. formulated in conventional manner.

In some examples, modified release formulations may comprise a matrix selected from microcrystalline cellulose, sodium carboxymethylcellulose, hydroxyalkylcelluloses such as hydroxy propyl methylcellulose and hydroxypropylcellulose, polyethylene oxide, alkylcelluloses such as methylcellulose and ethylcellulose, polyethylene glycol, polyvinylpyrrolidone, cellulose acetate, cellulose acetate butyrate, cellulose acetate phthalate, cellulose acetate trimellitate, polyvinyl acetate phthalate, polyalkylmethacrylates, polyvinyl acetate and mixtures thereof.

Methods of Treating Hair Loss

Embodiments described herein are directed to a method of treating hair loss, comprising administering to a subject in need thereof a daily dose of a composition comprising a modified release formulation of minoxidil or a pharmaceutically acceptable salt thereof.

In some embodiments of the methods described herein, the composition comprises minoxidil or a pharmaceutically acceptable salt thereof, a release modifier, a filler, a glidant, a lubricant, and combinations thereof.

In some embodiments, the methods described herein comprise minoxidil or a pharmaceutically acceptable salt thereof in an amount of about 0.075% to about 33% (w/w) of the total formulation. In some embodiments, the methods described herein comprise minoxidil or a pharmaceutically acceptable salt thereof in an amount of about 0.083% to about 33% (w/w) of the total formulation. In some embodiments of the methods described herein, the composition comprises minoxidil or a pharmaceutically acceptable salt thereof in an amount of about 0.1% to about 20% (w/w) of the total composition. In some embodiments, the composition comprises minoxidil or a pharmaceutically acceptable salt thereof in an amount of about 1% to about 10% (w/w) of the total composition. In some embodiments, the methods comprise minoxidil or a pharmaceutically acceptable salt thereof in an amount of about 1% to about 5% (w/w) of the total formulation. In some embodiments, the methods comprise minoxidil or a pharmaceutically acceptable salt thereof in an amount of about 1% to about 1.5% (w/w) of the total formulation. In some embodiment, the composition comprises minoxidil or a pharmaceutically acceptable salt thereof in an amount (w/w) of about 0.075%, about 0.1%, about 0.25%, about 0.5%, about 0.75%, about 1%, about 1.5%, about 2%, about 2.5%, about 3%, about 3.5%, about 4%, about 5%, about 6%, about 7%, about 8%, about 9%, about 10%, about 12%, about 14%, about 15%, about 16%, about 18%, about 20%, about 25%, about 30%, about 33%, or any range within these values.

In some embodiments of the methods described herein, the composition comprises a release modifier in an amount of about 20% to about 95% (w/w) of the total composition. In some embodiments, the composition comprises a release modifier in an amount of about 50% to about 80% (w/w) of the total composition. In some embodiments, the composition comprises a release modifier in an amount (w/w) of about 20%, about 25%, about 30%, about 40%, about 45%, about 50%, about 55%, about 60%, about 65%, about 70%, about 75%, about 80%, about 85%, about 90%, about 95%, or any range within these values.

In some embodiments of the methods described herein, the composition comprises glidant in an amount of about 0.01% to about 2% (w/w) of the total composition. In some embodiments, the composition comprises glidant in an amount of about 0.1% to about 0.3% (w/w) of the total composition. In some embodiments, the composition comprises glidant in an amount (w/w) of about 0.01%, about 0.02%, about 0.03%, about 0.04%, about 0.05%, about 0.06%, about 0.07%, about 0.08%, about 0.09%, about 0.1%, about 0.15%, about 0.2%, about 0.25%, about 0.35%, or any range within these values.

In some embodiments of the methods described herein, the composition comprises lubricant in an amount of about 0.1% to about 1% (w/w) of the total composition. In some embodiments, the composition comprises lubricant in an amount of about 0.4% to about 0.6% (w/w) of the total composition. In some embodiments, the composition comprises lubricant in an amount (w/w) of about 0.1%, about 0.2%, about 0.3%, about 0.4%, about 0.5%, about 0.6%, about 0.7%, about 0.8%, about 0.9%, about 1%, or any range within these values.

In some embodiments of the methods described herein, the release modifier is hydroxy propyl methylcellulose (HPMC) or lactose monohydrate. In some embodiments, the hydroxypropyl methylcellulose is HPMC K4M or HPMC K200M. In some embodiments, the HPMC K4M is in an amount of 0 mg to about 45 mg in a 150 mg composition. In some embodiments, the HPMC K4M is 0% to about 30% (w/w) of the total composition. In some embodiments, the HPMC K200M is in an amount of 0 mg to about 120 mg in a 150 mg composition. In some embodiments, the HPMC K200M is about 0% to about 80% (w/w) of the total composition. In some embodiments, the lactose monohydrate is in an amount of about 0 mg to about 55 mg in a 150 mg composition. In some embodiments, the lactose monohydrate is about 0% to about 40% (w/w) of the total composition.

In some embodiments of the method described herein, the filler is microcrystalline cellulose, talc, calcium carbonate (e.g., granules or powder), powdered cellulose, dextrates, kaolin, mannitol, silicic acid, sorbitol, starch, pre-gelatinized starch, and mixtures thereof. In some embodiments, the filler is in an amount of about of about 25 mg to about 55 mg in a 150 mg composition. In some embodiments, the microcrystalline cellulose is about 15% to about 40% (w/w) of the total composition.

In some embodiments, the glidant is silica (colloidal anhydrous), starch, talc, magnesium stearate, calcium stearate, zinc stearate, dibasic calcium phosphate, magnesium carbonate, magnesium oxide, calcium silicate, silicon dioxide, silicon dioxide, colloidal silicon dioxide, talc, sodium lauryl sulfate, native starch, or combinations thereof. In some embodiments of the method described herein, the glidant is silica. In some embodiments the silica is colloidal anhydrous. In some embodiments, the glidant is in an amount of about 0.3 mg to about 5 mg in a 150 mg composition. In some embodiments, the glidant is about 0.001% to about 0.04% (w/w) of the total composition.

In some embodiments of the method described herein, the lubricant is magnesium stearate, calcium stearate, zinc stearate, stearic acid, hydrogenated vegetable oils, sterotex, polyoxyethylene, monostearate, talc, polyethyleneglycol, sodium benzoate, sodium lauryl sulfate, magnesium lauryl sulfate, light mineral oil, or combinations thereof. In some embodiments, the lubricant is in an amount of about 0.75 mg to about 1.5 mg in a 150 mg composition. In some embodiments, the lubricant is about 0.005% to about 0.01% (w/w) of the total composition.

In some embodiments of the method described herein, the composition further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof. In some embodiments, the composition further comprises medrogestone, cetirizine, setipiprant, valproic acid, and combinations thereof.

In any embodiment of the method described herein, the non-steroid anti-androgen is selected from flutamide, clascoterone, bicalutamide, pyrilutamide, enzualutamide, nilutamide, apalutamide, proxilutamide, cimetidine, topalutamide, and combinations thereof. In any embodiment, the 17α-hydroxyprogesterone derivative is selected from chlormadinone acetate, cyproterone acetate, megestrol acetate, osaterone acetate, and combinations thereof. In any embodiment, the 19-norprogesterone derivative is nomegestrol acetate. In any embodiment, 19-nortestosterone derivative is selected from dienogest, oxendolone, and combinations thereof. In any embodiment, the 17α-spirolactone derivative is selected from drospirenone, spironolactone, and combinations thereof. In any embodiment, the 5-alpha reductase inhibitor is selected from alfatradiol, dutasteride, epristeride, finasteride, saw palmetto extract, bexlosteride, izonsteride, epigallocatechin, fluridil, and combinations thereof. In any embodiment, the estrogen is selected from estradiol, estradiol esters, ethinylestradiol, conjugated estrogens, diethylstilbestrol, and combinations thereof. In any embodiment, the GnRH analog is a GnRH agonist wherein the GnRH agonist is selected from goserelin, buserelin, leuprorelin, and combinations thereof. In any embodiment, the GnRH analog is a GnRH antagonist wherein the GnRH antagonist is cetrorelix. In any embodiment, the prostaglandin F2α analog is latanoprost, travoprost, tafluprost, unoprostone, dinoprost, AS604872, BOL303259X, PF3187207, carboprost, and combinations thereof. In any embodiment, the prostamide is bimatoprost. In any embodiment, the prostanoid receptor agonist is fluprostenol, cicaprost, and combinations thereof. In any embodiment, the prostaglandin D2 receptor antagonist is laropiprant, AM211, and combinations thereof. In any embodiment, the prostaglandin E2 analog is sulprostone. In any embodiment, the EP2 receptor agonist is butaprost, diazoxide, kopexil, pinacidil, ET-02, and combinations thereof. In any embodiment, the JAK inhibitor is abrocitinib, baricitinib, brepocitinib, decernotinib, delgocitinib, deuruxolitinib, deucravacitinib, fedratinib, filgotinib, gusacitinib, itacitinib, oclacitinib, pacritinib, peficitinib, ritlecitnib, ruxolitinib, tofacitinib, upadacitinib, SHR0302, ATI-2138, jacktinib, and combinations thereof. In any embodiment, the alopecia areata medication is selected from etrasimod, fingolimod, ozanimod, siponimod, ponesimod, and combinations thereof. In any embodiment, the supplement is selected from biotin, zinc, selenium, caffeine, sodium chloride, marine collagen, and combinations thereof.

In some embodiments of the method described herein, the composition is administered orally. In some embodiments, the minoxidil or a pharmaceutically acceptable salt thereof is in an orally dissolving tablet.

In some embodiments of the method described herein, the modified release formulation is an extended release formulation, a controlled release formulation, or a delayed release formulation.

In some embodiments of the method described herein, the extended release formulation releases about 50% to about 98% of the daily dose of minoxidil or a pharmaceutically acceptable salt thereof within about 12 hours after the oral administration. In some embodiments of the pharmaceutical formulation described herein, the extended release formulation releases about 50% to about 98% of the daily dose of minoxidil or a pharmaceutically acceptable salt thereof within about 18 hours after the oral administration. In some embodiments described herein, the extended release formulation releases about 50%, about 55%, about 60%, about 65%, about 70%, about 75%, about 80%, about 85%, about 90%, about 95%, about 98% of the daily dose of minoxidil or a pharmaceutically acceptable salt thereof within about 12 to about 18 hours after the oral administration, or any range within these values.

In some embodiments of the method described herein, the controlled release formulation releases about 50% to about 98% of the daily dose of minoxidil or a pharmaceutically acceptable salt thereof within about 12 hours after the oral administration. In some embodiments, the controlled-release formulation releases about 50%, about 55%, about 60%, about 65%, about 70%, about 75%, about 80%, about 85%, about 90%, about 95%, about 98% of the daily dose of minoxidil or a pharmaceutically acceptable salt thereof within about 12 hours after the oral administration, or any range within these values.

In some embodiments of the method described herein, the delayed release formulation releases the daily dose of minoxidil or a pharmaceutically acceptable salt thereof within about 6 hours after the oral administration. In some embodiments, the delayed release formulation releases the daily dose of minoxidil or a pharmaceutically acceptable salt thereof in multiple distinct releases each within about 18 hours after the oral administration.

In some embodiments of the method described herein, composition described herein exhibits a dissolution profile wherein about 25% of the composition dissolves in a neutral pH solution in less than about 2 hours or less than about 4 hours. In some embodiments, about 25% of the composition dissolves in a neutral pH solution at about 0.5 hours, about 0.75 hours, about, 1 hour, about 1.5 hours, about 2 hours, about 2.5 hours, about 3 hours, or about 4 hours.

In some embodiments of the method described herein, composition described herein exhibits a dissolution profile wherein about 50% of the composition dissolves in a neutral pH solution in less than about 2 hours, less than about 6 hours, or less than about 12 hours. In some embodiments, about 50% of the composition dissolves in a neutral pH solution at about 1 hour, about 1.5 hours, about 2 hours, about 3 hours, about 4 hours, about 6 hours, about 8 hours, or about 10 hours.

In some embodiments of the method described herein, composition described herein exhibits a dissolution profile wherein about 75% of the composition dissolves in a neutral pH solution in less than about 4 hours, less than about 8 hours, less than about 12 hours, or less than about 18 hours. In some embodiments, about 75% of the composition dissolves in a neutral pH solution at about 3 hours, about 3.5 hours, about 4 hours, about 4.5 hours, about 5 hours, about 6 hours, about 8 hours, about 10 hours, about 12 hours, about 14 hours, or about 16 hours.

In some embodiments of the method described herein, composition described herein exhibits a dissolution profile wherein about 100% of the composition dissolves in a neutral pH in less than about 12 hours, less than about 24 hours, or less than about 48 hours. In some embodiments, about 100% of the composition dissolves in a neutral pH at about 10 hours, about 12 hours, about 14 hours, about 16 hours, about 18 hours, about 20 hours, about 22 hours, about 24 hours, about 26 hours, or about 28 hours.

In some embodiments of the method described herein, composition described herein exhibits a zero order release of minoxidil or a pharmaceutically acceptable salt thereof, a pseudo zero order release of minoxidil or a pharmaceutically acceptable salt thereof, a first order release of minoxidil or a pharmaceutically acceptable salt thereof, a pseudo first order release of minoxidil or a pharmaceutically acceptable salt thereof, or a second order release of minoxidil or a pharmaceutically acceptable salt thereof.

In some embodiments of the method described herein, the subject in need thereof is diagnosed with hairloss. In some embodiments, the hair loss is selected from male pattern hair loss, female pattern hair loss, hereditary hair loss, telogen effluvium, alopecia areata, central centrifugal cicatricial alopecia, lichen planopilaris, or traction alopecia.

In some embodiments of the method described herein, the administering results in hair regrowth. In some embodiments, the administering results in hair regrowth within about 1 months to about 12 months. In some embodiments, the administering results in hair regrowth within about 6 months. In some embodiments, the administering results in hair regrowth within about 4 months. In some embodiments, the administering results in hair regrowth within about 3 months. In some embodiments, the administering results in hair regrowth within about 1 month, about 2 months, about 3 months, about 4 months, about 5 months, about 6 months, about 7 months, about 8 months, about 9 months, about 10 months, about 11 months, about 12 months, or any range within these values. In some embodiments, the administering results in an increased improvement in hair growth as compared to administration of an immediate-release dosage form of minoxidil or a pharmaceutically acceptable salt thereof.

Use of the described methods and pharmaceutical formulations can result in a reduction or elimination of disease, symptom, or other undesired property in a subject relative to a control population (for example, without treatment by the described methods and materials). The reduction can generally be reduced by any amount. For example, the reduction can be at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, and in an ideal situation, about 100% reduction (complete elimination of disease, symptom, virus concentration, or other undesired property).

In some embodiments of the method described herein, the subject is diagnosed with at least one cardiac condition selected from heart disease, chronic congestive heart failure, cardiomyopathy, tachyarrhythmia, renal disease, preexisting pulmonary hypertension, and chronic congestive heart failure not secondary to hypertension.

In some embodiments of the method described herein, the subject is taking at least one of the following for treatment of the at least one cardiac condition, an anti-hypertensive, an ace-inhibitor, an angiotensin receptor blocker, a direct renin inhibitor, a loop diuretic, a thiazide diuretic, a calcium channel blocker, a beta blocker, an anti-arrhythmic, and a diuretic.

In some embodiments of the method described herein, the pharmaceutical formulation is administered only once daily. In some embodiments, the pharmaceutical formulation is administered at least once daily. In some embodiments, the pharmaceutical formulation is administered four times per day. In some embodiments, the pharmaceutical formulation is administered three times per day. In some embodiments, the pharmaceutical formulation is administered two times per day.

In some embodiments of the method described herein, the composition is administered daily for at least about 3 months with substantially no adverse effects and substantially no cardiac effects. In some embodiments, the composition is administered daily for at least 4 months with substantially no adverse effects and substantially no cardiac effects. In some embodiments, the composition is administered daily for at least 6 months with substantially no adverse effects and substantially no cardiac effects. In some embodiments, the composition is administered daily for at least 1 year with substantially no adverse effects and substantially no cardiac effects. In some embodiments, the composition is administered daily indefinitely with substantially no adverse effects and substantially no cardiac effects.

In some embodiments of the method described herein, administering results in substantially no cardiac effects. In some embodiments, the cardiac effects are selected from tachycardia, hypotension, premature ventricular contractions, and other tachyarrhythmias.

In some embodiments of the method described herein, administering results in hair regrowth with substantially no clinically significant hemodynamic changes in blood pressure. In some embodiments, administering results in hair regrowth with substantially no cardiac effects. In some embodiments, the daily dose of minoxidil or a pharmaceutically acceptable salt thereof results in substantially no cardiac effects or hemodynamic effects as compared to administration of an immediate-release oral minoxidil or a pharmaceutically acceptable salt thereof used to treat hypertension. In some embodiments, the daily dose of minoxidil or a pharmaceutically acceptable salt thereof results in substantially no cardiac effects as compared to administration of an immediate-release oral minoxidil or a pharmaceutically acceptable salt thereof used to treat hypertension.

In some embodiments of the method described herein, the daily dose amount of minoxidil or a pharmaceutically acceptable salt thereof results in fewer cardiac effects or hemodynamic effects as compared to administration of an amount of an immediate-release oral minoxidil or a pharmaceutically acceptable salt thereof used to treat hypertension. In some embodiments, the cardiac effects are selected from tachycardia, hypotension, premature ventricular contractions, and other tachyarrhythmias.

In some embodiments of the method described herein, the daily dose of minoxidil or a pharmaceutically acceptable salt thereof is about 25% to about 500% of the amount of the immediate-release oral minoxidil or a pharmaceutically acceptable salt thereof used to treat hypertension. In some embodiments, the daily dose of minoxidil or a pharmaceutically acceptable salt thereof is about 10% to about 90% of the amount of the immediate-release oral minoxidil or a pharmaceutically acceptable salt thereof used to treat hypertension. In some embodiments, the daily dose of minoxidil or a pharmaceutically acceptable salt thereof is about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 125%, about 150%, about 175%, about 200%, about 225%, about 250%, about 275%, about 300%, about 325%, about 350%, about 375%, about 400%, about 425%, about 450%, about 475%, about 500% of the amount of the immediate-release oral minoxidil or a pharmaceutically acceptable salt thereof used to treat hypertension, or any range within these values.

In some embodiments of the method described herein, the minoxidil or a pharmaceutically acceptable salt thereof is in a therapeutically effective amount. In some embodiments, the one or more active agents are in a therapeutically effective amount. In some embodiments, the pharmaceutical formulation comprises minoxidil or a pharmaceutically acceptable salt thereof in a subtherapeutic amount. In some embodiments, the pharmaceutical formulation comprises one or more active agents in a subtherapeutic amount. In some embodiments, the pharmaceutical formulation comprises minoxidil or a pharmaceutically acceptable salt thereof and one or more active agents wherein the minoxidil or a pharmaceutically acceptable salt thereof and the one or more active agents are each in subtherapeutic amounts.

In some embodiments of the method described herein, the daily dose of minoxidil or a pharmaceutically acceptable salt thereof is in an amount of about 0.25 mg to about 50 mg. In some embodiments, the daily dose of minoxidil or a pharmaceutically acceptable salt thereof is in an amount of about 0.5 mg to about 2.5 mg. In some embodiments, the daily dose of minoxidil or a pharmaceutically acceptable salt thereof is in an amount of about 0.625 mg to about 7.5 mg. In some embodiments, the daily dose of minoxidil or a pharmaceutically acceptable salt thereof is in an amount of about 0.5 mg to about 10 mg. In some embodiments, the daily dose of minoxidil or a pharmaceutically acceptable salt thereof is about 0.25 mg to about 20 mg. In some embodiments, the daily dose of minoxidil or a pharmaceutically acceptable salt thereof is in an amount of about 0.125 mg to about 100 mg. In some embodiments, the daily dose of minoxidil or a pharmaceutically acceptable salt thereof is about 2.5 mg. In some embodiments, the daily dose of minoxidil or a pharmaceutically acceptable salt thereof is in an amount of about 0.125 mg, about 0.25 mg, about 5 mg, about 0.625 mg, about 0.75 mg, about 1 mg, about 1.25 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 9 mg, about 10 mg, about 12 mg, about 15 mg, about 18 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, or any range within these values.

In some embodiments of the method described herein, the daily dose of minoxidil or a pharmaceutically acceptable salt thereof is administered to a subject in an amount of about 0.000625 mg/kg/day to about 1.25 mg/kg/day. In some embodiments of the method described herein, the daily dose of minoxidil or a pharmaceutically acceptable salt thereof is administered to a subject in an amount of about 0.00625 mg/kg/day to about 0.5 mg/kg/day. In some embodiments, the daily dose of the minoxidil or a pharmaceutically acceptable salt thereof is about 0.00625 mg/kg/day to about 0.375 mg/kg/day. In some embodiments, the daily dose of the minoxidil or a pharmaceutically acceptable salt thereof is about 0.000625 mg/kg/day; about 0.00125 mg/kg/day, about 0.0025 mg/kg/day, about 0.00375 mg/kg/day, about 0.005 mg/kg/day, about 0.00625 mg/kg/day, about 0.0125 mg/kg/day, about 0.025 mg/kg/day, about 0.0375 mg/kg/day, about 0.05 mg/kg/day, about 0.0625 mg/kg/day, about 0.075 mg/kg/day, about 0.0875 mg/kg/day, about 0.1 mg/kg/day, about 0.125 mg/kg/day, about 0.25 mg/kg/day, about 0.325 mg/kg/day, about 0.5 mg/kg/day, about 0.625 mg/kg/day, about 0.75 mg/kg/day, about 1 mg/kg/day, about 1.25 mg/kg/day, or any range within these values.

In some embodiments of the method described herein, the minoxidil or a pharmaceutically acceptable salt thereof is in an amount of about 0.625 mg four times per day.

In some embodiments of the method described herein, the modified release formulation releases about 50% to about 98% of the daily dose of minoxidil or a pharmaceutically acceptable salt thereof within about 12 hours after the oral administration.

In some embodiments of the method described herein, the oral administration of the daily dose minoxidil or a pharmaceutically acceptable salt thereof results in a Cmax of about 0.25 ng/ml to about 20 ng/ml. In some embodiments, the oral administration of the daily dose minoxidil or a pharmaceutically acceptable salt thereof results in a Cmax that is devoid of cardiac effects.

In some embodiments of the method described herein, the subject has a minoxidil or a pharmaceutically acceptable salt thereof plasma concentration versus time curve with a Tmax of about 30 to about 360 minutes. In some embodiments, the oral administration of the daily dose of minoxidil or a pharmaceutically acceptable salt thereof results in a delayed release that results in a Tmax between both 30 to 360 minutes and between 390 minutes and 1080 minutes.

In some embodiments of the method described herein, the oral administration of the daily dose of modified release minoxidil or a pharmaceutically acceptable salt thereof results in an AUC that is greater than an equivalent dose of an immediate release formulation. In some embodiments of the method described herein, the oral administration of the daily dose of the modified release minoxidil or a pharmaceutically acceptable salt thereof results in an AUC that is less than an equivalent dose of immediate release formulation. In some embodiments of the method described herein, the oral administration of the daily dose of the modified release minoxidil or a pharmaceutically acceptable salt thereof results in an AUC that is equal to an equivalent dose of immediate release formulation.

In some embodiments of the method described herein, the oral administration results in a half-life or effective half-life of the daily dose of minoxidil or a pharmaceutically acceptable salt thereof of about 1 hour to about 24 hours. In some embodiments, the oral administration results in a half-life or effective half-life of the daily dose of minoxidil or a pharmaceutically acceptable salt thereof of about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, about 24 hours, or any range within these values.

Embodiments described herein are directed to a method of treating hair loss, comprising administering to a subject in need thereof a modified release formulation of minoxidil or a pharmaceutically acceptable salt thereof, wherein the modified release formulation releases about 50% to about 98% of the daily dose of minoxidil or a pharmaceutically acceptable salt thereof within about 12 hours after oral administration.

In some embodiments of the method described herein, the composition further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof. In some embodiments, the composition further comprises medrogestone, cetirizine, setipiprant, valproic acid, and combinations thereof.

Embodiments described herein are directed to a method of treating hair loss, comprising administering to a subject in need thereof a modified release formulation of minoxidil or a pharmaceutically acceptable salt thereof, wherein the modified release formulation has a Tmax of about 30 to about 360 minutes.

In some embodiments of the method described herein, the composition further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof. In some embodiments, the composition further comprises medrogestone, cetirizine, setipiprant, valproic acid, and combinations thereof.

Embodiments described herein are directed to a method of treating hair loss, comprising administering to a subject in need thereof a modified release formulation of minoxidil or a pharmaceutically acceptable salt thereof, wherein the modified release formulation has a Cmax of about 0.25 ng/ml to about 20 ng/ml.

In some embodiments of the method described herein, the composition further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof. In some embodiments, the composition further comprises medrogestone, cetirizine, setipiprant, valproic acid, and combinations thereof.

In some embodiments of the method described herein, the modified release formulation is an inert solid vehicle, or matrix, in which a drug is uniformly suspended, including in the form of tablets or small beads. In some embodiments, the matrix is a gelling material including gelatin, methylcellulose, gum tragacanth, Veegum, and alginic acid. In some embodiments, the matrix is a polymer including polylactic acid copolymer, polyacrylate, methacrylate, polyester, ethylene-vinyl acetate copolymer (EVA), polyglycolide, polylactide, and silicone. In some embodiments, the modified release formulation is a slow-release pellet, bead, or granule. In some embodiments, the modified release formulation is an extended release tablet where the solubility of a drug is modified for extended release. In some embodiments, the extended release tablet is formed by using the nonionized base or acid form of the drug. In some embodiments, the extended release tabled is formed by granulating the drug with excipients (including stearic acid, castor wax, high-molecular-weight polyethylene glycol (Carbowax), glyceryl monosterate, white wax, spermaceti oil, magnesium stearate and hydrogenated vegetable oil (Sterotex)) to decrease the aqueous solubility of the drug. In some embodiments, the modified release formulation is an ion-exchange preparation whereby an anionic or cationic drug is complexed with an oppositely charged ionic resin to form an insoluble nonabsorbable resin-drug complex.

In some embodiments of the method described herein, the modified release formulation further comprises one or more pharmaceutically acceptable excipients. Examples of pharmaceutically acceptable excipients that may be present in the composition include but are not limited to fillers/vehicles, solvents/co-solvents, preservatives, antioxidants, suspending agents, surfactants, antifoaming agents, buffering agents, chelating agents, sweeteners, flavoring agents, binders, extenders, disintegrants, diluents, lubricants, fillers, wetting agents, glidants, and combinations thereof.

In some embodiments of the method described herein, the modified release formulation can further comprise one or more exemplary fillers. Examples of exemplary fillers include cellulose and cellulose derivatives such as microcrystalline cellulose, powdered cellulose; dextrates; starches such as dry starch, hydrolyzed starch, and starch derivatives such as corn starch; cyclodextrin; sugars such as powdered sugar and sugar alcohols such as lactose, mannitol, sucrose and sorbitol; inorganic fillers such as aluminum hydroxide gel, calcium carbonate (granules or powder), precipitated calcium carbonate, carbonate, magnesium aluminometasilicate, dibasic calcium phosphate; and sodium chloride, silicon dioxide, silicic acid, titanium dioxide, titanium oxide, dicalcium phosphate dihydrate, calcium sulfate, alumina, kaolin, talc, or combinations thereof. Fillers may be present in the composition from about 20 wt % to about 65 wt %, about 20 wt % to about 50 wt %, about 20 wt % to about 40 wt %, about 45 wt % to about 65 wt %, about 50 wt % to about 65 wt %, or about 55 wt % to about 65 wt % of the total weight of the composition, or any value between these ranges.

In some embodiments of the method described herein, the modified release formulation further comprises one or more disintegrants. Examples of disintegrants include starches, alginic acid, crosslinked polymers such as crosslinked polyvinylpyrrolidone, croscarmellose sodium, potassium starch glycolate, sodium starch glycolate, clays, celluloses, starches, gums, or combinations thereof. Disintegrants may be present in the composition from about 1 wt % to about 10 wt %, about 1 wt % to about 9 wt %, about 1 wt % to about 8 wt %, about 1 wt % to about 7 wt %, about 1 wt % to about 6 wt %, or about 1 wt % to about 5 wt % of the total weight of the composition, or any value between these ranges.

In some embodiments of the method described herein, the modified release formulation further comprises one or more binders, including but not limited to celluloses such as hydroxypropylcellulose, methyl cellulose, and hydroxypropylmethylcellulose; starches such as corn starch, pregelatinized starch, and hydroxypropyl starch; waxes and natural and synthetic gums such as acacia, tragacanth, sodium alginate; synthetic polymers such as polymethacrylates and polyvinylpyrrolidone; and povidone, dextrin, pullulane, agar, gelatin, tragacanth, macrogol, or combinations thereof. Binders may be present in the composition from about 0.5 wt % to about 5 wt %, about 0.5 wt % to about 4 wt %, about 0.5 wt % to about 3 wt %, about 0.5 wt % to about 2 wt %, or about 0.5 wt % to about 1 wt % of the total weight of the composition, or any value between these ranges.

In some embodiments of the method described herein, the modified release formulation further comprises one or more wetting agents, including but not limited to oleic acid, glyceryl monostearate, sorbitan mono-oleate, sorbitan monolaurate, triethanolamine oleate, polyoxyethylene sorbitan mono-oleate, polyoxyethylene sorbitan monolaurate, sodium oleate, sodium lauryl sulfate, poloxamers, poloxamer 188, polyoxyethylene ethers, polyoxyethylene sorbitan fatty acid esters, polyoxyethylene fatty acid esters, polyethylene glycol fatty acid esters, polyoxyethylene hardened castor oil, polyoxyethylene alkyl ethers, polysorbates, cetyl alcohol, glycerol fatty acid esters (for example, triacetin, glycerol monostearate, etc.), polyoxymethylene stearate, sodium lauryl sulfate, sorbitan fatty acid esters, sucrose fatty acid esters, benzalkonium chloride, polyethoxylated castor oil, and combinations thereof. Wetting agents may be present in the composition from about 0.1 wt % to about 1 wt %, about 0.1 wt % to about 2 wt %, about 0.1 wt % to about 3 wt %, about 0.1 wt % to about 4 wt %, or about 0.1 wt % to about 5 wt % of the total weight of the composition, or any value between these ranges.

In some embodiments of the method described herein, the modified release formulation further comprises one or more lubricants, including but not limited to stearic acid, magnesium stearate, calcium hydroxide, talc, corn starch, sodium stearyl fumarate, alkali-metal and alkaline earth metal salts, waxes, boric acid, sodium benzoate, sodium acetate, sodium chloride, leucine, polyethylene glycol (PEG), a methoxypolyethylene glycol, propylene glycol, sodium oleate, glyceryl behenate, glyceryl palmitostearate, glyceryl benzoate, magnesium lauryl sulfate, sodium lauryl sulfate, and combinations thereof. Lubricants may be present in the composition from about 0.1 wt % to about 5 wt %, about 0.1 wt % to about 4 wt %, about 0.1 wt % to about 3 wt %, about 0.1 wt % to about 2 wt %, or about 0.1 wt % to about 1 wt % of the total weight of the composition, or any value between these ranges.

In some embodiments of the method described herein, the modified release formulation further comprises one or more glidants, including but not limited to silica (colloidal anhydrous), starch, talc, magnesium stearate, calcium stearate, zinc stearate, dibasic calcium phosphate, magnesium carbonate, magnesium oxide, calcium silicate, silicon dioxide, silicon dioxide, colloidal silicon dioxide, talc, sodium lauryl sulfate, native starch, or combinations thereof. Glidants may be present in the composition from about 0.05 wt % to about 1 wt %, about 0.05 wt % to about 0.9 wt %, about 0.05 wt % to about 0.8 wt %, about 0.05 wt % to about 0.5 wt %, or about 0.05 wt % to about 0.1 wt % of the total weight of the composition, or any value between these ranges.

In some embodiments of the method described herein, the modified release formulation is a tablet and further comprises a top coat, such as hydroxypropyl-methylcellulose coating or polyvinyl alcohol coating, and are available under the trade name Opadry, such as Opadry White, Opadry II (Opadry is a registered trademark of BPSI Holdings LLC, Wilmington, DE, USA). Top coats may be present in the composition from about 1 wt % to about 10 wt %, about 1 wt % to about 9 wt %, about 1 wt % to about 8 wt %, about 1 wt % to about 7 wt %, about 1 wt % to about 6 wt %, or about 1 wt % to about 5 wt % of the total weight of the composition, or any value between these ranges.

In some embodiments of the method described herein, the modified release formulation can further comprise one or more preservative agents. Examples of preservative agents include sodium benzoate, paraoxybenzoic acid esters, methyl, ethyl, butyl, and propyl parabens, chlorobutanol, benzyl alcohol, phenylethylalcohol, dehydroacetic acid, sorbic acid, benzalkonium chloride (BKC), benzethonium chloride, phenol, phenylmercuric nitrate, thimerosal, or combinations thereof. Preservative agents can be included in the liquid dosage form. The preservative agents can be in an amount sufficient to extend the shelf-life or storage stability, or both, of the liquid dosage form. Preservatives may be present in the composition from about 0.05 wt % to about 1 wt %, about 0.05 wt % to about 0.9 wt %, about 0.05 wt % to about 0.8 wt %, about 0.05 wt % to about 0.5 wt %, or about 0.05 wt % to about 0.1 wt % of the total weight of the composition, or any value between these ranges.

In some embodiments of the method described herein, the modified release formulation can further comprise one or more flavoring agents. Examples of flavoring agents include synthetic flavor oils and flavoring aromatics and/or natural oils, extracts from plants leaves, flowers, fruits, and so forth and the like or any combinations thereof. Additional examples include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil and the like or any combinations thereof. Also useful as flavors are vanilla, citrus oil, including lemon, orange, grape, lime and grapefruit, and fruit essences, including apple, banana, pear, peach, strawberry, raspberry, cherry, plum, pineapple, apricot, strawberry flavor, tutti-fruity flavor, mint flavor, or any combinations thereof. Flavoring agents may be present in the composition from about 0.1 wt % to about 5 wt %, about 0.1 wt % to about 4 wt %, about 0.1 wt % to about 3 wt %, about 0.1 wt % to about 2 wt %, or about 0.1 wt % to about 1 wt % of the total weight of the composition, or any value between these ranges.

In some embodiments of the method described herein, the modified release formulation can generally be in any physical form suitable for use in treating a subject. These forms can be referred to as a unit dosage form, such as an individual pill or tablet. In some examples, the pharmaceutical compositions can be formulated as tablets, capsules, granules, powders, liquids, suspensions, gels, syrups, slurries, suppositories, patches, nasal sprays, aerosols, injectables, implantable sustained-release formulations, or mucoadherent films. In some examples, the pharmaceutical formulation may be formed as a tablet, a bi-layer tablet, a capsule, a multiparticulate, a drug coated sphere, a matrix tablet, or a multicore tablet. A physical form can be selected according to the desired method of treatment.

In some embodiments of the method described herein, the modified release formulation can be manufactured by various conventional methods such as conventional mixing, dissolving, granulating, dragee-making, levigating, emulsifying, encapsulating, entrapping, or lyophilizing processes. Modified release formulations can be formulated in a conventional manner using one or more physiologically acceptable carriers, diluents, excipients or auxiliaries that facilitate processing of the active agent into preparations that can be used pharmaceutically. Proper formulation can be selected upon the oral route of administration chosen.

In some embodiments, the modified release formulation is a core tablet, or a tablet within a tablet, whereby the inner core is used for the slow-drug-release component, and the outside shell contains a rapid-release dose of drug. In some embodiments, the modified release formulation is achieved via microencapsulation whereby microscopic drug particles are encapsulated with a special coating material, such as ethylcellulose. In some embodiments, the modified release formulation is an osmotic drug delivery system in the form of a tablet which contains an outside semipermeable membrane and an inner core filled with a mixture of drug and osmotic agent (salt solution). In some embodiments, the modified release formulation is a gastroretentive system that can remain in the gastric region for several hours and prolong the gastric residence time of a drug. In some embodiments, the modified release formulation is a combination of any of the above-described embodiments.

In some embodiments of the method described herein, for oral administration, the modified release formulation can combine minoxidil or a pharmaceutically acceptable salt thereof with another pharmaceutical agent with one or more pharmaceutically acceptable carriers well known in the art. Such carriers facilitate formulation as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added. For buccal administration, the compositions may take the form of tablets, lozenges, etc. formulated in conventional manner.

In some embodiments of the method described herein, the modified release formulations may comprise a matrix selected from microcrystalline cellulose, sodium carboxymethylcellulose, hydroxyalkylcelluloses such as hydroxy propyl methylcellulose and hydroxypropylcellulose, polyethylene oxide, alkylcelluloses such as methylcellulose and ethylcellulose, polyethylene glycol, polyvinylpyrrolidone, cellulose acetate, cellulose acetate butyrate, cellulose acetate phthalate, cellulose acetate trimellitate, polyvinyl acetate phthalate, polyalkylmethacrylates, polyvinyl acetate and mixtures thereof.

Kit

Embodiments described herein are directed to a kit comprising a slow modified release vehicle comprising an oral pharmaceutical formulation comprising minoxidil or a pharmaceutically acceptable salt thereof and an information sheet.

In some embodiments of the kit described herein, the oral pharmaceutical formulation comprises minoxidil or a pharmaceutically acceptable salt thereof, a release modifier, a filler, a glidant, a lubricant, and combinations thereof.

In some embodiments, the kit described herein comprises minoxidil or a pharmaceutically acceptable salt thereof in an amount of about 0.075% to about 33% (w/w) of the total formulation. In some embodiments, the kit described herein comprises minoxidil or a pharmaceutically acceptable salt thereof in an amount of about 0.083% to about 33% (w/w) of the total formulation. In some embodiments of the kit described herein, the oral pharmaceutical formulation comprises minoxidil or a pharmaceutically acceptable salt thereof in an amount of about 0.1% to about 20% (w/w) of the total formulation. In some embodiments, the kit comprises an oral pharmaceutical formulation comprising minoxidil or a pharmaceutically acceptable salt thereof in an amount of about 1% to about 10% (w/w) of the total formulation. In some embodiments, the kit comprises minoxidil or a pharmaceutically acceptable salt thereof in an amount of about 1% to about 5% (w/w) of the total formulation. In some embodiments, the kit comprises minoxidil or a pharmaceutically acceptable salt thereof in an amount of about 1% to about 1.5% (w/w) of the total formulation. In some embodiment, the kit comprises an oral pharmaceutical formulation comprising minoxidil or a pharmaceutically acceptable salt thereof in an amount (w/w) of about 0.075%, about 0.1%, about 0.25%, about 0.5%, about 0.75%, about 1%, about 1.5%, about 2%, about 2.5%, about 3%, about 3.5%, about 4%, about 5%, about 6%, about 7%, about 8%, about 9%, about 10%, about 12%, about 14%, about 15%, about 16%, about 18%, about 20%, about 25%, about 30%, about 33%, or any range within these values.

In some embodiments of the kit described herein, the oral pharmaceutical formulation comprises a release modifier in an amount of about 20% to about 95% (w/w) of the total formulation. In some embodiments, the kit comprises an oral pharmaceutical formulation comprising a release modifier in an amount of about 50% to about 80% (w/w) of the total formulation. In some embodiments, the kit comprises an oral pharmaceutical formulation comprising a release modifier in an amount (w/w) of about 20%, about 25%, about 30%, about 40%, about 45%, about 50%, about 55%, about 60%, about 65%, about 70%, about 75%, about 80%, about 85%, about 90%, about 95%, or any range within these values.

In some embodiments of the kit described herein, the oral pharmaceutical formulation comprises a glidant in an amount of about 0.01% to about 2% (w/w) of the total formulation. In some embodiments, the kit comprises an oral pharmaceutical formulation comprising a glidant in an amount of about 0.1% to about 0.3% (w/w) of the total formulation. In some embodiments, the kit comprises an oral pharmaceutical formulation comprising a glidant in an amount (w/w) of about 0.01%, about 0.02%, about 0.03%, about 0.04%, about 0.05%, about 0.06%, about 0.07%, about 0.08%, about 0.09%, about 0.1%, about 0.15%, about 0.2%, about 0.25%, about 0.35%, or any range within these values.

In some embodiments of the kit described herein, the oral pharmaceutical formulation comprises a lubricant in an amount of about 0.1% to about 1% (w/w) of the total formulation. In some embodiments, the kit comprises an oral pharmaceutical formulation comprising a lubricant in an amount of about 0.4% to about 0.6% (w/w) of the total formulation. In some embodiments, the kit comprises an oral pharmaceutical formulation comprising a lubricant in an amount (w/w) of about 0.1%, about 0.2%, about 0.3%, about 0.4%, about 0.5%, about 0.6%, about 0.7%, about 0.8%, about 0.9%, about 1%, or any range within these values.

In some embodiments of the kit described herein, the release modifier is hydroxy propyl methylcellulose (HPMC) or lactose monohydrate. In some embodiments, the hydroxypropyl methylcellulose is HPMC K4M or HPMC K200M. In some embodiments, the HPMC K4M is in an amount of 0 mg to about 45 mg in a 150 mg formulation. In some embodiments, the HPMC K4M is 0% to about 30% (w/w) of the total formulation. In some embodiments, the HPMC K200M is in an amount of 0 mg to about 120 mg in a 150 mg formulation. In some embodiments, the HPMC K200M is about 0% to about 80% (w/w) of the total formulation. In some embodiments, the lactose monohydrate is in an amount of about 0 mg to about 55 mg in a 150 mg formulation. In some embodiments, the lactose monohydrate is about 0 to about 40% (w/w) of the total formulation.

In some embodiments of the kit described herein, the filler is microcrystalline cellulose, talc, calcium carbonate (e.g., granules or powder), powdered cellulose, dextrates, kaolin, mannitol, silicic acid, sorbitol, starch, pre-gelatinized starch, and mixtures thereof. In some embodiments, the filler is in an amount of about of about 25 mg to about 55 mg in a 150 mg formulation. In some embodiments, the microcrystalline cellulose is about 15% to about 40% (w/w) of the total formulation.

In some embodiments, the glidant is silica (colloidal anhydrous), starch, talc, magnesium stearate, calcium stearate, zinc stearate, dibasic calcium phosphate, magnesium carbonate, magnesium oxide, calcium silicate, silicon dioxide, silicon dioxide, colloidal silicon dioxide, talc, sodium lauryl sulfate, native starch, or combinations thereof. In some embodiments of the kit described herein, the glidant is silica. In some embodiments the silica is colloidal anhydrous. In some embodiments, the glidant is in an amount of about 0.3 mg to about 5 mg in a 150 mg formulation. In some embodiments, the glidant is about 0.001% to about 0.04% (w/w) of the total formulation.

In some embodiments of the kit described herein, the lubricant is magnesium stearate, calcium stearate, zinc stearate, stearic acid, hydrogenated vegetable oils, sterotex, polyoxyethylene, monostearate, talc, polyethyleneglycol, sodium benzoate, sodium lauryl sulfate, magnesium lauryl sulfate, light mineral oil, or combinations thereof. In some embodiments, the lubricant is in an amount of about 0.75 mg to about 1.5 mg in a 150 mg formulation. In some embodiments, the lubricant is about 0.005% to about 0.01% (w/w) of the total formulation.

In some embodiments of the kit described herein, the slow modified release vehicle further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof. In some embodiments, the slow modified release vehicle further comprises medrogestone, cetirizine, setipiprant, valproic acid, and combinations thereof.

In any embodiment of the kit described herein, the non-steroid anti-androgen is selected from flutamide, clascoterone, bicalutamide, pyrilutamide, enzualutamide, nilutamide, apalutamide, proxilutamide, cimetidine, topalutamide, and combinations thereof. In any embodiment, the 17α-hydroxyprogesterone derivative is selected from chlormadinone acetate, cyproterone acetate, megestrol acetate, osaterone acetate, and combinations thereof. In any embodiment, the 19-norprogesterone derivative is nomegestrol acetate. In any embodiment, 19-nortestosterone derivative is selected from dienogest, oxendolone, and combinations thereof. In any embodiment, the 17α-spirolactone derivative is selected from drospirenone, spironolactone, and combinations thereof. In any embodiment, the 5-alpha reductase inhibitor is selected from alfatradiol, dutasteride, epristeride, finasteride, saw palmetto extract, bexlosteride, izonsteride, epigallocatechin, fluridil, and combinations thereof. In any embodiment, the estrogen is selected from estradiol, estradiol esters, ethinylestradiol, conjugated estrogens, diethylstilbestrol, and combinations thereof. In any embodiment, the GnRH analog is a GnRH agonist wherein the GnRH agonist is selected from goserelin, buserelin, leuprorelin, and combinations thereof. In any embodiment, the GnRH analog is a GnRH antagonist wherein the GnRH antagonist is cetrorelix. In any embodiment, the prostaglandin F2α analog is latanoprost, travoprost, tafluprost, unoprostone, dinoprost, AS604872, BOL303259X, PF3187207, carboprost, and combinations thereof. In any embodiment, the prostamide is bimatoprost. In any embodiment, the prostanoid receptor agonist is fluprostenol, cicaprost, and combinations thereof. In any embodiment, the prostaglandin D2 receptor antagonist is laropiprant, AM211, and combinations thereof. In any embodiment, the prostaglandin E2 analog is sulprostone. In any embodiment, the EP2 receptor agonist is butaprost, diazoxide, kopexil, pinacidil, ET-02, and combinations thereof. In any embodiment, the JAK inhibitor is abrocitinib, baricitinib, brepocitinib, decernotinib, delgocitinib, deuruxolitinib, deucravacitinib, fedratinib, filgotinib, gusacitinib, itacitinib, oclacitinib, pacritinib, peficitinib, ritlecitnib, ruxolitinib, tofacitinib, upadacitinib, SHR0302, ATI-2138, jacktinib, and combinations thereof. In any embodiment, the alopecia areata medication is selected from etrasimod, fingolimod, ozanimod, siponimod, ponesimod, and combinations thereof. In any embodiment, the supplement is selected from biotin, zinc, selenium, caffeine, sodium chloride, marine collagen, and combinations thereof.

In some embodiments of the kit described herein, the kit comprises an information sheet. In some embodiments, the information sheet comprises instructions for selecting an oral dosage form based on a body weight of a patient. In some embodiment, the information sheet comprises instructions for selecting a daily dose of minoxidil or a pharmaceutically acceptable salt thereof.

In some embodiments of the kit described herein, the information sheet comprises a warning of adverse effects. In some embodiments, the adverse effects are selected from peripheral edema and hirsutism.

In some embodiments of the kit described herein, the minoxidil or a pharmaceutically acceptable salt thereof is administered only once daily. In some embodiments, the minoxidil or a pharmaceutically acceptable salt thereof is administered at least once daily. In some embodiments, the minoxidil or a pharmaceutically acceptable salt thereof is administered four times per day. In some embodiments, the minoxidil or a pharmaceutically acceptable salt thereof is administered three times per day. In some embodiments, the minoxidil or a pharmaceutically acceptable salt thereof is administered two times per day.

In some embodiments of the kit described herein, the slow modified release vehicle releases about 50% to about 98% of the daily dose of minoxidil or a pharmaceutically acceptable salt thereof within about 12 hours after the oral administration. In some embodiments of the pharmaceutical formulation described herein, the extended release formulation releases about 50% to about 98% of the daily dose of minoxidil or a pharmaceutically acceptable salt thereof within about 18 hours after the oral administration. In some embodiments described herein, the slow modified release vehicle releases about 50%, about 55%, about 60%, about 65%, about 70%, about 75%, about 80%, about 85%, about 90%, about 95%, about 98% of the daily dose of minoxidil or a pharmaceutically acceptable salt thereof within about 18 hours after the oral administration, or any range within these values.

In some embodiments of the kit described herein, the oral pharmaceutical formulation comprising exhibits a dissolution profile wherein about 25% of the formulation dissolves in in a neutral pH solution in less than about 2 hours or less than about 4 hours. In some embodiments, about 25% of the pharmaceutical formulation dissolves in a neutral pH solution at about 0.5 hours, about 0.75 hours, about, 1 hour, about 1.5 hours, about 2 hours, about 2.5 hours, about 3 hours, or about 4 hours.

In some embodiments of the kit described herein, the oral pharmaceutical formulation comprising exhibits a dissolution profile wherein about 50% of the pharmaceutical formulation dissolves in a neutral pH solution in less than about 2 hours, less than about 6 hours, or less than about 12 hours. In some embodiments, about 50% of the pharmaceutical formulation dissolves in a neutral pH solution at about 1 hour, about 1.5 hours, about 2 hours, about 3 hours, about 4 hours, about 6 hours, about 8 hours, or about 10 hours.

In some embodiments of the kit described herein, the oral pharmaceutical formulation exhibits a dissolution profile wherein about 75% of the pharmaceutical formulation dissolves in a neutral pH solution in less than about 4 hours, less than about 8 hours, less than about 12 hours, or less than about 18 hours. In some embodiments, about 75% of the pharmaceutical formulation dissolves in a neutral pH solution at about 3 hours, about 3.5 hours, about 4 hours, about 4.5 hours, about 5 hours, about 6 hours, about 8 hours, about 10 hours, about 12 hours, about 14 hours, or about 16 hours.

In some embodiments of the kit described herein, the oral pharmaceutical formulation exhibits a dissolution profile wherein about 100% of the pharmaceutical formulation dissolves in a neutral pH in less than about 12 hours, less than about 24 hours, or less than about 48 hours. In some embodiments, about 100% of the pharmaceutical formulation dissolves in a neutral pH at about 10 hours, about 12 hours, about 14 hours, about 16 hours, about 18 hours, about 20 hours, about 22 hours, about 24 hours, about 26 hours, or about 28 hours.

In some embodiments of the kit described herein, the oral pharmaceutical formulation exhibits a zero order release of minoxidil or a pharmaceutically acceptable salt thereof, a pseudo zero order release of minoxidil or a pharmaceutically acceptable salt thereof, a first order release of minoxidil or a pharmaceutically acceptable salt thereof, a pseudo first order release of minoxidil or a pharmaceutically acceptable salt thereof, or a second order release of minoxidil or a pharmaceutically acceptable salt thereof.

In some embodiments of the kit described herein, the minoxidil or a pharmaceutically acceptable salt thereof is in a therapeutically effective amount. In some embodiments, the one or more active agents are in a therapeutically effective amount. In some embodiments, the pharmaceutical formulation comprises minoxidil or a pharmaceutically acceptable salt thereof in a subtherapeutic amount. In some embodiments, the pharmaceutical formulation comprises one or more active agents in a subtherapeutic amount. In some embodiments, the pharmaceutical formulation comprises minoxidil or a pharmaceutically acceptable salt thereof and one or more active agents wherein the minoxidil or a pharmaceutically acceptable salt thereof and the one or more active agents are each in subtherapeutic amounts.

In some embodiments of the kit described herein, the daily dose of minoxidil or a pharmaceutically acceptable salt thereof is about 25% to about 500% of the amount of the immediate-release oral minoxidil or a pharmaceutically acceptable salt thereof used to treat hypertension. In some embodiments, the daily dose of minoxidil or a pharmaceutically acceptable salt thereof is about 10% to about 90% of the amount of the immediate-release oral minoxidil or a pharmaceutically acceptable salt thereof used to treat hypertension. In some embodiments, the daily dose of minoxidil or a pharmaceutically acceptable salt thereof is about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 125%, about 150%, about 175%, about 200%, about 225%, about 250%, about 275%, about 300%, about 325%, about 350%, about 375%, about 400%, about 425%, about 450%, about 475%, about 500% of the amount of the immediate-release oral minoxidil or a pharmaceutically acceptable salt thereof used to treat hypertension, or any range within these values.

In some embodiments of the kit described herein, the daily dose of minoxidil or a pharmaceutically acceptable salt thereof is in an amount of about 0.25 mg to about 50 mg. In some embodiments, the daily dose of minoxidil or a pharmaceutically acceptable salt thereof is in an amount of about 0.5 mg to about 2.5 mg. In some embodiments, the daily dose of minoxidil or a pharmaceutically acceptable salt thereof is in an amount of about 0.625 mg to about 7.5 mg. In some embodiments, the daily dose of minoxidil or a pharmaceutically acceptable salt thereof is in an amount of about 0.5 mg to about 10 mg. In some embodiments, the daily dose of minoxidil or a pharmaceutically acceptable salt thereof is about 0.25 mg to about 20 mg. In some embodiments, the daily dose of minoxidil or a pharmaceutically acceptable salt thereof is in an amount of about 0.125 mg to about 100 mg. In some embodiments, the daily dose of minoxidil or a pharmaceutically acceptable salt thereof is about 2.5 mg. In some embodiments, the daily dose of minoxidil or a pharmaceutically acceptable salt thereof is in an amount of about 0.125 mg, about 0.25 mg, about 5 mg, about 0.625 mg, about 0.75 mg, about 1 mg, about 1.25 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 9 mg, about 10 mg, about 12 mg, about 15 mg, about 18 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, or any range within these values.

In some embodiments of the kit described herein, the daily dose of minoxidil or a pharmaceutically acceptable salt thereof is administered to a subject in an amount of about 0.000625 mg/kg/day to about 1.25 mg/kg/day. In some embodiments of the kit described herein, the daily dose of minoxidil or a pharmaceutically acceptable salt thereof is administered to a subject in an amount of about 0.00625 mg/kg/day to about 0.5 mg/kg/day. In some embodiments, the daily dose of the minoxidil or a pharmaceutically acceptable salt thereof is about 0.00625 mg/kg/day to about 0.375 mg/kg/day. In some embodiments, the daily dose of the minoxidil or a pharmaceutically acceptable salt thereof is about 0.000625 mg/kg/day; about 0.00125 mg/kg/day, about 0.0025 mg/kg/day, about 0.00375 mg/kg/day, about 0.005 mg/kg/day, about 0.00625 mg/kg/day, about 0.0125 mg/kg/day, about 0.025 mg/kg/day, about 0.0375 mg/kg/day, about 0.05 mg/kg/day, about 0.0625 mg/kg/day, about 0.075 mg/kg/day, about 0.0875 mg/kg/day, about 0.1 mg/kg/day, about 0.125 mg/kg/day, about 0.25 mg/kg/day, about 0.5 mg/kg/day, about 0.625 mg/kg/day, about 0.75 mg/kg/day, about 1 mg/kg/day, or any range within these values.

In some embodiments of the method described herein, the daily dose of minoxidil or a pharmaceutically acceptable salt thereof is in an amount of about 0.625 mg four times per day.

In some embodiments of the kit described herein, the oral administration of the daily dose minoxidil or a pharmaceutically acceptable salt thereof results in a Cmax of about 0.25 ng/ml to about 20 ng/ml. In some embodiments, the oral administration of the daily dose minoxidil or a pharmaceutically acceptable salt thereof results in a Cmax that is devoid of cardiac effects.

In some embodiments of the kit described herein, the oral administration results in a half-life or effective half-life of the daily dose of minoxidil or a pharmaceutically acceptable salt thereof of about 1 hour to about 24 hours. In some embodiments, the oral administration results in a half-life or effective half-life of the daily dose of minoxidil or a pharmaceutically acceptable salt thereof of about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, about 24 hours, or any range within these values.

In some embodiments of the kit described herein, the oral administration of the daily dose of minoxidil or a pharmaceutically acceptable salt thereof results in a Tmax of about 30 to about 360 minutes. In some embodiments, the oral administration of the daily dose of minoxidil or a pharmaceutically acceptable salt thereof results in a delayed release that results in a Tmax between both 30 to 360 minutes and between 390 minutes and 1080 minutes.

In some embodiments of the kit described herein, the oral administration of the daily dose of modified release minoxidil or a pharmaceutically acceptable salt thereof results in an AUC that is greater than an equivalent dose of an immediate release formulation. In some embodiments of the kit described herein, the oral administration of the daily dose of the modified release minoxidil or a pharmaceutically acceptable salt thereof results in an AUC that is less than an equivalent dose of immediate release formulation. In some embodiments of the kit described herein, the oral administration of the daily dose of the modified release minoxidil or a pharmaceutically acceptable salt thereof results in an AUC that is equal to an equivalent dose of immediate release formulation.

In some embodiments of the kit described herein, the slow modified release vehicle is an inert solid vehicle, or matrix, in which a drug is uniformly suspended, including in the form of tablets or small beads. In some embodiments, the matrix is a gelling material including gelatin, methylcellulose, gum tragacanth, Veegum, and alginic acid. In some embodiments, the matrix is a polymer including polylactic acid copolymer, polyacrylate, methacrylate, polyester, ethylene-vinyl acetate copolymer (EVA), polyglycolide, polylactide, and silicone. In some embodiments, the slow modified release vehicle is a slow-release pellet, bead, or granule. In some embodiments, the modified release formulation is an extended release tablet where the solubility of a drug is modified for extended release. In some embodiments, the extended release tablet is formed by using the nonionized base or acid form of the drug. In some embodiments, the extended release tabled is formed by granulating the drug with excipients (including stearic acid, castor wax, high-molecular-weight polyethylene glycol (Carbowax), glyceryl monosterate, white wax, spermaceti oil, magnesium stearate and hydrogenated vegetable oil (Sterotex)) to decrease the aqueous solubility of the drug. In some embodiments, the slow modified release vehicle is an ion-exchange preparation whereby an anionic or cationic drug is complexed with an oppositely charged ionic resin to form an insoluble nonabsorbable resin-drug complex.

In some embodiments of the kit described herein, the slow modified release vehicle further comprises one or more pharmaceutically acceptable excipients. Examples of pharmaceutically acceptable excipients that may be present in the composition include but are not limited to fillers/vehicles, solvents/co-solvents, preservatives, antioxidants, suspending agents, surfactants, antifoaming agents, buffering agents, chelating agents, sweeteners, flavoring agents, binders, extenders, disintegrants, diluents, lubricants, fillers, wetting agents, glidants, and combinations thereof.

In some embodiments of the kit described herein, the slow modified release vehicle can further comprise one or more exemplary fillers. Examples of exemplary fillers include cellulose and cellulose derivatives such as microcrystalline cellulose; powdered cellulose; dextrates; starches such as dry starch, hydrolyzed starch, and starch derivatives such as corn starch; cyclodextrin; sugars such as powdered sugar and sugar alcohols such as lactose, mannitol, sucrose and sorbitol; inorganic fillers such as aluminum hydroxide gel, calcium carbonate (granule or powder), precipitated calcium carbonate, carbonate, magnesium aluminometasilicate, dibasic calcium phosphate; and sodium chloride, silicon dioxide, silicic acid, titanium dioxide, titanium oxide, dicalcium phosphate dihydrate, calcium sulfate, alumina, kaolin, talc, or combinations thereof. Fillers may be present in the composition from about 20 wt % to about 65 wt %, about 20 wt % to about 50 wt %, about 20 wt % to about 40 wt %, about 45 wt % to about 65 wt %, about 50 wt % to about 65 wt %, or about 55 wt % to about 65 wt % of the total weight of the composition, or any value between these ranges.

In some embodiments of the kit described herein, the slow modified release vehicle further comprises one or more disintegrants. Examples of disintegrants include starches, alginic acid, crosslinked polymers such as crosslinked polyvinylpyrrolidone, croscarmellose sodium, potassium starch glycolate, sodium starch glycolate, clays, celluloses, starches, gums, or combinations thereof. Disintegrants may be present in the composition from about 1 wt % to about 10 wt %, about 1 wt % to about 9 wt %, about 1 wt % to about 8 wt %, about 1 wt % to about 7 wt %, about 1 wt % to about 6 wt %, or about 1 wt % to about 5 wt % of the total weight of the composition, or any value between these ranges.

In some embodiments of the kit described herein, the slow modified release vehicle further comprises one or more binders, including but not limited to celluloses such as hydroxypropylcellulose, methyl cellulose, and hydroxypropylmethylcellulose; starches such as corn starch, pregelatinized starch, and hydroxypropyl starch; waxes and natural and synthetic gums such as acacia, tragacanth, sodium alginate; synthetic polymers such as polymethacrylates and polyvinylpyrrolidone; and povidone, dextrin, pullulane, agar, gelatin, tragacanth, macrogol, or combinations thereof. Binders may be present in the composition from about 0.5 wt % to about 5 wt %, about 0.5 wt % to about 4 wt %, about 0.5 wt % to about 3 wt %, about 0.5 wt % to about 2 wt %, or about 0.5 wt % to about 1 wt % of the total weight of the composition, or any value between these ranges.

In some embodiments of the kit described herein, slow modified release vehicle further comprises one or more wetting agents, including but not limited to oleic acid, glyceryl monostearate, sorbitan mono-oleate, sorbitan monolaurate, triethanolamine oleate, polyoxyethylene sorbitan mono-oleate, polyoxyethylene sorbitan monolaurate, sodium oleate, sodium lauryl sulfate, poloxamers, poloxamer 188, polyoxyethylene ethers, polyoxyethylene sorbitan fatty acid esters, polyoxyethylene fatty acid esters, polyethylene glycol fatty acid esters, polyoxyethylene hardened castor oil, polyoxyethylene alkyl ethers, polysorbates, cetyl alcohol, glycerol fatty acid esters (for example, triacetin, glycerol monostearate, etc.), polyoxymethylene stearate, sodium lauryl sulfate, sorbitan fatty acid esters, sucrose fatty acid esters, benzalkonium chloride, polyethoxylated castor oil, and combinations thereof. Wetting agents may be present in the composition from about 0.1 wt % to about 1 wt %, about 0.1 wt % to about 2 wt %, about 0.1 wt % to about 3 wt %, about 0.1 wt % to about 4 wt %, or about 0.1 wt % to about 5 wt % of the total weight of the composition, or any value between these ranges.

In some embodiments of the kit described herein, the slow modified release vehicle further comprises one or more lubricants, including but not limited to stearic acid, magnesium stearate, calcium hydroxide, talc, corn starch, sodium stearyl fumarate, alkali-metal and alkaline earth metal salts, waxes, boric acid, sodium benzoate, sodium acetate, sodium chloride, leucine, polyethylene glycol (PEG), a methoxypolyethylene glycol, propylene glycol, sodium oleate, glyceryl behenate, glyceryl palmitostearate, glyceryl benzoate, magnesium lauryl sulfate, sodium lauryl sulfate, and combinations thereof. Lubricants may be present in the composition from about 0.1 wt % to about 5 wt %, about 0.1 wt % to about 4 wt %, about 0.1 wt % to about 3 wt %, about 0.1 wt % to about 2 wt %, or about 0.1 wt % to about 1 wt % of the total weight of the composition, or any value between these ranges.

In some embodiments of the kit described herein, slow modified release vehicle further comprises one or more glidants, including but not limited to colloidal silicon dioxide, talc, sodium lauryl sulfate, native starch, and combinations thereof. Glidants may be present in the composition from about 0.05 wt % to about 1 wt %, about 0.05 wt % to about 0.9 wt %, about 0.05 wt % to about 0.8 wt %, about 0.05 wt % to about 0.5 wt %, or about 0.05 wt % to about 0.1 wt % of the total weight of the composition, or any value between these ranges.

In some embodiments of the kit described herein, the slow modified release vehicle is a tablet and further comprises a top coat, such as hydroxypropyl-methylcellulose coating or polyvinyl alcohol coating, and are available under the trade name Opadry, such as Opadry White, Opadry II (Opadry is a registered trademark of BPSI Holdings LLC, Wilmington, DE, USA). Top coats may be present in the composition from about 1 wt % to about 10 wt %, about 1 wt % to about 9 wt %, about 1 wt % to about 8 wt %, about 1 wt % to about 7 wt %, about 1 wt % to about 6 wt %, or about 1 wt % to about 5 wt % of the total weight of the composition, or any value between these ranges.

In some embodiments of the kit described herein, the slow modified release vehicle can further comprise one or more preservative agents. Examples of preservative agents include sodium benzoate, paraoxybenzoic acid esters, methyl, ethyl, butyl, and propyl parabens, chlorobutanol, benzyl alcohol, phenylethylalcohol, dehydroacetic acid, sorbic acid, benzalkonium chloride (BKC), benzethonium chloride, phenol, phenylmercuric nitrate, thimerosal, or combinations thereof. Preservative agents can be included in the liquid dosage form. The preservative agents can be in an amount sufficient to extend the shelf-life or storage stability, or both, of the liquid dosage form. Preservatives may be present in the composition from about 0.05 wt % to about 1 wt %, about 0.05 wt % to about 0.9 wt %, about 0.05 wt % to about 0.8 wt %, about 0.05 wt % to about 0.5 wt %, or about 0.05 wt % to about 0.1 wt % of the total weight of the composition, or any value between these ranges.

In some embodiments of the kit described herein, the slow modified release vehicle can further comprise one or more flavoring agents. Examples of flavoring agents include synthetic flavor oils and flavoring aromatics and/or natural oils, extracts from plants leaves, flowers, fruits, and so forth and the like or any combinations thereof. Additional examples include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil and the like or any combinations thereof. Also useful as flavors are vanilla, citrus oil, including lemon, orange, grape, lime and grapefruit, and fruit essences, including apple, banana, pear, peach, strawberry, raspberry, cherry, plum, pineapple, apricot, strawberry flavor, tutti-fruity flavor, mint flavor, or any combinations thereof. Flavoring agents may be present in the composition from about 0.1 wt % to about 5 wt %, about 0.1 wt % to about 4 wt %, about 0.1 wt % to about 3 wt %, about 0.1 wt % to about 2 wt %, or about 0.1 wt % to about 1 wt % of the total weight of the composition, or any value between these ranges.

In some embodiments of the kit described herein, the slow modified release vehicle can generally be in any physical form suitable for use in treating a subject. These forms can be referred to as a unit dosage form, such as an individual pill or tablet. In some examples, the pharmaceutical compositions can be formulated as tablets, capsules, granules, powders, liquids, suspensions, gels, syrups, slurries, suppositories, patches, nasal sprays, aerosols, injectables, implantable sustained-release formulations, or mucoadherent films. In some examples, the pharmaceutical formulation may be formed as a tablet, a bi-layer tablet, a capsule, a multiparticulate, a drug coated sphere, a matrix tablet, or a multicore tablet. A physical form can be selected according to the desired method of treatment.

In some embodiments of the kit described herein, the slow modified release vehicle can be manufactured by various conventional methods such as conventional mixing, dissolving, granulating, dragee-making, levigating, emulsifying, encapsulating, entrapping, or lyophilizing processes. Slow modified release vehicles can be formulated in a conventional manner using one or more physiologically acceptable carriers, diluents, excipients or auxiliaries that facilitate processing of the active agent into preparations that can be used pharmaceutically. Proper formulation can be selected upon the oral route of administration chosen.

In some embodiments, the slow modified release vehicle is a core tablet, or a tablet within a tablet, whereby the inner core is used for the slow-drug-release component, and the outside shell contains a rapid-release dose of drug. In some embodiments, the slow modified release vehicle is achieved via microencapsulation whereby microscopic drug particles are encapsulated with a special coating material, such as ethylcellulose. In some embodiments, the slow modified release vehicle is an osmotic drug delivery system in the form of a tablet which contains an outside semipermeable membrane and an inner core filled with a mixture of drug and osmotic agent (salt solution). In some embodiments, the slow modified release vehicle is a gastroretentive system that can remain in the gastric region for several hours and prolong the gastric residence time of a drug. In some embodiments, the slow modified release vehicle is a combination of any of the above-described embodiments.

In some embodiments of the pharmaceutical formulation described herein, the pharmaceutical formulation is a tablet. In some embodiments, the tablet is a sustained release or controlled release tablet. The sustained release or controlled release tablet may be an osmotic pump type controlled release tablet, a matrix type controlled release tablet or a sustained and controlled release tablet based on sustained release pellets. Among them, the osmotic pump type controlled release tablets include osmotic pump controlled release tablets and osmotic pump immediate and sustained double-release tablets, and the matrix type controlled release tablets include matrix type sustained release tablets, matrix type immediate and sustained double-release double layer tablets and matrix type immediate and sustained double-release coated tablets, etc. The sustained and controlled release tablets based on sustained release pellets include sustained release tablets based on sustained release pellets, and immediate and sustained double-release tablets based on sustained release pellets and immediate release pellets. The sustained and controlled release tablet described above can specifically achieve the drug release behavior of the present invention in the following manners: osmotic pump type controlled release tablets, matrix type controlled release tablets, or sustained release tablets based on sustained release pellets.

The osmotic pump controlled release tablet of the invention may be a single layer osmotic pump tablet, a single layer osmotic pump immediate and sustained double-release tablet, a double layer osmotic pump controlled release tablet or a double layer osmotic pump immediate and sustained double release tablet. The double-layer osmotic pump controlled release tablet of the invention mainly comprises: 1) a controlled release drug layer, which is formed by a controlled release drug layer composition, located in a rigid film shell and adjacent to the drug release pore; 2) a push layer (also referred to as a boost layer), which is formed by a push layer composition, located in a rigid film shell, and away from the side of the drug release pore; 3) an optional seal coat layer located between the inner surface of the rigid film shell and the core composed of the drug layer and the push layer, and prepared from the seal coating composition by drying; 4) a rigid film shell having moisture permeability, which is obtained by drying a controlled release coating solution and has one or more drug release pores at one end of the film shell; 5) an optional non-limiting aesthetic outer coat; 6) an optional non-limiting immediate release drug layer formed by an immediate release drug composition, located outside the rigid film shell/or the optional aesthetic outer coat. Further description of the controlled release formulations can be found in U.S. Publication No. 20200108008, which is incorporated herein by reference in its entirety.

The matrix type controlled release tablets of the present invention can have an immediate and sustained double release behavior. The controlled release matrix type tablet of the invention mainly consists of a sustained release phase and an optional immediate release phase. The double-layer tablet composed of the sustained release phase and immediate release phase is an immediate and sustained double release matrix type tablet, and the single-layer tablet composed only of the sustained release phase is an ordinary sustained release matrix type tablet. The sustained release phase comprises 100 to 900 parts by weight, preferably 150 to 700 parts by weight, more preferably 200 to 600 parts by weight, of the minoxidil or pharmaceutically acceptable salt thereof in an improved dissolution form, 10 to 300 parts by weight, preferably 30 to 150 parts by weight of a release rate adjusting matrix polymer, 0 to 50 parts by weight of a diluent, and 0.2 to 30 parts by weight, preferably 1 to 30 parts by weight, of other common additives for tablets. The sustained release phase was prepared by thoroughly mixing the components and pressing through common methods well known for those skilled in the art. The release rate adjusting matrix polymer may be one or a combination of two or more selected from the group consisting of polyoxyethylene, hydroxypropyl cellulose, hypromellose, methyl cellulose, hydroxyethyl cellulose, ethyl cellulose, sodium alginate, povidone, copolyvidone, acrylic resin, carbomer; preferably one or a combination of two or more selected from the group consisting of hydroxypropylcellulose, sodium alginate, hypromellose, and carbomer.

The sustained release tablets based on sustained release pellets of the present invention can be a sustained release tablet based on sustained release pellets, or an immediate and sustained double release tablet based on an immediate release matrix/sustained release pellets.

In some embodiments of the pharmaceutical formulation described herein, the pharmaceutical formulation is a capsule. In some embodiments, the capsule is a controlled release capsule preparation which is selected from the group consisting of a pellet-based sustained and controlled release capsule and a tablet-based sustained and controlled release capsule. In some embodiments, the capsule is a microtablet based controlled release capsule. The pellet-based sustained and controlled release capsule of the present invention is a controlled release capsule composed of sustained release pellets, or an immediate and sustained double release capsule composed of sustained release pellets and immediate release pellets, and may include capsules containing matrix type sustained release pellets, capsules containing coated sustained release pellets, capsules containing sustained release pellets having immediate release coat, immediate and sustained double-release capsules containing immediate release pellets and matrix type sustained release pellets, and immediate and sustained double-release capsules containing immediate release pellets and coated sustained release pellets.

The microtablet based sustained and controlled release capsules of the invention is controlled release capsules composed of sustained release microtablets or immediate and sustained double release capsules composed of sustained release microtablets and immediate release microtablets, and may include capsules containing matrix type sustained release microtablets, capsules containing matrix type sustained release microtablets with immediate release coat, and capsules containing immediate release microtablets and matrix type sustained release microtablets. In general, for the filling of hard capsules, the produced microtablets have a small diameter of typically <5 mm.

In some embodiments of the pharmaceutical formulation described herein, the pharmaceutical formulation further comprises an enteric coating. One or more coatings can comprise an enteric coating, which is a coating on tablets that delays digestion of the tablets until they pass from the stomach into the intestines. Enterically coated formulations bypass the acidic environment of the stomach in order to eliminate the effect of acidic pH on the solubility of minoxidil. Enteric coatings typically comprise pH sensitive polymers. The polymers can be carboxylate and generally interact very little with water at low pH. At a high pH, however, the polymers ionize, thereby causing dissolving of the polymer. Coatings can thus be designed to remain intact in the acidic environment of the stomach, but to dissolve in the more alkaline environment of the intestine. Examples include cellulose acetate phthalate, hydroxypropylmethylethylcellulose succinate, hydroxypropylmethylcellulose phthalate, polyvinyl acetate phthalate, and methacrylic acid-methyl methacrylate copolymer. In one aspect, the first surface coating comprises polyvinyl alcohol. In a further aspect, the first surface coating comprises methacrylic acid-ethyl acrylate copolymer. In a further aspect, the first surface coating comprises polyvinyl alcohol and methacrylic acid-ethyl acrylate copolymer. In a further aspect, the first surface coating is an enteric coating comprising one or more of polyvinyl alcohol or methacrylic acid-ethyl acrylate copolymer. In a further aspect, the first surface coating is an enteric coating comprising one or more of CAP, PVAP, acrylic polymers, acrylic copolymers, HPMCAS, HPMCP, or shellac. Further description of the enteric coating can be found in U.S. Publication No. 20170020920, which is incorporated herein by reference in its entirety.

In some embodiments of the kit described herein, for oral administration, the slow modified release vehicle can combine minoxidil or a pharmaceutically acceptable salt thereof with another pharmaceutical agent with one or more pharmaceutically acceptable carriers well known in the art. Such carriers facilitate formulation as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added. For buccal administration, the compositions may take the form of tablets, lozenges, etc. formulated in conventional manner.

In some embodiments of the kit described herein, the slow modified release vehicles may comprise a matrix selected from microcrystalline cellulose, sodium carboxymethylcellulose, hydroxyalkylcelluloses such as hydroxy propyl methylcellulose and hydroxypropylcellulose, polyethylene oxide, alkylcelluloses such as methylcellulose and ethylcellulose, polyethylene glycol, polyvinylpyrrolidone, cellulose acetate, cellulose acetate butyrate, cellulose acetate phthalate, cellulose acetate trimellitate, polyvinyl acetate phthalate, polyalkylmethacrylates, polyvinyl acetate and mixtures thereof.

FURTHER EMBODIMENTS

Provided herein is embodiment A, a pharmaceutical formulation for oral administration, comprising (preferably a daily dose) of minoxidil or a pharmaceutically acceptable salt thereof, wherein the pharmaceutical formulation is a modified release formulation.

In an embodiment B, the pharmaceutical formulation of embodiment A, wherein the pharmaceutical formulation further comprises a release modifier, a filler, a glidant, a lubricant, and combinations thereof.

In an embodiment C, the pharmaceutical formulation of embodiments A or B, wherein the pharmaceutical formulation comprises about 1% to about 1.5% minoxidil or a pharmaceutically acceptable salt thereof, about 75% to about 85% of a release modifier, about 0.1% to about 0.3% of a glidant, and/or about 0.4% to about 0.6% of a lubricant.

In an embodiment D, the pharmaceutical formulation of according to any preceding embodiment, wherein the pharmaceutical formulation comprises about 1% to about 1.5% minoxidil or a pharmaceutically acceptable salt thereof, about 60% to about 70% of a release modifier, about 0.1% to about 0.3% of a glidant, and/or about 0.4% to about 0.6% of a lubricant.

In an embodiment E, the pharmaceutical formulation of according to any preceding embodiment, wherein the pharmaceutical formulation comprises about 6% to about 7% minoxidil or a pharmaceutically acceptable salt thereof, about 50% to about 60% of a release modifier, about 0.1% to about 0.3% of a glidant, and/or about 0.4% to about 0.6% of a lubricant.

In an embodiment F, the pharmaceutical formulation of according to any preceding embodiment, wherein the pharmaceutical formulation comprises about 6% to about 7% minoxidil or a pharmaceutically acceptable salt thereof, about 65% to about 75% of a release modifier, about 0.1% to about 0.3% of a glidant, and/or about 0.4% to about 0.6% of a lubricant.

In an embodiment G, the pharmaceutical formulation of embodiment B, wherein the release modifier is hydroxypropyl methylcellulose K4M; hydroxypropyl methylcellulose K200M, lactose monohydrate, and combinations thereof.

In an embodiment H, the pharmaceutical formulation of embodiment B, wherein the filler is microcrystalline cellulose. talc, calcium carbonate (e.g., granules or powder), powdered cellulose, dextrates, kaolin, mannitol, silicic acid, sorbitol, starch, pre-gelatinized starch, or combinations thereof.

In an embodiment I, the pharmaceutical formulation of embodiment B, wherein the glidant is silica (colloidal anhydrous), starch, talc, magnesium stearate, calcium stearate, zinc stearate, dibasic calcium phosphate, magnesium carbonate, magnesium oxide, calcium silicate, silicon dioxide, silica aerogels, or combinations thereof.

In an embodiment J, the pharmaceutical formulation of embodiment B, wherein the lubricant is magnesium stearate, calcium stearate, zinc stearate, stearic acid, hydrogenated vegetable oils, sterotex, polyoxyethylene, monostearate, talc, polyethyleneglycol, sodium benzoate, sodium lauryl sulfate, magnesium lauryl sulfate, light mineral oil, or combinations thereof.

In an embodiment K, the pharmaceutical formulation of embodiment A, wherein the pharmaceutical formulation further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof.

In an embodiment L, the pharmaceutical formulation of embodiment A, wherein the pharmaceutical formulation further comprises medrogestone, cetirizine, setipiprant, valproic acid, and combinations thereof.

In an embodiment M, the pharmaceutical formulation of embodiment K, wherein the non-steroid anti-androgen is selected from flutamide, clascoterone, bicalutamide, pyrilutamide, enzualutamide, nilutamide, apalutamide, proxilutamide, cimetidine, topalutamide, and combinations thereof.

In an embodiment N, the pharmaceutical formulation of embodiment K, wherein the 17α-hydroxyprogesterone derivative is selected from chlormadinone acetate, cyproterone acetate, megestrol acetate, osaterone acetate, and combinations thereof.

In an embodiment O, the pharmaceutical formulation of embodiment K, wherein the 19-norprogesterone derivative is nomegestrol acetate.

In an embodiment P, the pharmaceutical formulation of embodiment K, wherein the 19-nortestosterone derivative is selected from dienogest, oxendolone, and combinations thereof.

In an embodiment Q, the pharmaceutical formulation of embodiment K, wherein the 17α-spirolactone derivative is selected from drospirenone, spironolactone, and combinations thereof.

In an embodiment R, the pharmaceutical formulation of embodiment K, wherein the 5-alpha reductase inhibitor is selected from alfatradiol, dutasteride, epristeride, finasteride, saw palmetto extract, bexlosteride, izonsteride, epigallocatechin, fluridil, and combinations thereof.

In an embodiment S, the pharmaceutical formulation of embodiment K, wherein the estrogen is selected from estradiol, estradiol esters, ethinylestradiol, conjugated estrogens, diethylstilbestrol, and combinations thereof.

In an embodiment T, the pharmaceutical formulation of embodiment K, wherein the GnRH analog is a GnRH agonist.

In an embodiment U, the pharmaceutical formulation of embodiment T, wherein the GnRH agonist is selected from goserelin, buserelin, leuprorelin, and combinations thereof.

In an embodiment V, the pharmaceutical formulation of embodiment K, wherein the GnRH analog is a GnRH antagonist.

In an embodiment W, the pharmaceutical formulation of embodiment V, wherein the GnRH antagonist is cetrorelix.

In an embodiment X, the pharmaceutical formulation of embodiment K, wherein the prostaglandin F2α analog is latanoprost, travoprost, tafluprost, unoprostone, dinoprost, AS604872, BOL303259X, PF3187207, carboprost, and combinations thereof.

In an embodiment Y, the pharmaceutical formulation of embodiment K, wherein the prostamide is bimatoprost.

In an embodiment Z, the pharmaceutical formulation of embodiment K, wherein the prostanoid receptor agonist is fluprostenol, cicaprost, and combinations thereof.

In an embodiment AA, the pharmaceutical formulation of embodiment K, wherein the prostaglandin D2 receptor antagonist is laropiprant, AM211, and combinations thereof.

In an embodiment BB, the pharmaceutical formulation of embodiment K, wherein the prostaglandin E2 analog is sulprostone.

In an embodiment CC, the pharmaceutical formulation of embodiment K, wherein the EP2 receptor agonist is butaprost, diazoxide, kopexil, pinacidil, ET-02, and combinations thereof.

In an embodiment DD, the pharmaceutical formulation of embodiment K, wherein the JAK inhibitor is abrocitinib, baricitinib, brepocitinib, decernotinib, delgocitinib, deuruxolitinib, deucravacitinib, fedratinib, filgotinib, gusacitinib, itacitinib, oclacitinib, pacritinib, peficitinib, ritlecitnib, ruxolitinib, tofacitinib, upadacitinib, SHR0302, ATI-2138, jacktinib, and combinations thereof.

In an embodiment EE, the pharmaceutical formulation of embodiment K, wherein the alopecia areata medication is selected from etrasimod, fingolimod, ozanimod, siponimod, ponesimod, and combinations thereof.

In an embodiment FF, the pharmaceutical formulation of embodiment K, wherein the supplement is selected from biotin, zinc, selenium, caffeine, sodium chloride, marine collagen, and combinations thereof.

In an embodiment GG, the pharmaceutical formulation of embodiment A, wherein the modified release formulation is selected from an extended release formulation, a sustained release formulation, a controlled release formulation, or a delayed release formulation.

In an embodiment HH, the pharmaceutical formulation of embodiment A, wherein the daily dose of minoxidil or a pharmaceutically acceptable salt thereof is in an amount of about 0.25 mg to about 50 mg.

In an embodiment II, the pharmaceutical formulation of embodiment A, wherein the oral administration of the daily dose of minoxidil or a pharmaceutically acceptable salt thereof results in a steady state blood level of the minoxidil or a pharmaceutically acceptable salt thereof of about 1 ng/ml to about 20 ng/ml.

In an embodiment JJ, the pharmaceutical formulation of embodiment II, wherein the steady state blood level of the daily dose of minoxidil or a pharmaceutically acceptable salt thereof is maintained for at least about 12 hours.

In an embodiment KK, the pharmaceutical formulation of embodiment A, wherein the oral administration of the daily dose of minoxidil or a pharmaceutically acceptable salt thereof results in a Cmax of about 0.25 ng/ml to about 20 ng/ml.

In an embodiment LL, the pharmaceutical formulation of embodiment A, wherein the oral administration of the daily dose of minoxidil or a pharmaceutically acceptable salt thereof results in a Tmax of about 30 to about 360 minutes.

In an embodiment MM, the pharmaceutical formulation of embodiment A, wherein the daily dose of minoxidil or a pharmaceutically acceptable salt thereof is administered to a subject in an amount of about 0.000625 mg/kg/day to about 1.25 mg/kg/day.

In an embodiment NN, the pharmaceutical formulation of embodiment A, wherein oral administration results in a half-life or effective half-life of the daily dose of minoxidil or a pharmaceutically acceptable salt thereof of about 1 hour to about 24 hours.

In an embodiment OO, the pharmaceutical formulation of embodiment GG, wherein the extended release formulation releases about 50% to about 98% of the daily dose of minoxidil or a pharmaceutically acceptable salt thereof within about 12 hours after the oral administration.

In an embodiment PP, the pharmaceutical formulation of embodiment A, wherein about 25% of the formulation dissolves in a neutral pH solution in less than about 2 hours or less than about 4 hours.

In an embodiment QQ, the pharmaceutical formulation of embodiment A, wherein about 25% of the formulation dissolves in a neutral pH solution at about 0.5 hours, about 0.75 hours, about, 1 hour, about 1.5 hours, about 2 hours, about 2.5 hours, about 3 hours, or about 4 hours.

In an embodiment RR, the pharmaceutical formulation of embodiment A, wherein about 50% of the formulation dissolves in a neutral pH solution in less than about 2 hours, less than about 6 hours, or less than about 12 hours.

In an embodiment SS, the pharmaceutical formulation of embodiment A, wherein about 50% of the formulation dissolves in a neutral pH solution at about 1 hour, about 1.5 hours, about 2 hours, about 3 hours, about 4 hours, about 6 hours, about 8 hours, or about 10 hours.

In an embodiment TT, the pharmaceutical formulation of embodiment A, wherein about 75% of the formulation dissolves in a neutral pH solution in less than about 4 hours, less than about 8 hours, less than about 12 hours, or less than about 18 hours.

In an embodiment UU, the pharmaceutical formulation of embodiment A, wherein about 75% of the formulation dissolves in a neutral pH solution at about 3 hours, about 3.5 hours, about 4 hours, about 4.5 hours, about 5 hours, about 6 hours, about 8 hours, about 10 hours, about 12 hours, about 14 hours, or about 16 hours.

In an embodiment VV, the pharmaceutical formulation of embodiment A, wherein about 100% of the formulation dissolves in a neutral pH in less than about 12 hours, less than about 24 hours, or less than about 48 hours.

In an embodiment WW, the pharmaceutical formulation of embodiment A, wherein about 100% of the formulation dissolves in a neutral pH at about 10 hours, about 12 hours, about 14 hours, about 16 hours, about 18 hours, about 20 hours, about 22 hours, about 24 hours, about 26 hours, or about 28 hours.

In an embodiment XX, the pharmaceutical formulation of embodiment A, wherein the pharmaceutical formulation exhibits a zero order release of the minoxidil or a pharmaceutically acceptable salt thereof, a pseudo zero order release of the minoxidil or a pharmaceutically acceptable salt thereof, a first order release of the minoxidil or a pharmaceutically acceptable salt thereof, a pseudo first order release of the minoxidil or a pharmaceutically acceptable salt thereof, or a second order release of the minoxidil or a pharmaceutically acceptable salt thereof.

In an embodiment YY, the pharmaceutical formulation of embodiment A, wherein the pharmaceutical formulation comprises an enteric coating.

In an embodiment ZZ, the pharmaceutical formulation of embodiment A, wherein the pharmaceutical formulation is administered only once daily.

In an embodiment AAA, the pharmaceutical formulation of embodiment A, wherein the pharmaceutical formulation is administered at least once daily.

In an embodiment BBB, the pharmaceutical formulation of embodiment A, wherein the pharmaceutical formulation is administered four times per day.

In an embodiment CCC, the pharmaceutical formulation of embodiment A, wherein the pharmaceutical formulation is administered three times per day.

In an embodiment DDD, the pharmaceutical formulation of embodiment A, wherein the pharmaceutical formulation is administered two times per day.

Provided herein is embodiment EEE, a pharmaceutical formulation comprising a modified release formulation of minoxidil or a pharmaceutically acceptable salt thereof, wherein the modified release formulation releases about 50% to about 98% of the daily dose of minoxidil or a pharmaceutically acceptable salt thereof within about 12 hours after oral administration.

In an embodiment FFF, the pharmaceutical formulation of embodiment EEE, wherein the pharmaceutical formulation further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof.

In an embodiment GGG, the pharmaceutical formulation of embodiment EEE, wherein the pharmaceutical formulation further comprises medrogestone, cetirizine, setipiprant, valproic acid, and combinations thereof.

Provided herein is embodiment HHH, a pharmaceutical formulation comprising a modified release formulation of minoxidil or a pharmaceutically acceptable salt thereof, wherein the modified release formulation has a Tmax of about 30 to about 360 minutes.

In an embodiment III, the pharmaceutical formulation of embodiment HHH, wherein the pharmaceutical formulation further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof.

In an embodiment JJJ, the pharmaceutical formulation of embodiment HHH, wherein the pharmaceutical formulation further comprises medrogestone, cetirizine, setipiprant, valproic acid, and combinations thereof.

Provided herein is embodiment KKK, a pharmaceutical formulation comprising a modified release formulation of minoxidil or a pharmaceutically acceptable salt thereof, wherein the modified release formulation has a Cmax of about 0.25 ng/ml to about 20 ng/ml.

In an embodiment LLL, the pharmaceutical formulation of embodiment KKK, wherein the pharmaceutical formulation further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof.

In an embodiment MMM, the pharmaceutical formulation of embodiment KKK, wherein the pharmaceutical formulation further comprises medrogestone, cetirizine, setipiprant, valproic acid, and combinations thereof.

Provided herein is embodiment NNN, a method of treating or preventing hair loss, comprising administering to a subject in need thereof a daily dose of a composition comprising a modified release formulation of minoxidil or a pharmaceutically acceptable salt thereof.

In an embodiment OOO, the method of embodiment NNN, wherein the composition further comprises a release modifier, a filler, a glidant, a lubricant, and combinations thereof.

In an embodiment PPP, the method of embodiments NNN or OOO, wherein the composition comprises about 1% to about 1.5% minoxidil or a pharmaceutically acceptable salt thereof, about 75% to about 85% of a release modifier, about 0.1% to about 0.3% of a glidant, and/or about 0.4% to about 0.6% of a lubricant.

In an embodiment QQQ, the method of embodiments NNN or OOO, wherein the composition comprises about 1% to about 1.5% minoxidil or a pharmaceutically acceptable salt thereof, about 60% to about 70% of a release modifier, about 0.1% to about 0.3% of a glidant, and/or about 0.4% to about 0.6% of a lubricant.

In an embodiment RRR, the method of embodiments NNN or OOO, wherein the composition comprises about 6% to about 7% minoxidil or a pharmaceutically acceptable salt thereof, about 50% to about 60% of a release modifier, about 0.1% to about 0.3% of a glidant, and/or about 0.4% to about 0.6% of a lubricant.

In an embodiment SSS, the method of embodiments NNN or OOO, wherein the composition comprises about 6% to about 7% minoxidil or a pharmaceutically acceptable salt thereof, about 65% to about 75% of a release modifier, about 0.1% to about 0.3% of a glidant, and/or about 0.4% to about 0.6% of a lubricant.

In an embodiment TTT, the method of embodiment OOO, wherein the release modifier is hydroxypropyl methylcellulose K4M; hydroxypropyl methylcellulose K200M, lactose monohydrate, and combinations thereof.

In an embodiment UUU, the method of embodiment OOO, wherein the filler is microcrystalline cellulose, talc, calcium carbonate (e.g., granules or powder), powdered cellulose, dextrates, kaolin, mannitol, silicic acid, sorbitol, starch, pre-gelatinized starch, and mixtures thereof.

In an embodiment VVV, the method of embodiment OOO, wherein the glidant is silica (colloidal anhydrous), starch, talc, magnesium stearate, calcium stearate, zinc stearate, dibasic calcium phosphate, magnesium carbonate, magnesium oxide, calcium silicate, silicon dioxide, and silica aerogels.

In an embodiment WWW, the method of embodiment OOO, wherein the lubricant is magnesium stearate, calcium stearate, zinc stearate, stearic acid, hydrogenated vegetable oils, sterotex, polyoxyethylene, monostearate, talc, polyethyleneglycol, sodium benzoate, sodium lauryl sulfate, magnesium lauryl sulfate, light mineral oil, or combinations thereof.

In an embodiment XXX, the method of embodiment NNN, wherein the pharmaceutical formulation further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof.

In an embodiment YYY, the method of embodiment NNN, wherein the pharmaceutical formulation further comprises medrogestone, cetirizine, setipiprant, valproic acid, and combinations thereof.

In an embodiment ZZZ, the method of embodiment XXX, wherein the non-steroid anti-androgen is selected from flutamide, clascoterone, bicalutamide, pyrilutamide, enzalutamide, nilutamide, apalutamide, proxilutamide, cimetidine, topalutamide, and combinations thereof.

In an embodiment AAAA, the method of embodiment XXX, wherein the 17α-hydroxyprogesterone derivative is selected from chlormadinone acetate, cyproterone acetate, megestrol acetate, osaterone acetate, and combinations thereof.

In an embodiment BBBB, the method of embodiment XXX, wherein the 19-norprogesterone derivative is nomegestrol acetate.

In an embodiment CCCC, the method of embodiment XXX, wherein the 19-nortestosterone derivative is selected from dienogest, oxendolone, and combinations thereof.

In an embodiment DDDD, the method of embodiment XXX, wherein the 17α-spirolactone derivative is selected from drospirenone, spironolactone, and combinations thereof.

In an embodiment EEEE, the method of embodiment XXX, wherein the 5-alpha reductase inhibitor is selected from alfatradiol, dutasteride, epristeride, finasteride, saw palmetto extract, bexlosteride, izonsteride, epigallocatechin, fluridil, and combinations thereof.

In an embodiment FFFF, the method of embodiment XXX, wherein the estrogen is selected from estradiol, estradiol esters, ethinylestradiol, conjugated estrogens, diethylstilbestrol, and combinations thereof.

In an embodiment GGGG, the method of embodiment XXX, wherein the GnRH analog is a GnRH agonist.

In an embodiment HHHH, the method of embodiment GGGG, wherein the GnRH agonist is selected from goserelin, buserelin, leuprorelin, and combinations thereof.

In an embodiment IIII, the method of embodiment XXX, wherein the GnRH analog is a GnRH antagonist.

In an embodiment JJJJ, the method of embodiment IIII, wherein the GnRH antagonist is cetrorelix.

In an embodiment KKKK, the method of embodiment XXX, wherein the prostaglandin F2α analog is latanoprost, travoprost, tafluprost, unoprostone, dinoprost, AS604872, BOL303259X, PF3187207, carboprost, and combinations thereof.

In an embodiment LLLL, the method of claim XXX, wherein the prostamide is bimatoprost.

In an embodiment MMMM, the method of embodiment XXX, wherein the prostanoid receptor agonist is fluprostenol, cicaprost, and combinations thereof.

In an embodiment NNNN, the method of embodiment XXX, wherein the prostaglandin D2 receptor antagonist is laropiprant, AM211, and combinations thereof.

In an embodiment OOOO, the method of embodiment XXX, wherein the prostaglandin E2 analog is sulprostone.

In an embodiment PPPP, the method of embodiment XXX, wherein the EP2 receptor agonist is butaprost, diazoxide, kopexil, pinacidil, ET-02, and combinations thereof.

In an embodiment QQQQ, the method of embodiment XXX, wherein the JAK inhibitor is abrocitinib, baricitinib, brepocitinib, decernotinib, delgocitinib, deuruxolitinib, deucravacitinib, fedratinib, filgotinib, gusacitinib, itacitinib, oclacitinib, pacritinib, peficitinib, ritlecitnib, ruxolitinib, tofacitinib, upadacitinib, SHR0302, ATI-2138, jacktinib, and combinations thereof.

In an embodiment RRRR, the method of embodiment XXX, wherein the alopecia areata medication is selected from etrasimod, fingolimod, ozanimod, siponimod, ponesimod, and combinations thereof.

In an embodiment SSSS, the method of embodiment XXX, wherein the supplement is selected from biotin, zinc, selenium, caffeine, sodium chloride, marine collagen, and combinations thereof.

In an embodiment TTTT, the method of embodiment NNN, wherein the composition is administered orally.

In an embodiment UUUU, the method of embodiment TTTT, wherein the modified release formulation is an extended release formulation, a sustained release formulation, a controlled release formulation, or a delayed release formulation.

In an embodiment VVVV, the method of embodiment TTTT, wherein the subject in need thereof is diagnosed with hair loss.

In an embodiment WWWW, the method of embodiment VVVV, wherein the subject is diagnosed with at least one cardiac condition selected from heart disease, chronic congestive heart failure, cardiomyopathy, tachyarrhythmia, renal disease, preexisting pulmonary hypertension, and chronic congestive heart failure not secondary to hypertension.

In an embodiment XXXX, the method of embodiment VVVV, wherein the hair loss is selected from male pattern hair loss, female pattern hair loss, hereditary hair loss, telogen effluvium, alopecia areata, central centrifugal cicatricial alopecia, lichen planopilaris, or traction alopecia.

In an embodiment YYYY, the method of embodiment WWWW, wherein the subject is taking at least one of the following for treatment of the at least one cardiac condition, an anti-hypertensive, an ace-inhibitor, an angiotensin receptor blocker, a direct renin inhibitor, a loop diuretic, a thiazide diuretic, a calcium channel blocker, a beta blocker, an anti-arrhythmic, and a diuretic.

In an embodiment ZZZZ, the method of embodiment TTTT, wherein administering results in hair regrowth.

In an embodiment AAAAA, the method of embodiment TTTT, wherein administering results in hair regrowth within about 6 months.

In an embodiment BBBBB, the method of embodiment TTTT, wherein administering results in an increased improvement in hair growth as compared to administration of an immediate-release dosage form of minoxidil or a pharmaceutically acceptable salt thereof.

In an embodiment CCCCC, the method of embodiment NNN, wherein about 25% of the composition dissolves in a neutral pH solution in less than about 2 hours or less than about 4 hours.

In an embodiment DDDDD, the method of embodiment NNN, wherein about 25% of the composition dissolves in a neutral pH solution at about 0.5 hours, about 0.75 hours, about, 1 hour, about 1.5 hours, about 2 hours, about 2.5 hours, about 3 hours, or about 4 hours.

In an embodiment EEEEE, the method of embodiment NNN, wherein about 50% of the composition in a neutral pH solution in less than about 2 hours, less than about 6 hours, or less than about 12 hours.

In an embodiment FFFFF, the method of embodiment NNN, wherein about 50% of the composition dissolves in a neutral pH solution at about 1 hour, about 1.5 hours, about 2 hours, about 3 hours, about 4 hours, about 6 hours, about 8 hours, or about 10 hours.

In an embodiment GGGGG, the method of embodiment NNN, wherein about 75% of the composition dissolves in a neutral pH solution in less than about 4 hours, less than about 8 hours, less than about 12 hours, or less than about 18 hours.

In an embodiment HHHHH, the method of embodiment NNN, wherein about 75% of the composition dissolves in a neutral pH solution at about 3 hours, about 3.5 hours, about 4 hours, about 4.5 hours, about 5 hours, about 6 hours, about 8 hours, about 10 hours, about 12 hours, about 14 hours, or about 16 hours.

In an embodiment IIIII, the method of embodiment NNN, wherein about 100% of the composition dissolves in a neutral pH in less than about 12 hours, less than about 24 hours, or less than about 48 hours.

In an embodiment JJJJJ, the method of embodiment NNN, wherein about 100% of the composition dissolves in a neutral pH at about 10 hours, about 12 hours, about 14 hours, about 16 hours, about 18 hours, about 20 hours, about 22 hours, about 24 hours, about 26 hours, or about 28 hours.

In an embodiment KKKKK, the method of embodiment NNN, wherein the composition exhibits a zero order release of the minoxidil or a pharmaceutically acceptable salt thereof, a pseudo zero order release of the minoxidil or a pharmaceutically acceptable salt thereof, a first order release of the minoxidil or a pharmaceutically acceptable salt thereof, a pseudo first order release of the minoxidil or a pharmaceutically acceptable salt thereof, or a second order release of the minoxidil or a pharmaceutically acceptable salt thereof.

In an embodiment LLLLL, the pharmaceutical formulation of embodiment NNN, wherein the pharmaceutical formulation comprises an enteric coating.

In an embodiment MMMMM, the method of embodiment TTTT, wherein the composition is administered only once daily.

In an embodiment NNNNN, the method of embodiment TTTT, wherein the composition is administered at least once daily.

In an embodiment OOOOO, the method of embodiment TTTT, wherein the composition is administered four times per day.

In an embodiment PPPPP, the method of embodiment TTTT, wherein the composition is administered three times per day.

In an embodiment QQQQQ, the method of embodiment TTT, wherein the composition is administered two times per day.

In an embodiment RRRRR, the method of embodiment TTTT, wherein the composition is administered daily for at least about 3 months with substantially no adverse effects and substantially no cardiac effects.

In an embodiment SSSSS, the method of embodiment TTTT, wherein the composition is administered daily for at least about 4 months with substantially no adverse effects and substantially no cardiac effects.

In an embodiment TTTTT, the method of embodiment TTTT, wherein the composition is administered daily for at least about 6 months with substantially no adverse effects and substantially no cardiac effects.

In an embodiment UUUUU, the method of embodiment TTTT, wherein the composition is administered daily for at least about 1 year with substantially no adverse effects and substantially no cardiac effects.

In an embodiment VVVVV, the method of embodiment TTTT, wherein the composition is administered daily indefinitely with substantially no adverse effects and substantially no cardiac effects.

In an embodiment WWWWW, the method of embodiment 98, wherein administering results in hair regrowth with substantially no clinically significant hemodynamic changes in blood pressure.

In an embodiment XXXXX, the method of embodiment TTTT, wherein administering results in substantially no cardiac effects.

In an embodiment YYYYY, the method of embodiment XXXXX, wherein the cardiac effects are selected from tachycardia, hypotension, premature ventricular contractions, and other tachyarrhythmias.

In an embodiment ZZZZZ, the method of embodiment TTTT, wherein administering results in hair regrowth with substantially no cardiac effects.

In an embodiment AAAAAA, the method of embodiment TTTT, wherein the daily dose of minoxidil or a pharmaceutically acceptable salt thereof results in fewer cardiac effects or hemodynamic effects as compared to administration of the same daily dose of immediate-release oral minoxidil or a pharmaceutically acceptable salt thereof used to treat hypertension.

In an embodiment BBBBBB, the method of embodiment AAAAAA, wherein the cardiac effects are selected from tachycardia, hypotension, premature ventricular contractions, and other tachyarrhythmias.

In an embodiment CCCCCC, the method of embodiment AAAAAA, wherein the daily dose of minoxidil or a pharmaceutically acceptable salt thereof results in substantially no cardiac effects or hemodynamic effects as compared to administration of an immediate-release oral minoxidil or a pharmaceutically acceptable salt thereof used to treat hypertension.

In an embodiment DDDDDD, the method of embodiment AAAAAA, wherein the daily dose of minoxidil or a pharmaceutically acceptable salt thereof is about 25% to about 500% of the amount of the immediate-release oral minoxidil or a pharmaceutically acceptable salt thereof used to treat hypertension.

In an embodiment EEEEEE, the method of embodiment AAAAAA, wherein the daily dose of minoxidil or a pharmaceutically acceptable salt thereof is about 10% to about 90% of the amount of the immediate-release oral minoxidil or a pharmaceutically acceptable salt thereof used to treat hypertension.

In an embodiment FFFFFF, the method of embodiment TTT, wherein the daily dose of the minoxidil or a pharmaceutically acceptable salt thereof is about 0.25 mg to about 50 mg.

In an embodiment GGGGGG, the method of embodiment TTT, wherein the daily dose of the minoxidil or a pharmaceutically acceptable salt thereof is selected from an amount of about 0.625 mg, about 1 mg, about 1.25 mg, about 1.5 mg, about 2.5 mg, about 3 mg, about 3.5 mg, about 4 mg, about 4.5 mg, about 5 mg, about 5.5 mg, about 6 mg, about 6.5 mg, about 7.0 mg, about 7.5 mg, about 8 mg, about 8.5 mg, about 9 mg, about 9.5 mg, or about 10 mg.

In an embodiment HHHHHH, the method of embodiment TTT, wherein the daily dose of the minoxidil or a pharmaceutically acceptable salt thereof is about 0.25 mg to about 20 mg per day.

In an embodiment IIIIII, the method of embodiment TTT, wherein the daily dose of the minoxidil or a pharmaceutically acceptable salt thereof is about 2.5 mg per day.

In an embodiment JJJJJJ, the method of embodiment TTT, wherein the daily dose of the minoxidil or a pharmaceutically acceptable salt thereof is about 0.00625 mg/kg/day to about 0.5 mg/kg/day.

In an embodiment KKKKKK, the method of embodiment TTT, wherein the modified release formulation releases about 50% to about 98% of the daily dose of minoxidil or a pharmaceutically acceptable salt thereof within about 12 hours after the oral administration.

In an embodiment LLLLLL, the method of embodiment TTTT, wherein the subject has a minoxidil or a pharmaceutically acceptable salt thereof plasma concentration versus time curve with a Tmax of about 30 to about 360 minutes.

In an embodiment MMMMMM, the method of embodiment TTT, wherein the subject has a minoxidil or a pharmaceutically acceptable salt thereof plasma concentration versus time curve with a Cmax of about 2.5 ng/ml to about 20 ng/ml.

In an embodiment NNNNNN, the method of embodiment TTT, wherein the minoxidil or a pharmaceutically acceptable salt thereof in the subject has a half-life or effective half-life of about 1 hour to about 24 hours.

In an embodiment OOOOOO, the method of embodiment TTT, wherein the minoxidil or a pharmaceutically acceptable salt thereof is in an amount of about 0.625 mg four times per day.

In an embodiment PPPPPP, the method of embodiment TTT, wherein the minoxidil or a pharmaceutically acceptable salt thereof is in an orally dissolving tablet.

Provided herein is embodiment QQQQQQ, a method of treating or preventing hair loss, comprising administering to a subject in need thereof a modified release formulation of minoxidil or a pharmaceutically acceptable salt thereof, wherein the modified release formulation releases about 50% to about 98% of the daily dose of minoxidil or a pharmaceutically acceptable salt thereof within about 12 hours after oral administration.

In an embodiment RRRRRR, the method of embodiment QQQQQQ, wherein the pharmaceutical formulation further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof.

In an embodiment SSSSSS, the method of embodiment QQQQQQ, wherein the pharmaceutical formulation further comprises medrogestone, cetirizine, setipiprant, valproic acid, and combinations thereof.

Provided herein is embodiment TTTTTT, a method of treating hair loss, comprising administering to a subject in need thereof a modified release formulation of minoxidil or a pharmaceutically acceptable salt thereof, wherein the modified release formulation has a Tmax of about 30 to about 360 minutes.

In an embodiment UUUUUU, the method of embodiment TTTTTT, wherein the pharmaceutical formulation further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof.

In an embodiment VVVVVV, the method of embodiment TTTTTT, wherein the pharmaceutical formulation further comprises medrogestone, cetirizine, setipiprant, valproic acid, and combinations thereof.

Provided herein is embodiment WWWWWW, a method of treating hair loss, comprising administering to a subject in need thereof a modified release formulation of minoxidil or a pharmaceutically acceptable salt thereof, wherein the modified release formulation has a Cmax of about 0.25 ng/ml to about 20 ng/ml.

In an embodiment XXXXXX, the method of embodiment WWWWWW, wherein the pharmaceutical formulation further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof.

In an embodiment YYYYYY, the method of embodiment WWWWWW, wherein the pharmaceutical formulation further comprises medrogestone, cetirizine, setipiprant, valproic acid, and combinations thereof.

Provided herein is embodiment ZZZZZZ, a kit comprising, a slow modified release vehicle comprising oral minoxidil or a pharmaceutically acceptable salt thereof.

In an embodiment AAAAAAA, the kit of embodiment ZZZZZZ, wherein the slow modified release vehicle further comprises a release modifier, a filler, a glidant, a lubricant, and combinations thereof.

In an embodiment BBBBBBB, the kit of embodiment AAAAAAA, wherein the slow modified release vehicle n comprises about 1% to about 1.5% minoxidil or a pharmaceutically acceptable salt thereof, about 75% to about 85% of a release modifier, about 0.1% to about 0.3% of a glidant, about 0.4% to about 0.6% of a lubricant.

In an embodiment CCCCCCC, the kit of embodiment AAAAAAA, wherein the slow modified release vehicle comprises about 1% to about 1.5% minoxidil or a pharmaceutically acceptable salt thereof, about 60% to about 70% of a release modifier, about 0.1% to about 0.3% of a glidant, about 0.4% to about 0.6% of a lubricant.

In an embodiment DDDDDDD, the kit of embodiment AAAAAAA, wherein the slow modified release vehicle comprises about 6% to about 7% minoxidil or a pharmaceutically acceptable salt thereof, about 50% to about 60% of a release modifier, about 0.1% to about 0.3% of a glidant, about 0.4% to about 0.6% of a lubricant.

In an embodiment EEEEEEE, the kit of embodiment AAAAAAA, wherein the slow modified release vehicle comprises about 6% to about 7% minoxidil or a pharmaceutically acceptable salt thereof, about 65% to about 75% of a release modifier, about 0.1% to about 0.3% of a glidant, about 0.4% to about 0.6% of a lubricant.

In an embodiment FFFFFFF, the kit of embodiment AAAAAAA, wherein the release modifier is hydroxypropyl methylcellulose K4M; hydroxypropyl methylcellulose K200M, lactose monohydrate, and combinations thereof.

In an embodiment GGGGGGG, the kit of embodiment AAAAAAA, wherein the filler is microcrystalline cellulose, talc, calcium carbonate (e.g., granules or powder), powdered cellulose, dextrates, kaolin, mannitol, silicic acid, sorbitol, starch, pre-gelatinized starch, and mixtures thereof.

In an embodiment HHHHHHH, the kit of embodiment AAAAAAA, wherein the glidant is silica (colloidal anhydrous) starch, talc, magnesium stearate, calcium stearate, zinc stearate, dibasic calcium phosphate, magnesium carbonate, magnesium oxide, calcium silicate, silicon dioxide, and silica aerogels.

In an embodiment IIIIII, the kit of embodiment AAAAAAA, wherein the lubricant is magnesium stearate, calcium stearate, zinc stearate, stearic acid, hydrogenated vegetable oils, sterotex, polyoxyethylene, monostearate, talc, polyethyleneglycol, sodium benzoate, sodium lauryl sulfate, magnesium lauryl sulfate, light mineral oil, or combinations thereof.

In an embodiment JJJJJJJ, the kit of embodiment ZZZZZZ, wherein the pharmaceutical formulation further comprises one or more active agents selected from a non-steroid anti-androgen, a 17α-hydroxyprogesterone derivative, a 19-norprogesterone derivative, a 19-nortestosterone derivative, a 17α-spirolactone derivative, a 5-alpha reductase inhibitor, an estrogen, a GnRH analog, a prostaglandin F2α analog, a prostamide, a prostanoid receptor agonist, a prostaglandin D2 receptor antagonist, a prostglandin E2 analog, an EP 2 receptor agonist, a JAK inhibitor, an alopecia areata medication, a supplement, and combinations thereof.

In an embodiment KKKKKKK, the kit of embodiment ZZZZZZ, wherein the pharmaceutical formulation further comprises medrogestone, cetirizine, setipiprant, valproic acid, and combinations thereof.

In an embodiment LLLLLLL, the kit of embodiment JJJJJJJ, wherein the non-steroid anti-androgen is selected from flutamide, clascoterone, bicalutamide, pyrilutamide, enzualutamide, nilutamide, apalutamide, proxilutamide, cimetidine, topalutamide, and combinations thereof.

In an embodiment MMMMMMM, the kit of embodiment JJJJJJJ, wherein the 17α-hydroxyprogesterone derivative is selected from chlormadinone acetate, cyproterone acetate, megestrol acetate, osaterone acetate, and combinations thereof.

In an embodiment NNNNNNN, the kit of embodiment JJJJJJJ, wherein the 19-norprogesterone derivative is nomegestrol acetate.

In an embodiment OOOOOOO, the kit of embodiment JJJJJJJ, wherein the 19-nortestosterone derivative is selected from dienogest, oxendolone, and combinations thereof.

In an embodiment PPPPPPPP. the kit of embodiment JJJJJJJ, wherein the 17α-spirolactone derivative is selected from drospirenone, spironolactone, and combinations thereof.

In an embodiment QQQQQQQ, the kit of embodiment JJJJJJJ, wherein the 5-alpha reductase inhibitor is selected from alfatradiol, dutasteride, epristeride, finasteride, saw palmetto extract, bexlosteride, izonsteride, epigallocatechin, fluridil, and combinations thereof.

In an embodiment RRRRRRR, the kit of embodiment JJJJJJJ, wherein the estrogen is selected from estradiol, estradiol esters, ethinylestradiol, conjugated estrogens, diethylstilbestrol, and combinations thereof.

In an embodiment SSSSSSS, the kit of embodiment JJJJJJJ, wherein the GnRH analog is a GnRH agonist.

In an embodiment TTTTTTT, the kit of embodiment SSSSSSS, wherein the GnRH agonist is selected from goserelin, buserelin, leuprorelin, and combinations thereof.

In an embodiment UUUUUUU, the kit of embodiment JJJJJJJ, wherein the GnRH analog is a GnRH antagonist.

In an embodiment VVVVVVV, the kit of embodiment UUUUUUU, wherein the GnRH antagonist is cetrorelix.

In an embodiment WWWWWWW, the kit of embodiment JJJJJJJ, wherein the prostaglandin F2α analog is latanoprost, travoprost, tafluprost, unoprostone, dinoprost, AS604872, BOL303259X, PF3187207, carboprost, and combinations thereof.

In an embodiment XXXXXXX, the kit of embodiment JJJJJJJ, wherein the prostamide is bimatoprost.

In an embodiment YYYYYYY, the kit of embodiment JJJJJJJ, wherein the prostanoid receptor agonist is fluprostenol, cicaprost, and combinations thereof.

In an embodiment ZZZZZZZ, the kit of embodiment JJJJJJJ, wherein the prostaglandin D2 receptor antagonist is laropiprant, AM211, and combinations thereof.

In an embodiment AAAAAAAA, the kit of embodiment JJJJJJJ, wherein the prostaglandin E2 analog is sulprostone.

In an embodiment BBBBBBBB, the kit of embodiment JJJJJJJ, wherein the EP2 receptor agonist is butaprost, diazoxide, kopexil, pinacidil, ET-02, and combinations thereof.

In an embodiment CCCCCCCC, the kit of embodiment JJJJJJJ, wherein the JAK inhibitor is abrocitinib, baricitinib, brepocitinib, decernotinib, delgocitinib, deuruxolitinib, deucravacitinib, fedratinib, filgotinib, gusacitinib, itacitinib, oclacitinib, pacritinib, peficitinib, ritlecitnib, ruxolitinib, tofacitinib, upadacitinib, SHR0302, ATI-2138, jacktinib, and combinations thereof.

In an embodiment DDDDDDDD, the kit of embodiment JJJJJJJ, wherein the alopecia areata medication is selected from etrasimod, fingolimod, ozanimod, siponimod, ponesimod, and combinations thereof.

In an embodiment EEEEEEEE, the kit of embodiment JJJJJJJ, wherein the supplement is selected from biotin, zinc, selenium, caffeine, sodium chloride, marine collagen, and combinations thereof.

In an embodiment FFFFFFFF, the kit of embodiment ZZZZZZ, wherein the kit comprises an information sheet.

In an embodiment GGGGGGGG, the kit of embodiment FFFFFFFF, wherein the information sheet comprises instructions for selecting an oral dosage form based on a body weight of a patient.

In an embodiment HHHHHHHH, the kit of embodiment FFFFFFFF, wherein the information sheet comprises a warning of adverse effects.

In an embodiment IIIIIII, the kit of embodiment HHHHHHHH, wherein the adverse effects are selected from peripheral edema and hirsutism.

EXAMPLES

The following are provided for exemplification purposes only and are not intended to limit the scope of the embodiments described in broad terms above.

Example 1: Case Study—28-Year Old Male with Androgenetic Alopecia

A 28-year old male with androgenetic alopecia was treated with minoxidil 1.25 mg QID. At baseline, the patient's blood pressure was 118/82. His resting heart rate was 64. The patient rechecked his blood pressure and heart rate 30 minutes after administration of each dose of minoxidil or a pharmaceutically acceptable salt thereof for 1 week and did not observe any change in heart rate, systolic blood pressure, or diastolic blood pressure >10% from baseline. The patient reported improvement in his androgenetic alopecia with subjective improvement in hair thickness and hair density at the frontal scalp and crown of the scalp. No unwanted hair growth or other adverse events, including any cardiac effects, were noticed.

Example 2: Case Study—51-Year Old Male with Androgenetic Alopecia and Hypertension A 51-year-old male with androgenetic alopecia was treated with minoxidil 2.5 mg tablet PO BID and experienced reductions in blood pressure after each administration. The patient administered the minoxidil by mouth each morning between 6 am-9 am and each evening between 6 μm-9 μm. The patient rechecked his blood pressure 30 minutes after administration of each administration of minoxidil for 1 week. The patient noted a consistent decrease of systolic blood pressure by approximately 10 mmHg. Even after decreasing the dose to 2.5 mg per day, the patient continued to note a decrease in blood pressure by approximately 10 mmHg within thirty minutes after dosing. The patient was instructed to take 0.625 mg minoxidil or a pharmaceutically acceptable salt thereof four times a day and surprisingly did not experience significant reductions in blood pressure. The patient also reported improvement in his androgenetic alopecia with the subjective improvement in hair thickness and hair density at the frontal scalp and crown of the scalp. No unwanted hair growth or other adverse events were noticed. The patient reported that despite the same total daily dose of 2.5 mg, minoxidil at 0.625 mg four times a day did not significantly lower blood pressure and was associated with improved hair growth.

Example 3: Case Study—81-Year-Old Male with Androgenetic Alopecia and Atrial Fibrillation An 81-year-old male with androgenetic alopecia presented for evaluation for treatment of his hair loss. The patient specifically requested a prescription of minoxidil immediate release. The patient disclosed a personal history of chronic atrial fibrillation requiring amiodarone therapy. On consultation with the patient's other physician, the decision was made to not proceed with minoxidil therapy due to risk of worsening his atrial fibrillation.

Example 4: Case Study—70-Year-Old Male with Androgenetic Alopecia and Premature Ventricular Contractures A 70-year-old male with androgenetic alopecia presented for evaluation for treatment of his hair loss. The patient specifically requested a prescription of minoxidilimmediate release. The patient disclosed a personal history of chronic premature ventricular contractions requiring flecainide therapy. On consultation with the patient's other physician, the decision was made to not proceed with minoxidil therapy due to risk of worsening his premature ventricular contractions.

Example 5: A Study to Evaluate the Pharmacokinetics of Modified Release Tablet Formulations of Minoxidil A Phase 1, single-part, non-randomized, open-label, six-period sequential crossover study designed to evaluate the pharmacokinetic (PK) profile of modified release formulations of minoxidil or a pharmaceutically acceptable salt thereof following single dose administration in comparison to a reference thereof immediate release formulation of minoxidil or a pharmaceutically acceptable salt in healthy subjects (FIG. 1).

Primary Objectives: To evaluate the PK profile and determine the relative bioavailability of modified release formulations of minoxidil or a pharmaceutically acceptable salt thereof following single oral dosing of modified release (MR) prototype tablets vs a reference immediate release (IR) formulation in healthy subjects in the fasted state. Primary Endpoints: Measurement of PK parameters including but not limited to: Tlag, Tmax, Cmax, AUC(0-last), AUC(0-inf), and T½, and Frels (MR vs IR) based on PK parameters Cmax, AUC(0-last) and AUC(0-inf), where possible and appropriate, for minoxidil or a pharmaceutically acceptable salt thereof.

Secondary Objectives: To provide additional information on the safety and tolerability of single oral doses of MR prototype tablet formulations of minoxidil or a pharmaceutically acceptable salt thereof and a reference IR formulation in healthy subjects. Secondary Endpoints: Incidence, severity and causality of adverse events (AEs); changes from baseline in vital signs, electrocardiograms (ECGs), physical examinations and clinical laboratory safety tests.

Exploratory Objectives: To determine the PK profile and relative bioavailability of minoxidil or a pharmaceutically acceptable salt thereof following single oral administration of a selected MR prototype tablet in the fed state compared with the fasted state. Exploratory Endpoints: Measurement of PK parameters including but not limited to: Tlag, Tmax, Cmax, AUC(0-last), AUC(0-inf), and T½, and Frels (fed vs fasted) based on PK parameters Cmax, AUC(0-last) and AUC(0-inf), where possible and appropriate, for minoxidil or a pharmaceutically acceptable salt thereof.

Methodology: This is a single center, open-label, non-randomized, six-period sequential crossover study in healthy male and female subjects aged 18 to 55 years, which is designed to evaluate the PK and safety of MR prototype tablet formulations of minoxidil or a pharmaceutically acceptable salt thereof at a range of doses to be determined throughout the study, and a reference IR tablet formulation of minoxidil or a pharmaceutically acceptable salt thereof. Optionally, the effect of food on the PK of a selected MR prototype tablet formulation of minoxidil or a pharmaceutically acceptable salt thereof may be assessed in Regimen F by administration following a high-fat breakfast, as described in the regimen table.

It is planned to enroll 16 subjects, who will receive single oral doses of investigational medicinal product (IMP) in a sequential manner. Each subject will receive the following regimens:

TABLE 1

| Period | Regimen | IMP | Dose[a] | Route of Administration |
|---|---|---|---|---|
| 1 | A | Modified Release Tablet Prototype 1 | 2.5 mg | Oral, Fasted |

TABLE 1-continued

| Period | Regimen | IMP | Dose[a] | Route of Administration |
|---|---|---|---|---|
| 2 | B | IR Reference Tablet of Minoxidil or a pharmaceutically acceptable salt thereof | 2.5 mg | Oral, Fasted |
| 3 | C | Modified Release Tablet Prototype 2 | TBD mg based on PK of Prototype 1 | Oral, Fasted |
| 4 | D | Modified Release Tablet Prototype 3 | TBD mg based on PK of Prototype 2 | Oral, Fasted |
| 5 | E | Modified Release Tablet Prototype 4 | TBD mg based on PK of Prototype 3 | Oral, Fasted |
| 6 | F | Modified Release Tablet Prototype 1, 2, 3, or 4 Or[b] Modified Release Tablet Prototype 5 | TBD mg Or TBD mg based on PK of Prototype 4 | Oral, Fed[c] Or Oral, Fasted |

Modified Release Tablet Prototypes 1 to 5 of minoxidil or a pharmaceutically acceptable salt thereof will be selected from a 2-dimentional design space describing dose strength and release rate (2 mg to 10 mg dose strength; 6 h to 18 h release rate). IMPs are free base equivalents. The order in which regimens are dosed may be subject to change due to logistical reasons.

[a]For all regimens, multiple tablets may be administered to achieve the required dose.

[b]The dose and formulation for Regimen F will be decided at the interim decision meeting using all available data. No dose selected will be expected to result in a geometric mean Cmax >20 ng/mL or exceed 30 mg based on impurity limits. If the selected formulation does not provide the required data, a previously tested formulation may be used in a subsequent study period. However, if the dose level met any dose decision or study stopping criteria, that dose level must not be repeated.

[c]If the fed dosing option is chosen, the dose will be the same as that used in the fasted stated for that prototype.

Study Design: Each period will follow the same study design. Subjects will undergo preliminary screening procedures for the study at the screening visit (Day −28 to Day −2). Subjects will be admitted to the clinical unit in the evening of Day −1 for all regimens and will remain on site until 48 h post-dose (Day 3). For each period, the IMP will be administered to subjects on the morning of Day 1 following an overnight fast of 10 h, or 30±5 min after the start of a high-fat breakfast (and following an overnight fast of 8 h; optional for Regimen F). Blood samples will be collected at regular intervals for PK and safety analysis from Day 1 to discharge from the clinical unit at 48 h post-dose. A follow-up phone call will take place 3 to 7 days post-final dose to ensure the ongoing wellbeing of the subjects. If a subject reports any AEs which represent a cause for concern they will be required to attend the clinical unit for a follow-up assessment. This will be an unscheduled visit.

Following administration of Regimens B, C, D and E, there will be an interim analysis and review of available PK and safety data from previous periods in order to determine the dose and prototype composition to be used in the following regimen and, where applicable, the prandial state. There will be a minimum washout of 7 days between each IMP administration; however, there will also be sufficient time between each period to permit the decision process and product manufacture.

Number of Subjects Planned: The study is exploratory, and no formal sample size calculation has been made. Based on experience from previous studies of a similar design, a sample size of 16 subjects to obtain 12 evaluable subjects is considered sufficient to meet the objectives of the study. An evaluable subject for the MR vs IR relative bioavailability primary objective is defined as a subject who has received at least one MR tablet prototype and the IR reference tablet both in the fasted state and has PK data up to 48 h post-dose for both regimens. An evaluable subject for the PK primary objective is defined as a subject who has received at least 1 dose of IMP and has PK data up to 48 h post-dose. An evaluable subject for the safety secondary objective is defined as a subject who has received at least 1 dose of IMP and has safety data up to 48 h post-dose. An evaluable subject for the optional food effect relative bioavailability exploratory objective is defined as a subject who has received the same MR tablet prototype at the same dose in both the fed and fasted states and has PK data up to 48 h post-dose for both regimens.

Subjects withdrawn due to an IMP-related AE will not be replaced. Subjects who are withdrawn for other reasons may be replaced as required by agreement between the investigator and Applicant to ensure sufficient evaluable subjects.

Duration of Study: Subjects will receive a single dose administration on 6 separate occasions. The estimated time from screening until the final follow-up phone call is approximately 14 weeks.

Investigational Medicinal Product, Dose and Mode of Administration: The following IMPs will be used in this clinical study (Table 2). Oral doses will be administered with a total of 240 mL of water. If required, additional water in 50 mL aliquots may be given with the IMP.

TABLE 2

| IMP Name | Dose[a] | Route of Administration |
|---|---|---|
| Modified Release Tablet Prototype of minoxidil or a pharmaceutically acceptable salt thereof | 2 mg to 10 mg | Oral, Fasted or Fed (Regimen F option) |

TABLE 2-continued

| IMP Name | Dose[a] | Route of Administration |
|---|---|---|
| IR Reference Tablet of Minoxidil or a pharmaceutically acceptable salt thereof | 2.5 mg | Oral, Fasted |

Modified Release Tablet Prototypes 1 to 5 of minoxidil or a pharmaceutically acceptable salt thereof will be selected from a 2-dimentional design space describing dose strength and release rate (2 mg-10 mg dose strength; 6 h-18 h release rate)
IMPs are free base equivalent
[a]Multiple tablet units may be administered to achieve the required total dose Study Assessments: The following blood and urine samples will be collected, and assessments performed, at specified time points: 1)•Minoxidil or a pharmaceutically acceptable salt thereof in plasma for PK analysis; 2)Safety assessments comprising AE monitoring, clinical laboratory tests (clinical chemistry, hematology, and urinalysis), physical examinations, body weight, single 12-lead ECGs, and vital signs.

Statistical Analysis: PK parameters for minoxidil or a pharmaceutically acceptable salt thereof will be calculated using standard non-compartmental analysis to obtain at a minimum Tlag, Tmax, Cmax, AUC(0-last), AUC(0-inf) and T½, where possible and appropriate. Descriptive summaries for all safety and PK data by regimen will be provided (including changes from baseline as appropriate). In addition, formal statistical analysis will be performed on the PK parameters Cmax, AUC(0-last) and AUC(0-inf) to assess relative bioavailability between test and reference formulations, and potentially to assess for the effect of food on a selected prototype. The PK parameters will undergo a natural logarithmic transformation and will be analyzed using a mixed effect model with terms for regimen as a fixed effect and subject as a random effect. Formal statistical analysis may also be performed on the log-transformed PK parameters Cmax, AUC(0-last) and AUC(0-inf) to assess dose proportionality. This will be assessed using a mixed effects model, including log dose as a fixed effect and subject as a random effect.

5.2 Investigational Medicinal Products: IMPs that will be used in this clinical study are presented in Table 2. Only subjects enrolled in the study may receive study treatment, and only authorized site staff may supply or administer study treatment. All study treatments will be stored in a secure, environmentally-controlled, and monitored (manual or automated) area in accordance with the labelled storage conditions with access limited to the investigator and authorized site staff.

5.3 Previous Study Findings: Given the well-established safety and efficacy profile of minoxidil or a pharmaceutically acceptable salt thereof, no non-clinical or clinical studies in humans have been conducted with MR oral formulations of minoxidil or a pharmaceutically acceptable salt thereof to date. However, other marketed products containing minoxidil or a pharmaceutically acceptable salt thereof have been studied, and such related information is presented below. Nonetheless, depending on how drug products are formulated, as well as their route of administration, in-vivo release profile, volume and concentration of administration, among other factors, the safety and efficacy profile of a drug product can materially change, be it favorably or unfavorably. Therefore, the information presented herein for other products containing minoxidil or a pharmaceutically acceptable salt thereof is provided as supportive background information only. The relevance of these findings to MR oral formulations of minoxidil or a pharmaceutically acceptable salt thereof remains to be determined.

5.3.1 Non-clinical Findings: Applicant has not conducted any non-clinical studies with MR oral formulations of minoxidil or a pharmaceutically acceptable salt thereof. Non-clinical information on the active ingredient is available from the Summary of Product Characteristics for Loniten®, a previously approved oral product containing minoxidil or a pharmaceutically acceptable salt thereof.

Non-clinical Toxicology: Oral median lethal dose (LD50) in rats has ranged from 1321 mg/kg to 3492 mg/kg; in mice, 2456 mg/kg to 2648 mg/kg. Side effects include cardiovascular effects associated with hypotension such as sudden weight gain, rapid heartbeat, faintness or dizziness.

In dogs, various cardiac lesions have been found following short-term administration of minoxidil or a pharmaceutically acceptable salt thereof (0.5 mg to 10 mg/kg/day) including a grossly visible hemorrhagic lesion of the right atrium; necrosis of the papillary muscles and subendocardial areas of the left ventricle; and hemorrhagic lesions in the epicardium, endocardium, walls of small coronary arteries and arterioles, and left atrium. In addition, long term animal studies demonstrated cardiac hypertrophy, cardiac dilation, and serosanguineous pericardial fluid.

Non-clinical Carcinogenicity: Two-year carcinogenicity studies of minoxidil or a pharmaceutically acceptable salt thereof have been conducted by the dermal and oral routes of administration in mice and rats. There were no positive findings with oral administration in rats. Dietary administration of minoxidil or a pharmaceutically acceptable salt thereof in mice for up to 2 years was associated with an increased incidence of malignant lymphomas in females at all dose levels (10, 25, and 63 mg/kg/day) and an increased incidence of hepatic nodules in males (63 mg/kg/day). There was no effect of dietary minoxidil or a pharmaceutically acceptable salt thereof on the incidence of malignant liver tumors. Changes in incidence of neoplasms found to be increased in the oral carcinogenicity studies were typical of those expected in rodents treated with other hypotensive agents (adrenal pheochromocytomas in rats), or representative of normal variations with the range of historical incidence for rodent neoplasms (malignant lymphomas, liver nodules/adenomas in mice).

Minoxidil or a pharmaceutically acceptable salt thereof was not mutagenic in the *Salmonella* (Ames) test, the deoxyribonucleic acid (DNA) damage alkaline elution assay, the in vitro rat hepatocyte unscheduled DNA synthesis assay, the rat bone marrow micronucleus assay, or the mouse bone marrow micronucleus assay. An equivocal result was recorded in an in vitro cytogenetic assay using Chinese hamster cells at long exposure times, but a similar assay using human lymphocytes was negative.

No evidence of carcinogenicity was observed when minoxidil or a pharmaceutically acceptable salt thereof was used in rats in doses 15 times the usual human dosage for 22 months.

Reproductive Toxicity: Oral minoxidil or a pharmaceutically acceptable salt thereof has been associated with increased fetal resorption in rabbits when administered at 5 times the maximum recommended oral antihypertensive human dose. This effect was not seen in rats. There was no evidence of teratogenic effects in rats and rabbits.

5.3.2 Clinical Findings: No PK studies in humans have been previously conducted with MR oral formulations of minoxidil or a pharmaceutically acceptable salt thereof. However, other products containing minoxidil or a pharmaceutically acceptable salt thereof have been studied. The relevance of these findings to MR oral formulations of minoxidil or a pharmaceutically acceptable salt thereof is not known, but it is the only supportive information currently available. The PK of other oral formulations of minoxidil or a pharmaceutically acceptable salt thereof in humans has been evaluated. There are 71 clinical studies with minoxidil or a pharmaceutically acceptable salt thereof currently listed (as of February 2023) in the clinicaltrials.gov database; 39 studies have been completed and 10 studies which are detailed in the IB have results posted. Of these, 7 studies are investigating topical minoxidil or a pharmaceutically acceptable salt thereof in alopecia. The majority of these studies (5/7) used minoxidil or a pharmaceutically acceptable salt thereof as the active comparator. One study compared minoxidil or a pharmaceutically acceptable salt thereof topical foam 5% versus minoxidil or a pharmaceutically acceptable salt thereof topical solution 2% in female pattern hair loss. There was a total of 322 subjects enrolled in the study. Ten serious adverse events (SAEs) were reported, none of which were reported more than once (NCT01145625). Another study compared minoxidil or a pharmaceutically acceptable salt thereof topical foam 5% versus vehicle topical foam. There was a total of 404 subjects enrolled in the study. Six SAEs were reported in subjects treated with minoxidil or a pharmaceutically acceptable salt thereof including, cardiovascular disorder, gastritis, dehydration, osteoarthritis, ovarian neoplasm, uterine leiomyoma, renal failure, and hypertensive crisis (NCT01226459). Nine studies were listed as "recruiting".

Clinical Pharmacokinetics and Product Metabolism: Minoxidil or a pharmaceutically acceptable salt thereof is almost completely absorbed (>90%) from the gastrointestinal tract. Peak plasma levels are reached within 1 h. Minoxidil or a pharmaceutically acceptable salt thereof is widely distributed in the tissues with an apparent volume of distribution of 2.8 L/kg to 3.3 L/kg. The elimination half-life of minoxidil or a pharmaceutically acceptable salt thereof is 2.77 h to 4.2 h. About 90% of oral minoxidil or a pharmaceutically acceptable salt thereof is metabolized, primarily by conjugation with glucuronic acid. The drug and its metabolites are largely excreted in the urine. Renal clearance is 73.3 mL/min. The absorption and excretion of oral minoxidil or a pharmaceutically acceptable salt thereof has been studied in 29 healthy volunteers and 7 hypertensive patients.

In the healthy volunteer study, subjects received either minoxidil or a pharmaceutically acceptable salt thereof 2.5 mg, 5 mg, or 10 mg by oral administration. PK and urinary excretion data were supportive of dose-independent PK over the range of doses studied. Repeated measures analysis of variance (ANOVA) revealed borderline significant treatment and time effects (p=0.0779 and p=0.0203, respectively) on both systolic and diastolic blood pressure. When systolic and diastolic blood pressure results were analyzed by ANOVA at each sampling time, no significant treatment effects were observed. Significant time effects within treatments were observed, but the differences were generally less than 10%. These observations indicate that minoxidil or a pharmaceutically acceptable salt thereof has little effect on blood pressure in normotensive subjects. The study generated the PK data presented in Table 3.

TABLE 3

PK Parameters for Minoxidil or a pharmaceutically acceptable salt thereof at Dose Levels 2.5 mg, 5 mg, and 10 mg

| Dose level (mg) | 2.5 | 5 | 10 |
|---|---|---|---|
| Tmax (h) | 0.566 | 0.389 | 0.419 |
| Cmax (ng/mL) | 16.8 | 37.2 | 74.7 |
| AUC(last) (ng · h/mL) | 25.3 | 55.1 | 112 |
| T½ (h) | 1.07 | 1.27 | 1.34 |

In hypertensive patients, the total clearance of minoxidil or a pharmaceutically acceptable salt thereof greatly exceeded the renal clearance, suggesting a predominate role of metabolism in its disposition. A glucuronide conjugate of minoxidil or a pharmaceutically acceptable salt thereof was the predominant metabolite in the urine during the first 12 h. Over 80% of radiolabeled minoxidil or a pharmaceutically acceptable salt thereof and its metabolites were recovered from urine within 24 h after oral administration. The remainder was accumulated in urine over the next 4 days. In total, 97% of radioactivity was recovered from urine and only 3% was found in feces.

Clinical Safety: A study assessed the clinical, laboratorial, and cardiovascular effects in male adults taking minoxidil or a pharmaceutically acceptable salt thereof 5 mg by oral route at bedtime for AGA. Thirty-four subjects without cardiovascular disease were assessed through biochemical profile, 24-h Holter monitoring, and 24-h ambulatory blood pressure monitoring before and 24 weeks after treatment. At the 24 week follow up, 20.6% of subjects reported headache, 2.9% reported vertigo, and 2.9% reported edema. No adverse cardiovascular outcomes were observed. Nineteen subjects (55.9%) reported hypertrichosis. There were no differences in laboratory variables between before and after treatment values. Although 1 subject developed tachycardia at the follow-up visit, no overall change in mean heart rate occurred. The mean heart rate values at 24 weeks were highly correlated with their before treatment values. The occurrence of extrasystoles did not differ pre and post treatment. Alterations in ventricular repolarization were not remarkable. Overall, 24 weeks of low dose oral minoxidil or a pharmaceutically acceptable salt thereof was safe in men with AGA, as the subjects presented with no relevant alterations in terms of their biochemical profile, 24-h Holter monitoring, and ambulatory blood pressure monitoring.

6. Rationale: Applicant aims to develop a once-daily solid oral modified release formulation of minoxidil or a pharmaceutically acceptable salt thereof at a dose which stimulates hair growth and limits the potential for unwanted hemodynamic and cardiac effects. This study will use a crossover design in order to make comparisons between formulations administered to the same subjects. As this is a crossover trial with 6 periods, in which the subjects receive IMP in a sequential manner, the study will be open-label and no randomization is required.

The Clinical Trial Authorization application for this study describes a flexible protocol design using the concept of formulation design space, whereby a flexible dose range and release rate can be explored to allow decision-making in response to interim PK observations. The principles of a flexible protocol were discussed and agreed with the MHRA at a Scientific Advice Meeting between the MHRA and the trial site.

Based upon the concept of formulation design space, specific IMPs are not detailed within the Investigational Medicinal Product Dossier (IMPD) but rather a defined range of formulation inputs and corresponding performance outputs are described and justified based on in vitro studies. The chosen formulation from within the approved design space for the first prototype to be dosed will be documented in a decision document and approved by Applicant and the investigator ahead of dosing.

Modified Release Tablet Prototypes 1 to 5 of minoxidil or a pharmaceutically acceptable salt thereof will be selected from a 2-dimensional design space describing dose strength and release rate.

6.2 Dose Rationale: The dose selected for the immediate release formulation will be 2.5 mg as this is a dose that has previously been administered to healthy adults and is known to be well tolerated. It is also the lowest unit dose strength available commercially and is a dose that is below the recommended starting dose for the treatment of severe hypertension, which is 5 mg per day.

The proposed starting dose for the modified release formulation is also set at 2.5 mg to provide adequate safety coverage in the instance that the novel modified release formulation dose dumps and behaves like an immediate release formulation. The maximum dose that may be administered in this study will be limited by an exposure cap on the maximum plasma concentration (Cmax) which is considered to be the most relevant pharmacokinetic parameter that will drive the potential cardiovascular AEs. The selected Cmax exposure limit of 20 ng/mL is based on a set of previous studies exploring the PK and safety of minoxidil or a pharmaceutically acceptable salt thereof. In a study exploring the hemodynamic effects of steady state intravenous infusions of minoxidil or a pharmaceutically acceptable salt thereof in hypertensive patients, steady state concentrations between 4.5 ng/mL and 83.0 ng/mL were assessed for effect on systolic blood pressure, diastolic blood pressure and heart rate. While no significant effect was observed in the patients with regard to systolic blood pressure, effects were observed on diastolic blood pressure and heart rate. Steady state plasma concentrations above 20 ng/mL were associated with significant (>5 beats per minute) changes in heart rate. Another study investigated the oral PK profile for minoxidil or a pharmaceutically acceptable salt thereof tablets at dose levels of 2.5 mg, 5 mg and 10 mg in healthy subjects and provided estimates of Cmax of 16.8 ng/mL, 37.2 ng/mL and 74.7 ng/mL for each dose level respectively. This suggests that only the highest two doses would exert significant (defined as heart rate increase >5 bpm) hemodynamic effects. Moreover, for these doses with the immediate release formulation, the duration of time that the plasma concentrations exceeded the 20 ng/mL threshold was short based on the observed half-life of around 1 h. At the 5 mg dose level, plasma concentrations were above 20 ng/mL for around 1 h and at 10 mg for around 2 h. It is therefore expected that the starting dose level will be well tolerated.

The target pharmacokinetic profile of the modified release formulation will be to maintain plasma concentrations throughout the planned dosing interval while maintaining Cmax below the exposure cap. The AUC will therefore be monitored throughout the study but is not required to be restricted, as the long-term safety of minoxidil or a pharmaceutically acceptable salt thereof is well established and Cmax appears to be key when considering acute cardiovascular AEs.

It is expected that a modified release formulation dose exceeding 2.5 mg will be needed to achieve the target PK profile. Following Period 2 there will be an interim analysis of the data and subsequent doses will be selected based on the observed PK and safety of the initial modified release (MR) formulation tested. The formulation release rate may be adjusted if it is apparent the drug is releasing too fast or slow within the gastrointestinal tract, or the dose may be adjusted if the release rate appears acceptable but the overall Cmax, AUC and C24 are too high/low. The highest dose that may be given in this study is restricted to a maximum of 30 mg based on impurity limits for the modified release prototype formulations.

For comparison the recommended starting dose for Loniten® is 5 mg per day in patients with severe hypertension. As required, this dosage can later be increased up to 20 mg, and then to 40 mg daily (given as a single dose or in two divided doses) to deliver the required blood pressure reductions. Dose increases are recommended to be made at increments of 5 mg to 10 mg minoxidil or a pharmaceutically acceptable salt thereof per day at intervals of three or more days. If a dose of 50 mg of minoxidil or a pharmaceutically acceptable salt thereof has been reached, the dose may be increased by 25 mg minoxidil or a pharmaceutically acceptable salt thereof per day to a maximum dose of 100 mg per day which is above the maximum permitted dose in this study of 30 mg per day.

6.3 Population Rationale: As this is a Phase I study assessing PK, relative bioavailability and safety of MR oral formulations of minoxidil or a pharmaceutically acceptable salt thereof, the most relevant population is healthy volunteers, as recommended by the US FDA and the European Medicines Agency (EMA). Subjects who are non-smokers without a history of alcohol or drug abuse or regular co-medication (except hormonal contraception and hormone replacement therapy [HRT]) are proposed to avoid interaction on drug metabolism and to avoid non-compliance.

There is limited data from the use of minoxidil or a pharmaceutically acceptable salt thereof in pregnant women. Studies in animals have shown reproductive toxicity and minoxidil or a pharmaceutically acceptable salt thereof is not recommended during pregnancy and in women of childbearing potential not using contraception; therefore, women of childbearing potential will only be allowed to participate in the study as long as they comply with the contraception requirements detailed in the study protocol.

Based on the above considerations and target population, healthy non-pregnant and non-lactating female subjects and healthy male subjects, aged 18 to 55 years are considered suitable for this study.

6.4 Risks and Benefits Associated with Minoxidil or a pharmaceutically acceptable salt thereof. Administration: Minoxidil or a pharmaceutically acceptable salt thereof was chosen for development as an oral product for the treatment of AGA because of its extensive current use as a topical product for AGA. Minoxidil or a pharmaceutically acceptable salt thereof has a long history (>35 years) of safe and effective use for the treatment of varying types of alopecia including AGA. To date, no clinical safety and efficacy studies have been conducted with MR oral formulations of minoxidil or a pharmaceutically acceptable salt thereof. However, a number of clinical studies assessing safety and efficacy have been completed as part of the development program for another approved oral formulation of minoxidil or a pharmaceutically acceptable salt thereof, Loniten®, which is approved for use.

When used as monotherapy for severe hypertension as chronic therapy, minoxidil or a pharmaceutically acceptable salt thereof can cause significant retention of salt and water leading to physical signs such as oedema, and to clinical deterioration of some patients with heart failure. Diuretic treatment alone, or in combination with restricted salt intake is, therefore, necessary for all patients taking minoxidil or a pharmaceutically acceptable salt thereof. Hemodilution may occur leading to temporary decrease in hematocrit, hemoglobin, and erythrocyte count (by approximately 7% initially which then recovers to pre-treatment levels). Electrolyte balance should be monitored for evidence of fluid retention. In this study single doses of minoxidil or a pharmaceutically acceptable salt thereof followed by a suitable washout period are not expected to be associated with any significant retention of salt or water. Furthermore, this study will only recruit healthy volunteers with normal cardiac and renal function and clinical laboratory measurements (clinical chemistry and hematology) will take place in each period of this study to monitor for any fluid or electrolyte disturbance.

Although minoxidil or a pharmaceutically acceptable salt thereof is a vasodilator and may cause reflex tachycardia resulting in angina pectoris in patients at risk, this study will recruit young healthy adults who have a normal electrocardiogram (ECG) and no history or risk factors for heart disease. The dose selected, dose cap and exposure cap will limit the likelihood and the severity of any cardiovascular effects and it is considered unlikely that any safety issues related to this risk will occur. Close monitoring and supportive treatment (intravenous fluids, supine or head down posture etc.) will be initiated in any subject who develops cardiovascular AE's.

The effect of minoxidil or a pharmaceutically acceptable salt thereof may be additive to concurrent antihypertensive agents and other agents with blood pressure lowering effects. The interaction of minoxidil or a pharmaceutically acceptable salt thereof with sympathetic-blocking agents such as guanethidine or betanidine may produce excessive blood pressure reduction and/or orthostatic hypotension. Subjects who are taking, or have taken, any prescribed or over-the-counter drug or herbal remedies (other than up to 4 g of paracetamol per day or HRT/hormonal contraception) in the 14 days before IMP administration will be excluded from this study.

There may be a risk of hypotension, postural hypotension, postural instability, pre-syncope and syncope associated with maximum plasma concentration and so subjects will be restricted to their bed for the first 4 h post-dose and thereafter encouraged to assume a standing posture in a gradual way before mobilizing, such as remaining seated for several minutes before standing, and then standing at the bedside for several minutes before proceeding to mobilize away from the bed area. This will help reduce the risk of sudden loss of consciousness and possible injury.

Soon after starting minoxidil or a pharmaceutically acceptable salt thereof therapy approximately 60% of patients exhibit ECG alterations in the direction and magnitude of their T waves. Large changes may encroach on the ST segment, unaccompanied by evidence of ischemia. These asymptomatic changes usually disappear with continuing minoxidil or a pharmaceutically acceptable salt thereof treatment. The ECG reverts to the pre-treatment state when minoxidil or a pharmaceutically acceptable salt thereof is discontinued. Single ECGs will be conducted throughout each period of treatment in this study to monitor for cardiovascular effects.

Hemodynamic effects are typically seen above plasma concentrations of 20 ng/mL and are less common in normotensive patients. Therefore, cardiovascular effects are not expected with the appropriate use of MR oral formulations of minoxidil or a pharmaceutically acceptable salt thereof; however, vital signs including systolic blood pressure, diastolic blood pressure and heart rate will be monitored throughout the study.

Hypertrichosis occurs in most patients treated with minoxidil or a pharmaceutically acceptable salt thereof and all patients should be warned of this possibility before starting therapy although this is considered unlikely in this single dose pharmacokinetic study. Most patients will experience an elongation, thickening and enhanced pigmentation of fine body hair. Usually these signs will emerge 3 to 6 weeks after starting treatment. They initially emerge in the face, and they may slightly subside with continued treatment. However, hypertrichosis was hardly or not at all tolerable in less than 10% of patients. Spontaneous reversal to the pre-treatment state can be expected 1 to 6 months after cessation of therapy.

Potential reactions for the products in this study therefore may include but are not necessarily limited to: temporary edema; pericarditis; pericardial effusion and tamponade; hypertrichosis; rashes including bullous eruptions, toxic epidermal necrolysis, and Stevens-Johnson Syndrome; thrombocytopenia and leukopenia; nausea and/or vomiting; breast tenderness; ECG changes; hemodilution; increased alkaline phosphatase, increased serum creatinine.

Phototoxicity has not been included as a warning for the use of the approved product Loniten®, therefore, there are no safety concerns regarding sunlight exposure for this study.

6.4.2 General Risks and Overall Risk-Benefit Assessment: Collecting a blood sample from a vein may cause pain, swelling, bruising, light-headedness, fainting, and very rarely, clot formation, nerve damage and/or infection at the site of the needle stick.

During cannulation, more than one attempt may be needed to insert the cannula in a vein of a subject and it is possible that bruising and/or inflammation may be experienced at the site of cannulation.

ECG stickers on the subjects' chests and limbs may cause some local irritation and may be uncomfortable to remove but subjects will be closely monitored to ensure any local irritation does not persist.

There is no benefit to the subjects from taking part in this study. The development of a product to promote hair growth or improve the treatment of AGA will be of benefit to the patients with hair loss and/or AGA.

The overall risk benefit balance is therefore considered to be acceptable.

7. Objectives and Endpoints:

Primary Objectives: To evaluate the PK profile and determine the relative bioavailability of MR oral formulations of minoxidil or a pharmaceutically acceptable salt thereof following single oral dosing vs. a reference immediate release (IR) formulation in healthy subjects in the fasted state. Primary Endpoints: Measurement of PK parameters for minoxidil or a pharmaceutically acceptable salt thereof including but not limited to: Tlag, Tmax, Cmax, AUC(0-last), AUC(0-inf), and T½, and Frels (MR vs IR) based on PK parameters Cmax, AUC(0-last) and AUC(0-inf), where possible and appropriate.

Secondary Objectives: To provide additional information on the safety and tolerability of single oral doses of MR oral formulations of minoxidil or a pharmaceutically acceptable salt thereof and a reference IR formulation in healthy subjects. Secondary Endpoints: Incidence, severity and causality of adverse events (AEs); changes from baseline in vital signs, electrocardiograms (ECGs), physical examinations and clinical laboratory safety tests.

Exploratory Objectives: To determine the PK profile and relative bioavailability of minoxidil or a pharmaceutically acceptable salt thereof following single oral administration of a selected MR oral formulations of minoxidil or a pharmaceutically acceptable salt thereof in the fed state compared with the fasted state. Exploratory Endpoints: Measurement of PK parameters for minoxidil or a pharmaceutically acceptable salt thereof including but not limited to: Tlag, Tmax, Cmax, AUC(0-last), AUC(0-inf), and T½, and Frels (fed vs fasted) based on PK parameters Cmax, AUC(0-last) and AUC(0-inf), where possible and appropriate.

8 Study Design Details 8.1 Criteria for In-Study Decisions: In-study decisions will be made by the safety advisory committee (SAC), which will always comprise the investigator, Applicant's representative medical monitor or Applicant's medically qualified designee who is familiar with the study protocol and IB, and a PK expert where appropriate.

8.1.1 Decision Points: Interim reviews will occur after Regimens B, C, D and E. The following in-study decisions will be made using data from all previous periods: 1) MR formulation and dose for subsequent regimen (from within the 2-dimensional design space describing dose strength and release rate); 2)•Prandial status (for Regimen F only).

If the selected formulation does not provide the required data, a previously tested formulation may be used in a subsequent study period. However, if the dose level met any dose decision or study stopping criteria, that dose level must not be repeated.

8.1.2 Criteria for Formulation, Dose and Prandial State Selection: Formulation release rate, formulation dose and prandial state selection (where applicable) will only be made after a complete review of all data collected from the previous dose group(s). For formulation, dose and prandial state selection to occur, data must be available from approximately 12 subjects who have completed the planned PK and safety assessments up to 48 h post-dose. If data are not available for 12 subjects, the investigator, scientific lead and sponsor will make a decision as to whether the data available are sufficient to support the formulation selection decision. If data in fewer subjects are used in the decision process and the formulation prototype is considered to be sub-optimal from an exposure perspective, additional subjects will not be dosed to increase the number of subjects in the completed regimen; however, additional subjects may be enrolled to achieve the target number of subjects in subsequent regimens.

The following data are required: AEs, vital signs, ECGs, safety laboratory tests, plasma concentrations of minoxidil or a pharmaceutically acceptable salt thereof, PK parameter estimates (Tlag, Tmax, Cmax, AUC (0-last), AUC (0-inf), C24, Frel, and T½) where possible and appropriate.

The decision on formulation, dose and prandial state selection (where applicable) will be made by the SAC. The decision will be documented and signed by the investigator as per current standard operating procedure (SOP). Evidence of the decision will be retained in the ISF.

Rules for dose decisions in this study are as follows: 1) Any dose escalations between periods will be <2-fold; 2) No dose selected will exceed 30 mg; 3) No dose selected will be expected to result in a geometric mean Cmax >20 ng/mL; 4)•If the trial is halted based on the criteria in the protocol, no further dose decisions will be made.

8.2 Subject Withdrawal: If a subject wishes to leave the study at any time, they will be permitted to do so. Every reasonable effort will be made to complete a final assessment/discharge procedures.

Early withdrawal is defined as the date of the decision to withdraw the subject from the study. Subject completion is defined as the date of the last procedure conducted or last contact (e.g. phone call or unscheduled visit) for that subject.

If a subject requests to leave the clinical unit earlier than the planned discharge time e.g. due to unforeseen personal circumstances, but aims to return to the clinical unit to complete the study, this will be documented as a subject self-discharge and a protocol deviation. The subject must complete the planned assessments/discharge procedures before discharge from the clinical unit and may return for the next study period/assessments, as planned following agreement between Applicant and the investigator.

Subjects will be withdrawn from the study drug(s) for the following reasons: 1)•Experiencing a serious or severe AE including but not limited to: a) corrected QT interval by Fridericia's formula (QTcF) of >500 msec or increase in QTcF interval of >60 msec from baseline (confirmed following a repeat ECG); and b) alanine aminotransferase (ALT) concentration >3×the upper limit of the reference range (confirmed following a repeat ALT blood test). 2) Pregnancy. 3) Termination of the study. 4) Upon the subject's request (withdrawal of consent). 5) Significant deviation from the protocol. 6) Concurrent illness that would adversely affect subject safety or data integrity or requirement for prohibited medication. 7) At the discretion of the investigator.

For the purpose of withdrawal criteria, baseline will be considered as the last available assessment prior to first dose. For a subject who withdraws because of an IMP-related AE, every effort will be made to ensure that the AE is followed up until resolution if possible and that the subject completes follow-up procedures. Early withdrawal of consent by the subject to participate in any further activities will be distinguished from withdrawal for any of the other above reasons.

8.3 Subject Replacement: Withdrawn subjects may be replaced, at the discretion of the investigator and sponsor, with the aim of ensuring that the objectives of the trial can be met. Replacement subjects will receive the treatment(s) allocated to the subject who is being replaced. The sponsor and investigator will decide which treatment periods each replacement subject will complete in order to meet the required objectives of the study.

Replacement subjects enrolled will be dosed with the next planned regimen of the withdrawn subject, and they will not receive any regimens that the withdrawn subject has already received with the exception of the need to increase the number of subjects to obtain the number of evaluable subjects required for interim decisions and to obtain data in any other treatment that is required for a valid comparison e.g. test vs reference or fed vs fasted.

Any subject withdrawn due to an IMP-related AE will not be replaced.

Subjects withdrawing for other reasons may be replaced as required by agreement between the investigator and Applicant to ensure sufficient evaluable subjects.

8.4 Stopping Criteria: The study will be halted, and the risk to other subjects evaluated if any of the following criteria are met: 1) A serious adverse reaction (i.e. a SAE considered at least possibly related to the IMP administration) in one subject. 2) Severe non-serious adverse reactions (i.e. severe non-serious AE considered as, at least possibly related to the IMP administration) in two subjects in the same cohort, independent of within or not within the same system organ class.

Relatedness to IMP will be determined by the investigator. If the study is halted, a temporary halt will be submitted to the MHRA and ethics committee (EC) in the form of a substantial amendment. The study may be resumed or terminated; however, it will not be resumed until a further substantial amendment to resume the study is submitted and approved by MHRA and EC.

8.5 Study Termination: After the start of protocol activities but prior to the commencement of dosing, the study may be terminated by Applicant and investigator without consultation with the MHRA and EC. Notification of early termination must be provided to the MHRA and EC immediately and at the latest within 15 days after the study is terminated, clearly explaining the reasons. A description of follow-up measures taken for safety reasons, if applicable, will also be provided.

If the study is abandoned prior to commencement of any protocol activities, the investigator or sponsor must notify the EC and MHRA by letter outlining the reasons for abandonment of the trial.

Once exposure to dosing has begun, the study will be completed as planned unless the following criteria are satisfied that require a temporary halt or early termination of the study: 1)•The occurrence of serious or severe AE(s), as defined in Section 8.5, if considered to be related to the IMP, as defined in Section 14.2. 2)•New information regarding the safety of the IMP that indicates a change in the risk/benefit profile for the compound, such that the risk/benefit is no longer acceptable for subjects participating in the study. 3) Significant violation of Good Clinical Practice (GCP) that compromises the ability to achieve the primary study objectives or compromises subject safety. 4) If at the interim decision meeting prior to the next cohort the objectives of the study are considered to have been met.

If any of the above occurs, the study will be terminated if careful review of the overall risk/benefit analysis described in Section 6.4 demonstrates that the assumptions have changed and that the overall balance is no longer acceptable. In these circumstances termination can only take place with the agreement of the investigator and sponsor. The MHRA and EC will be informed of study termination.

If it becomes necessary to consider termination of the study after dosing has begun, dosing may be suspended pending discussion between the investigator and sponsor. Dosing will be stopped immediately on safety grounds.

The study may be terminated or suspended at the request of the MHRA or EC.

8.6 Lost to Follow-up: A subject will be considered lost to follow-up if they fail to return for scheduled visits and cannot be contacted by the clinical unit.

If a subject fails to return to the clinical unit for a required study visit: 1) The clinical unit must attempt to contact the subject and reschedule the missed visit as soon as possible. 2) Before a subject is deemed lost to follow-up, the investigator or designee must make every effort to regain contact with the participant (e.g. three telephone calls on three separate occasions and, if necessary, an email or letter to the participant's last known email/postal address). These contact attempts should be documented in the subject's source. 3) If the subject cannot be contacted, they will be considered lost to follow-up.

8.7 Treatment Assignment: This is a non-randomized study therefore a randomization schedule will not be produced. Instructions to dispense and dose will be produced prior to dosing with IMP, which will dictate the order in which the treatments should be administered to each subject. The instructions to dispense and dose will be retained in the ISF.

8.7.1 Subject Numbers: Subject numbers will be allocated on the morning of dosing according to the code 001 to 016 using the lowest number available. Replacement subjects will be allocated subject numbers 901 to 916, where the last two digits are the same as those of the original subject (e.g. if Subject 005 withdraws, the replacement will have the Subject Number 905 and will receive any regimens which Subject 005 did not receive in addition to any regimens which are required to make the required comparison[s] of interest).

8.7.2 Blinding: This is an open-label study and therefore blinding is not required.

9 Selection of Subjects: Subjects will be recruited from an existing subject panel or by direct advertising to the public. Before subjects are admitted to the clinical unit, The Over Volunteering Prevention System will be checked to ensure that each subject has not been dosed in a study within 90 days of the planned first dose date of this study.

9.1 Informed Consent: Subjects will be provided with a written explanation of the study at least the day before the screening visit. Additionally, subjects may be provided with an information video before the screening visit that introduces them to the study. In the video and/or during the screening visit, a physician or nurse will explain to each subject the nature of the study, its purpose, expected duration and the benefits and risks involved in study participation. Subjects will be informed that, for safety reasons, brief details of their involvement in the study may be revealed to other units and companies that carry out clinical studies nationally. Subjects will then be given the opportunity to ask questions and will be informed of their right to withdraw from the study without prejudice. After this explanation and before entering the study, the subject will voluntarily sign an informed consent form (ICF). Until written consent has been obtained from the subject no study specific procedure or investigation will be performed. If an amendment is made to the participant information sheet (PIS), participants will be re-consented to the most current version of the ICF(s) where appropriate.

9.2 Inclusion Criteria

Informed Consent and Compliance: 1) Must provide written informed consent. 2) Must be willing and able to communicate and participate in the whole study.

Demographics and Contraception: 3) Aged 18 to 55 years inclusive at the time of signing informed consent. 4) Must agree to adhere to the contraception requirements defined in Section 9.4.

Baseline Characteristics: 5) Males or non-pregnant, non-lactating females. 6) Participants who are healthy as determined by medical evaluation including medical history, physical examination, vital signs, single 12-lead ECG, clinical laboratory profiles (haematology, clinical chemistry and urinalysis), as deemed by the investigator or designee at screening. 7) Body mass index (BMI) of 18.0 to 32.0 kg/m2 as measured at screening. 8) Weight >50 kg at screening.

Other: 9) Willing to consume a high-fat breakfast, including pork.

Inclusion criteria 2 and 4 from the list above will be re-assessed at admission/pre-dose of Period 1.

9.3 Exclusion Criteria:

Medical/Surgical History and Mental Health: 1) Serious adverse reaction or serious hypersensitivity to any drug or formulation excipients. 2) Presence or history of clinically significant allergy requiring treatment, as judged by the investigator. Hay fever is allowed unless it is active. 3) History of clinically significant cardiovascular, renal, hepatic, dermatological, chronic respiratory or gastrointestinal disease, neurological or psychiatric disorder, as judged by the investigator. 4) Subjects with a history of cholecystectomy or gall stones.

Physical Examination: 5) Subjects who do not have suitable veins for multiple venipunctures/cannulation as assessed by the investigator or delegate at screening.

Diagnostic Assessments: 6) Clinically significant abnormal clinical chemistry, hematology or urinalysis as judged by the investigator (laboratory parameters are listed in Table 5). Subjects with Gilbert's Syndrome are allowed. 7) Positive hepatitis B surface antigen (HBsAg), hepatitis C virus antibody (HCV Ab) or human immunodeficiency virus (HIV) 1 and 2 antibody results. 8) Evidence of renal impairment at screening, as indicated by an estimated creatinine clearance (CLcr) of <80 mL/min using the Cockcroft-Gault equation. 9) Evidence of orthostatic hypotension, defined as a drop in systolic blood pressure >20 mmHg upon standing, a drop in diastolic blood pressure >10 mmHg on standing or an increase in heart rate >30 bpm on standing. Or symptomatic dizziness, pre-syncope or syncope during the assessment of orthostatic hypotension. 10) Any clinically significant abnormal finding on ECG at screening or pre-first dose. 11) Resting supine heart rate >90 bpm. 12) Resting supine systolic BP<90 mmHg. 13) Resting supine diastolic BP<50 mmHg. 14) Females who are pregnant or lactating (all female subjects must have a negative highly sensitive urine pregnancy test).

Prior Study Participation: 15) Subjects who have received any IMP in a clinical research study within the 90 days prior to Day 1 of Period 1, or less than 5 elimination half-lives prior to Day 1 of Period 1, whichever is longer. 16) Donation of blood or plasma within the previous 3 months or loss of greater than 400 mL of blood.

Prior and Concomitant Medication: 17) Subjects who are taking, or have taken, any prescribed or over-the-counter drug or herbal remedies (other than up to 4 g of paracetamol per day or HRT/hormonal contraception) in the 14 days before first IMP administration (see Section 11.4). COVID-19 vaccines are accepted concomitant medications. Exceptions may apply, as determined by the investigator, if each of the following criteria are met: medication with a short half-life if the washout is such that no PD activity is expected by the time of dosing with IMP; and if the use of medication does not jeopardize the safety of the trial subject; and if the use of medication is not considered to interfere with the objectives of the study. 18) Subjects who have had a COVID-19 vaccine 3 days before first dose.

Lifestyle Characteristics: 19) History of any drug or alcohol abuse in the past 2 years. 20) Regular alcohol consumption in males >21 units per week and in females >14 units per week (1 unit=½ pint beer, or a 25 mL shot of 40% spirit, 1.5 to 2 units=125 mL glass of wine, depending on type). 21) A confirmed positive alcohol breath test at screening or first admission. 22) Current smokers and those who have smoked within the last 12 months. 23) A confirmed positive urine cotinine test result at screening or first admission. 24) Current users of e-cigarettes and nicotine replacement products and those who have used these products within the last 12 months. 25) A confirmed positive drugs of abuse test result at screening or first admission (drugs of abuse tests are listed in Table 5).

Other: 26) Male subjects with pregnant or lactating partners. 27) Subjects who are, or are immediate family members of, a study site or sponsor employee. 28) Failure to satisfy the investigator of fitness to participate for any other reason.

Exclusion criteria 2, 9, 10, 11, 12, 13, 14, 15, 17, 18, 21, 23, 25, 26 and 28 from the list above will be re-assessed between admission and dose administration of Period 1.

Healthy subjects who do not meet the inclusion/exclusion criteria for the study will not be enrolled.

9.4 Contraception and Restrictions:

Male Subjects with Partners of Childbearing Potential. Male subjects who are sexually active with a partner of childbearing potential must use, with their partner, a condom plus an approved method of highly effective contraception from before the time of informed consent until 91 days after last IMP administration. This has been calculated based on 90 days (one cycle of spermatogenesis) plus 5 half-lives of the IMP. Five half-lives are calculated as approximately 1 day.

The following methods are acceptable:

Partner's use of combined (estrogen and progestogen-containing) hormonal contraception associated with inhibition of ovulation: 1) oral (must be in use for at least 1 complete cycle [e.g. 4 to 8 weeks] prior to first admission); 2) intravaginal (must be in use for at least 1 week prior to first admission); 3) transdermal (must be in use for at least 1 week prior to first admission).

Partner's use of progestogen-only hormonal contraception associated with inhibition of ovulation: 1) oral (must be in use for at least 1 complete cycle [e.g. 4 to 8 weeks] prior to first admission); 2) injectable/implantable (must be in use for at least 1 week prior to first admission); 3) intrauterine hormone-releasing system (must be in use for at least 1 week prior to first admission).

Partner's use of intrauterine device (must be in use for at least 1 week prior to first admission).

Vasectomized (must have been at least 6 months prior to first admission).

Partner's bilateral tubal occlusion (must have been at least 6 months prior to first admission).

These contraception requirements are considered to be more conservative than the guidance issued by the Heads of Medicines Agency: Clinical Trials Facilitation Group.

Males with Partners of Non-childbearing Potential: There is a significant risk of drug exposure through the ejaculate (which also applies to vasectomized males) that might be harmful to sexual partners. Therefore, even if a male is sexually active with a partner of non-childbearing potential they will be required to use a condom from first administration of IMP until the follow-up phone call.

Female Subjects of Childbearing Potential: Female subjects who are sexually active and of childbearing potential must use, with their partner, an approved method of highly effective contraception from before the time of informed consent until 31 days after last IMP administration. This has been calculated based on 30 days (one female menstrual cycle) plus 5 half-lives of the IMP. Five half-lives calculated as approximately 1 day.

The following highly effective methods are acceptable:

Combined (oestrogen and progestogen-containing) hormonal contraception associated with inhibition of ovulation: 1) oral (must be in use for at least 1 complete cycle [e.g. 4 to 8 weeks] prior to first admission); 2) intravaginal (must be in use for at least 1 week prior to first admission); 3) transdermal (must be in use for at least 1 week prior to first admission).

Progestogen-only hormonal contraception associated with inhibition of ovulation: 1) oral (must be in use for at least 1 complete cycle [e.g. 4 to 8 weeks] prior to first admission); 2) injectable/implantable (must be in use for at least 1 week prior to first admission); 3) intrauterine hormone-releasing system (must be in use for at least 1 week prior to first admission).

Intrauterine device (must be in use for at least 1 week prior to first admission).

Vasectomised partner (must have been at least 6 months prior to first admission).

Bilateral tubal occlusion (must have been at least 6 months prior to first admission).

Female Subjects are not required to use any of the above contraceptive methods if their sexual partner is female.

These contraception requirements are considered to be more conservative than the guidance issued by the Heads of Medicines Agency: Clinical Trials Facilitation Group.

All Male Subjects and Female Subjects of Childbearing Potential: Alternatively, sexual abstinence is considered a highly effective method only if defined as refraining from heterosexual intercourse during the entire period of risk associated with the study treatments. The reliability of sexual abstinence needs to be evaluated in relation to the duration of the clinical trial and the preferred and usual lifestyle of the subject.

Females of Non-Childbearing Potential: Female subjects who are not of childbearing potential do not need to use any methods of contraception. A woman is considered of childbearing potential unless post-menopausal or permanently sterile. Permanent sterilization methods include hysterectomy, bilateral salpingectomy and bilateral oophorectomy. A post-menopausal state is defined as no menses for 12 months without an alternative medical cause and confirmed by a follicle stimulating hormone (FSH) result of >40 IU/L.

9.4.1 Sperm Donation: Male subjects should not donate sperm for the duration of the study and for 91 days after last IMP administration.

9.4.2 Egg Donation: Female subjects should not participate in egg donation for the duration of the study and for 31 days after last IMP administration.

9.5 Pregnancy: Subjects will be instructed that if they/their partner becomes pregnant during the study this should be reported to the investigator. The investigator should also be notified of pregnancy occurring during the study but confirmed after completion of the study. In the event that a subject/subject's partner is subsequently found to be pregnant after the subject is included in the study, then consent will be sought from the subject/partner and, if granted, any pregnancy will be followed and the status of mother and/or child(ren) will be reported to Applicant after delivery. Any subject reporting a pregnancy during the study will be discontinued from the study treatment and every reasonable effort will be made to follow up the pregnancy until delivery.

A pregnancy notification form and follow-up will be completed.

9.6 Additional Study Restrictions: The following additional restrictions will be in place for the duration of the study:

1. Subjects must abstain from alcohol during the 24 h prior to screening and the 24 h prior to each admission until 48 h post-dose.

2. Subjects must not drink liquids or eat food containing cranberry, caffeine or other xanthines from 24 h prior to each admission until 48 h post-dose.

3. Subjects should refrain from eating food containing poppy seeds for 48 h prior to screening and for 48 h prior to each admission until 48 h post-dose.

4. Subjects must not take part in any unaccustomed strenuous exercise from the 72 h before the screening visit and then from 72 h prior to each admission until discharge from the study.

5. Must not donate blood or plasma (outside of this study), from screening, throughout the study duration, and for at least 90 days following last dose of study medication.

6. Subjects will be restricted to their bed for the first 4 h post-dose and thereafter encouraged to assume a standing posture in a gradual way before mobilizing, such as remaining seated for several minutes before standing, and then standing at the bedside for several minutes before proceeding to mobilize away from the bed area.

The additional restrictions above are not exclusion criteria; if non-compliance occurs, a protocol deviation will be completed.

10 Study Procedures: Study procedures will be performed as detailed in the study schedule of assessments in Table 6 and in accordance with SOPs unless otherwise stated in this protocol.

10.1 Screening: Within the 28 days preceding first dose, all subjects will be required to undergo a screening visit. Screening procedures will be carried out in accordance with the schedule of assessments.

If the start of the study is delayed for any reason so that the interval between screening and first dose exceeds 28 days, all or part of the screening procedures will be repeated at the discretion of the investigator.

Screening safety procedures such as safety bloods, ECGs, vital signs, urine cotinine tests, alcohol breath tests and urinalysis can be repeated as clinically indicated under the discretion of the investigator or sub-investigator if there is a concern regarding a subject's safety or eligibility to participate in the trial.

10.1.1 Subject Re-Screening: This study permits the re-screening of a subject who has discontinued the study as a pre-treatment failure (i.e. subject has not been treated); the reason for failure must be temporary and expected to resolve. If re-screened, the subject must be re-consented.

10.2 Admission and Pre-dose Procedures: The identity of the subjects will be confirmed at each admission and pre-dose.

In addition, the ongoing eligibility of subjects will be re-assessed at first admission/pre-dose, as described in Sections 9.2 and 9.3.

Admission/pre-dose safety procedures such as safety blood draws, ECGs, vital signs, urinalysis and drugs of abuse tests can be repeated as clinically indicated under the discretion of investigator or sub-investigator if there is a concern regarding a subject's safety or eligibility to participate in the clinical trial.

Reserve subjects for the first dose occasion, in any group, will not require admission procedures to be repeated, if dosing is within 2 days.

If dosing is delayed, subjects who have completed admission procedures do not need admission procedures to be repeated if dosing is within 2 days and the subjects have remained resident in the clinical unit.

The subjects will be admitted to the clinical unit in the evening on the day before dosing (Day −1).

In addition, subjects may be required to visit the clinical unit on Day −1 of each treatment period prior to admission to the clinical unit for SARS-CoV-2 antigen tests (if required; see Sections 6.4.2.2 and 14.5.8).

The admission and pre-dose procedures are presented in the schedule of assessments.

10.3 Study Day Procedures 10.3.1 Blood Volume: The number and timing of samples may be amended following any interim PK parameter estimations. However, in this case, the total blood volume for each subject will not exceed 550 mL in a 4-week period.

The first 0.5 mL of blood withdrawn via cannula will be discarded.

10.3.2 Timing of Procedures: There are times where the protocol requires more than one procedure to be completed at the same time point.

As guidance, the preferred order of assessments is: ECGs→Vitals→Nominal time PK blood sampling→Other assessments e.g. physical examinations. When scheduled at the same time point, ECGs should be taken prior to vital signs, and both ECGs and vital signs will be performed prior to the PK samples. Every effort will be made to take the PK sample at the protocol-specified time. Other assessments will be performed within the required time windows. All safety assessments will be timed and performed relative to the start of dosing.

10.3.3 Discharge from the Clinical Unit: A subject will be allowed to leave the premises without additional investigator or sub-investigator review, following completion of study-specific procedures at 48 h post-dose providing that: 1) No AEs have been reported during the study visit; and 2) The subject responds in the affirmative when asked if they are feeling well.

If any of these conditions are not met, then the subject will only be allowed to leave the clinical unit with the authorization of the investigator or sub-investigator.

There will be no continued provision of the study intervention or treatment for subjects as this study involves healthy volunteers only.

10.3.4 Medical Supervision: A physician will be responsible for the clinical aspects of the study and will be available at all times during the study. In accordance with the current Association of the British Pharmaceutical Industry guidelines, each subject will receive a card stating the telephone number of the investigator and the 24/7 contact details of the on-call physician.

10.3.5 Follow-up: A follow-up phone call will take place 3 to 7 days after the final dose to ensure the ongoing wellbeing of the subjects. If a subject reports any AEs which can present a cause for concern, they will be required to attend the clinical unit for a further follow-up assessment (as an unscheduled visit). Completion of the last follow-up phone call or unscheduled follow-up visit will be considered the end of the study.

11. Dosing of Subjects: Dosing will be performed at the time points detailed in the study schedule of assessments in Table 6.

11.1 Food and Fluid Intake: Subjects will be allowed water up to 1 h before the scheduled dosing time on Day 1 and will be provided with 240 mL of water at 1 h post-dose (to ensure adequate hydration) and thereafter, water will be allowed ad libitum after 1 h post-dose. Decaffeinated fluids will be allowed ad libitum from lunch time on the day of dosing.

If, for technical reasons, dosing is delayed for more than 2 h beyond the expected dosing time, subjects will receive 200 mL of an electrolyte drink (e.g. Lucozade Sport) at the originally scheduled dosing time, or earlier if possible.

Fed Dosing (Optional for Regimen F): The calorie/fat content of breakfast will be controlled for Regimen F, Day 1 if fed dosing is selected, adhering to the breakfast content detailed in Table 7. Subjects will be provided with a standardized menu for all other meals.

For the fed regimen, a high-fat breakfast will be given 30 min before dosing.

Subjects will be provided with a light evening snack and will fast from all food and drink (except water) for at least 8 h until the following morning, when they will be provided with a high-fat breakfast.

The breakfast should be consumed over a maximum period of 25 min, with dosing occurring 30 min (±5 min) after the start of breakfast. Subjects should be encouraged to eat their meal evenly over the 25 min period. It is acknowledged that some subjects will take less time to eat, but dosing should still occur 30 min (±5 min) after the start of breakfast. Subjects must consume at least 90% of the pre-dose breakfast in order to be eligible for dosing. The start and stop time and percentage of the breakfast consumed must be recorded in the source.

Lunch will be provided at approximately 4 h post-dose, an evening meal at approximately 10 h post-dose and an evening snack at approximately 14 h post-dose. On subsequent days, meals will be provided at appropriate times.

Fasted Dosing: The calorie/fat content of meals are not required to be controlled. Subjects will be provided with a standardized menu.

On Day −1 of Periods 1 to 5 and on Period 6 if fasted dosing is selected, subjects will be provided with a light snack and then fast from all food and drink (except water) for a minimum of 10 h prior to dosing until approximately 4 h post-dose at which time lunch will be provided. An evening meal will be provided at approximately 10 h post-dose and an evening snack at approximately 14 h post-dose. On subsequent days, meals will be provided at appropriate times.

11.2 Administration of Test Preparations: Specific details of IMP(s) and doses to be administered are provided in Section 5.2 and Section 8.1, respectively. Subjects will be dosed on the morning of Day 1 of each study period.

The exact time of dosing will be decided based on logistics and will be documented in the source. The order in which regimens are dosed may be subject to change due to logistical reasons.

The minimum washout period between regimens may be changed, if data collected during the study support the change. However, the minimum washout period will not be reduced to less than 5 half-lives of the IMP.

Subjects will receive a total of 5 administrations of MR oral formulations of minoxidil or a pharmaceutically acceptable salt thereof on 5 separate occasions and 1 administration of minoxidil or a pharmaceutically acceptable salt thereof tablet (reference) on 1 occasion.

Oral doses will be administered with a total of 240 mL of water. If required, additional water may be given with the IMP in 50 mL aliquots and will be recorded in the source but will not be classed as a protocol deviation.

11.3 Dosing Compliance: During all clinical phases of the study, subjects will be observed by study staff to assure compliance to all study procedures, including dose administration.

Mouth and hand checks will be conducted after dosing to ensure the tablet has been swallowed.

The date and time that each subject is dosed will be recorded in the subject's source data. Any violation of compliance will require evaluation by the investigator and sponsor to determine if the subject can continue in the study.

11.4 Prior and Concomitant Medications: No prescribed, over-the-counter medication or herbal remedies will be permitted from 14 days before first IMP administration until the follow-up phone call except up to 4 g of paracetamol per day and HRT/hormonal contraception and those deemed necessary by the investigator to treat AEs (exceptions may apply; see also Section 9.3). Any medications used will be recorded in the source.

COVID-19 vaccines are accepted concomitant medications. However, subjects are not to receive the COVID-19 vaccine within 3 days prior to first administration of IMP (see also Section 9.3), so that by the time of dosing any effects of the vaccine (e.g. pyrexia, fatigue, pain/stiffness at site of injection) are likely to have abated. Thereafter, it is preferable for subjects not to receive the vaccine within 72 h prior to administration of IMP, where possible; however, subjects may not be withdrawn on this basis.

Emergency equipment and drugs will be available within the clinical unit as per current standard procedures. In the unlikely event that they are required, their use will be documented.

Medication taken within 14 days of screening will be recorded in the source. Concomitant medications within 14 days of dosing will be included in the electronic case report form (eCRF).

12 Assessment of Efficacy: Not applicable for this Phase I study.

13 Assessment of Pharmacokinetics and Pharmacodynamics: PK assessments will be performed as detailed in the study schedule of assessments in Table 6.

13.1 Assessment of Pharmacokinetics: Venous blood samples will be collected from the subjects by a trained member of the clinical team. Consent will be collected from the subjects for use of these samples for the purposes of the proposed study. Samples will be processed to isolate plasma and PK analysis will be carried out on plasma samples.

Plasma samples will be sent for laboratory testing in linked anonymized form (subject number only). This information is able to be linked directly to the volunteer by the research team and study monitor, however not by the laboratory staff or sponsor.

Venous blood samples will be withdrawn via an indwelling cannula or by venipuncture at the time points detailed in the schedule of assessments.

All PK windows will be timed relative to the start of dosing.

The acceptable deviations from the nominal blood sampling times are as follows:

1) The pre-dose samples will be taken <1 h before dosing
2) 0 h to 1 h post-dose samples will be taken within ±2 min of the nominal post-dose sampling time
3) 1.5 h to 12 h post-dose samples will be taken within ±10 min of the nominal post-dose sampling time
4) 18 h to 48 h post-dose samples will be taken within ±30 min of the nominal post-dose sampling time The timing and number of the samples may be amended following any interim PK parameter estimations, including collection over a longer duration. Any changes to blood sampling time points would be documented in the interim dose decision report and retained in the ISF.

Samples will be collected into appropriate tubes as specified by the bioanalytical laboratory. Details of sample tubes and processing will be contained in the Clinical Sample Processing Manual (CSPM).

Samples will be shipped for the analysis of minoxidil or a pharmaceutically acceptable salt thereof.

13.2 Assessment of Pharmacodynamics: Not applicable for this Phase I study.

14 Assessment of Safety: Safety assessments will be performed as detailed in the study schedule of assessments in Table 6.

14.1 Definition and Classification of Adverse Events: An AE is any untoward medical occurrence in a subject that occurs either before dosing (referred to as a pre-dose AE) or once a medicinal product has been administered, including occurrences which are not necessarily caused by or related to that product.

An adverse drug reaction is any AE where a causal relationship with the IMP is at least a reasonable possibility (possibly related or related).

AEs will be monitored from the time the subject signs the ICF until discharge from the study at the follow-up phone call or unscheduled follow-up visit/phone call. The severity of AEs should be assessed as follows:

Mild: An AE that is easily tolerated by the subject, causes minimal discomfort and does not interfere with everyday activities.

Moderate: An AE that is sufficiently discomforting to interfere with normal everyday activities; intervention may be needed.

Severe: An AE that prevents normal everyday activities; treatment or other intervention usually needed.

14.2 Assessment of Causality: Every effort should be made by the investigator to try to explain each AE and assess its relationship, if any, to the IMP. The temporal relationship of the event to IMP administration should be considered in the causality assessment (i.e. if the event starts soon after IMP administration and resolves when the IMP is stopped).

Causality should be assessed using the following categories:

Unrelated: Clinical event with an incompatible time relationship to IMP administration, and that could be explained by underlying disease or other drugs or chemicals or is incontrovertibly not related to the IMP.

Possibly related: Clinical event with a reasonable time relationship to IMP administration, and that is unlikely to be attributed to concurrent disease or other drugs or chemicals.

Related: Clinical event with plausible time relationship to IMP administration and that cannot be explained by concurrent disease or other drugs or chemicals.

The degree of certainty with which an AE is attributed to IMP administration (or alternative causes, e.g. natural history of the underlying disease, concomitant therapy) will be determined by how well the experience can be understood in terms of one or more of the following:

1) Known pharmacology of the IMP
2) Reactions of a similar nature have been previously observed with the IMP or this class of drug
3) The experience being related by time to IMP administration, terminating with IMP withdrawal or recurring on re-challenge
4) Alternative cause 14.3 Recording Adverse Events: AEs (including SAEs) will be recorded from the time of providing written informed consent until discharge from the study at the follow-up phone call or unscheduled follow-up visit/phone call. During each study visit the subject will be questioned directly regarding the occurrence of any adverse medical event according to the schedule in the source. All AEs, whether ascribed to study procedures or not, will be documented immediately in the subject's source. This will include the date and time of onset, a description of the AE, severity, seriousness, duration, actions taken, outcome and an investigator's current opinion on the relationship between the study drug and the event. A diagnosis and final opinion on the relationship between the study drug and the event will be provided at the end of the study by the investigator.

Any subject who withdraws from the study due to an AE will be followed up until the outcome is determined and written reports are provided by the investigator.

14.4 Serious Adverse Events 14.4.1 Definition of Serious Adverse Events: A SAE is defined as any untoward medical occurrence that at any dose:

1) Results in death
2) Is life-threatening
3) Requires hospitalization or prolongation of existing hospitalization
4) Results in persistent or significant disability or incapacity
5) Consists of a congenital anomaly or birth defect
6) An important medical event as recognized by the investigator 14.4.2 Definition of Suspected Unexpected Serious Adverse Reactions: Suspected unexpected serious adverse reactions (SUSARs) are AEs that are believed to be related to an IMP and are both unexpected (i.e. the nature or severity is not expected from the information provided in the IB) and serious. SUSARs are subject to expedited reporting to the MHRA (see Section 16.3.2 for details on reporting SUSARs).

14.5 Laboratory Measurements: Venous blood, samples will be collected from the subjects by a trained member of the clinical team. Consent will be collected from the subjects for use of these samples for the purposes of the proposed study.

Blood and urine samples are sent for laboratory testing in linked anonymized form (subject number, gender and date of birth for analytical reasons). This information is able to be linked directly to the volunteer by the research team and study monitor; however, not by the laboratory staff or sponsor.

Safety laboratory tests and virology will be carried out on blood samples, and drugs of abuse tests and urinalysis will be carried out on urine samples. The research will not involve analysis or use of human DNA.

Blood and urine samples results will be reviewed by a physician and acted upon before the subject is dosed or receives their next dose, or is released from the study, as is appropriate. A list of the laboratory parameters measured is presented in Table 5.

14.5.1 Hematology and Clinical Chemistry: Laboratory tests will be performed by The Doctors Laboratory at the time points detailed in the schedule of assessments. Blood samples will be collected and processed as detailed in the CSPM. Scheduled blood samples will be taken following an 8 h fast.

The acceptable deviations from the nominal blood sampling time points for laboratory assessments are:

1) The pre-dose blood sample will be taken <2 h before dosing
2) Post-dose blood samples will be taken ±1 h from the nominal blood sampling time CLcr will be calculated at screening by The Doctors Laboratory (TDL) using the Cockcroft-Gault equation and body weight.

14.5.2 Virology: HBsAg, HCV Ab and HIV 1 and 2 tests will be performed from the clinical chemistry sample (see Section 14.5.1 for sample collection and processing information).

14.5.3 Urinalysis: Urinalysis will be performed on-site using a dipstick at the time points detailed in the schedule of assessments. Urine samples will be collected and processed as detailed in the CSPM. If microscopy is required, a urine sample will be sent to The Doctors Laboratory.

The acceptable deviations from the nominal urine sampling time points for urinalysis are:

Post-dose urine samples will be taken ±2 h from the nominal urine sampling time 14.5.4 Pregnancy Test Urine highly sensitive pregnancy tests will be performed at the time points detailed in the schedule of assessments. The samples will be collected and processed as detailed in the CSPM.

14.5.5 Follicle-Stimulating Hormone Test: Serum FSH tests will be performed at the time point detailed in the schedule of assessments for female subjects who declare that they are post-menopausal. The samples will be collected and processed as detailed in the CSPM.

14.5.6 Cotinine and Drug Screen: A urine cotinine and drug screen will be performed on-site using a point of care testing method (e.g. Alere Drug Screen Test Cup) at the time points detailed in the schedule of assessments. The sample will be collected and processed as detailed in the CSPM. Subjects will be screened for the drugs of abuse listed in Table 5.

14.5.7 Alcohol Breath Test: An alcohol breath test will be performed at the time points detailed in the schedule of assessments. A confirmed positive result will exclude the subject from dosing during that admission.

14.5.8 SARS-CoV-2 Tests (If Required): Testing for the SARS-CoV-2 virus may be performed based on current infection rates and availability of tests. If required, the samples will be collected and processed as detailed in the Screening Sample Processing Manual and CSPM, as applicable.

Testing time points may be changed, and additional time points may be added throughout the study as required. The decision on COVID-19 testing and the definition of the testing time points are subject to change based on the current risk mitigation in place and will be agreed by the study team and documented in the ISF via the Clinical Kick-Off Meeting minutes or in a file note if the study is ongoing.

14.5.9 Abnormal Laboratory Findings: In cases where laboratory findings are outside the normal range and the investigator believes that the results may be of clinical significance, repeat sampling may be requested as clinically indicated. If the abnormal finding is clinically significant, appropriate actions will be taken e.g. the subject will not be entered into the study or the subject may be withdrawn from the study. The subject will be referred to their general practitioner or other appropriate provider for further care if necessary. The same will apply if the results of the HBsAg, HCV Ab or HIV test are positive and in addition the investigator will ensure that adequate counselling is available if requested.

Abnormal results at follow-up assessments will also require repeat testing if the investigator believes the results may be of clinical significance.

Any clinically significant abnormality, including changes from baseline, must be reported as an AE.

Additional blood and/or urine samples may be taken for safety tests. Furthermore, additional assays outside those specified in the protocol may be performed for safety reasons as requested by the investigator or sub-investigator.

14.6 Vital Signs Measurements: At screening and Period 1 pre-dose only, two blood pressure and heart rate measurements will be measured by an automated recorder; 1 supine and 1 standing (orthostatic). The first supine measurement will be performed after the subject has rested in a supine position for at least 5 min. The subject will then sit for at least 1 min, then stand for at least 2 minutes. The second, standing BP and HR measurements will be performed after the subject has been standing for at least 2 min but no longer than 3 min.

Blood pressure and heart rate will be measured by an automated recorder after the subject has been in a supine position for a minimum of 5 min, at the timepoints detailed in the schedule of assessments.

Respiratory rate and oxygen saturations (SaO2) will also be recorded at each supine vital sign measurement. Oral temperature will be recorded at screening and pre-dose.

The acceptable deviations from the nominal vital signs measurement time points are:

1) The pre-dose vital signs measurements will be taken <2 h before dosing.
2) Post-dose vital signs measurements will be taken ±15 min from the nominal post-dose time points.
3) Discharge vital signs measurements will be taken ±1 h from the nominal time point.

If a subject shows an abnormal assessment at any stage, repeat measurements may be made and the abnormality followed to resolution if required. Additional measurements may be taken as deemed necessary by the investigator or sub-investigator.

Any new or worsening clinically significant abnormality, including changes from baseline, must be reported as an AE.

14.7 ECG Measurements: Single 12-lead ECGs will be measured after the subject has been in the supine position for a minimum of 5 min at the time points detailed in the schedule of assessments. The acceptable deviations from the nominal ECG measurement time points are:

1) The pre-dose ECG measurements will be taken <2 h before dosing
2) Post-dose ECG measurements will be taken ±15 min from the nominal post-dose time point.
3) Discharge ECG measurements will be taken ±1 h from the nominal time point.

If a subject shows an abnormal assessment at any stage, repeat measurements may be made and the abnormality followed to resolution if required. Additional measurements may be taken as deemed necessary by the investigator or sub-investigator.

Any new or worsening clinically significant abnormality, including changes from baseline, will be reported as an AE.

14.8 Body Weight, Height and BMI: The subject's body weight and height will be measured and their BMI will be calculated at screening. Body weight will be reported at the time points detailed in the schedule of assessments.

14.9 Physical Examination: Subjects will undergo a physical examination at the time points detailed in the schedule of assessments.

In the targeted (symptom driven) physical examination, a physician will assess the subject; if the subject reports feeling unwell or has ongoing AEs, then the physician will examine the appropriate body system(s) if required.

14.10 Additional Safety Procedures: Additional non-invasive procedures that are already specified in the protocol may be performed, if it is believed that an important effect of the IMP(s) is occurring or may occur at a time when no measurements are scheduled, or if extra procedures are needed in the interests of safety.

Additional blood samples for safety assessments may be taken if required by the investigator or sub-investigator at any point.

15 Statistics and Data Analysis 15.1 Sample Size Justification: The study is exploratory and no formal sample size calculation has been made. Based on experience from previous studies of a similar design, a sample size of 16 subjects to obtain 12 evaluable subjects is considered sufficient to meet the objectives of the study.

15.2 Data Management: Data management will be performed by the trial site.

Study data will be managed using a validated eCRF database system and subjected to data consistency and validation checks. Data queries will be raised within the study eCRF database by data management staff and resolved with the assistance of clinical staff.

AEs, medical histories and medications will be coded using the Medical Dictionary for Regulatory Activities (version to be specified in the Data Management Plan [DMP]) and the World Health Organization, Drug Dictionary Global Drug Reference (version to be specified in the DMP), respectively. An independent coding review will also be performed within the Data Sciences department.

Clinical chemistry and hematology data (and other safety laboratory data) will be collected by a central laboratory (The Doctors Laboratory) and stored electronically in their clinical pathology system. The data will be transferred electronically to the trial site and all demographic details and sample dates will be cross-referenced with the corresponding data on the study database. All queries will be resolved with the assistance of laboratory staff, or if necessary, clinical staff.

The database will be closed after all queries have been resolved. The database will be locked when all criteria listed in the DMP are met.

Further details are addressed in the DMP.

15.3 Pharmacokinetic Data Analysis: The plasma concentration data for minoxidil or a pharmaceutically acceptable salt thereof provided by the trial site will be analyzed using Phoenix WinNonlin v8.3 or a more recent version (Certara USA, Inc., USA).

PK analysis of the concentration time data obtained will be performed using appropriate non-compartmental techniques to obtain estimates of the PK parameters presented in Table 4, where possible and appropriate.

TABLE 4

Plasma Pharmacokinetic Parameters

| Parameter | Definition |
|---|---|
| Tlag | Time prior to the first measurable concentration |
| Tmax | Time of maximum observed concentration |
| Cmax | Maximum observed concentration |
| C24 | Concentration at 24 h post-dose |
| AUC(0-last) | Area under the curve from time 0 to the time of last measurable concentration |

TABLE 4-continued

| Plasma Pharmacokinetic Parameters | |
|---|---|
| Parameter | Definition |
| AUC(0-inf) | Area under the curve from time 0 extrapolated to infinity |
| AUCextrap | Area under the curve from time of the last measurable concentration to infinity as a percentage of the area under the curve extrapolated to infinity |
| T½ | Terminal elimination half-life |
| Lambda-z | First order rate constant associated with the terminal (log-linear) portion of the curve |
| MRT(0-last) | Mean residence time from time 0 to time of the last measurable concentration |
| MRT(0-inf) | Mean residence time from time 0 extrapolated to infinity |
| Frel Cmax | Relative bioavailability based on Cmax |
| Frel AUC(0-last) | Relative bioavailability based on AUC(0-last) |

Interim PK parameter estimations will be provided for dose, formulation and prandial state selection purposes, as described in Section 8.2.

Further details of the PK data analysis will be included in the Reporting and Analysis Plan (RAP).

15.4 Statistical Data Analysis: Statistical analysis and production of summary tables, figures and listings for this study will be performed by the trial site using the statistical package SAS (v9.4 or more recent version).

In general terms, categorical data (including treatment-emergent AEs) will be presented using counts and percentages, while continuous variables will be presented using the mean, median, standard deviation (SD), minimum and maximum. Additional statistics will be provided for PK-related data including coefficient of variation (CV %), geometric mean, geometric SD and geometric CV %.

Descriptive summaries for all safety data (AEs, vital signs, ECGs and safety laboratory assessments) by regimen will be provided (including changes from baseline as appropriate).

Descriptive summaries for all PK data by regimen will be provided.

All safety and PK data will be listed.

In addition, formal statistical analysis will be performed on the PK parameters Cmax, AUC(0-last) and AUC(0-inf) to assess relative bioavailability between test and reference formulations, and potentially to assess for the effect of food on a selected prototype. The PK parameters will undergo a natural logarithmic transformation and will be analyzed using a mixed effects model, with terms for regimen as a fixed effect and subject as a random effect. Adjusted geometric mean ratios (GMRs) and 90% confidence intervals for the adjusted GMRs for the comparisons between each of the test formulations and the reference formulation will be provided, where the ratios are defined as test/reference.

The comparisons of interest are planned to be but not limited to:

1) Regimen A vs Regimen B
2) Regimen C vs Regimen B
3) Regimen D vs Regimen B
4) Regimen E vs Regimen B
5) Regimen F vs Regimen B (if applicable)

If the fed dosing option is chosen for Regimen F, formal statistical analysis will be performed on the PK parameters Cmax, AUC(0-last) and AUC(0-inf) to assess for the effects of food. The mixed model will be as described above for the comparison of fed versus fasted.

Formal statistical analysis may also be performed on the log-transformed PK parameters Cmax, AUC(0-last) and AUC(0-inf) to assess dose proportionality. This will be assessed using a mixed effects model, including log dose as a fixed effect and subject as a random effect.

Populations and analysis sets will be determined for safety and PK data after database lock using the criteria defined in the RAP; the RAP will be signed off prior to database lock. All populations and analysis sets will be defined after database lock when the relevant data are available.

Further details relating to the statistical analysis will be included in the RAP including the following:

1) Criteria to be used to define each of the population and analysis sets
2) Additional detail covering the analyses and/or description of primary and secondary analyses and safety data
3) Handling of missing data, unused or spurious data
4) Handling of data from withdrawn subjects 15.5 Interim Analysis: No formal interim analyses are planned for this study. Interim data reviews will be performed as detailed in Section 8.2.

16 Safety Reporting to Regulatory Authorities and Ethics Committees 16.1 Events Requiring Expedited Reporting: SUSARs (as defined in Section 14.4.2) are subject to expedited reporting to the appropriate regulatory authority.

In addition to SUSARs, other safety issues may qualify for expedited reporting where they might materially alter the current benefit-risk assessment of an IMP or that would be sufficient to consider changes in the IMPs' administration or in the overall conduct of the study, for instance:

1) An increase in the rate of occurrence or a qualitative change of an expected serious adverse reaction, which is judged to be clinically important
2) SAEs that occur after the subject has completed the clinical study where Applicant considers them to be a SUSAR
3) New events related to the conduct of the study or the development of the IMPs and likely to affect the safety of the subjects, such as:

A. An SAE which could be associated with the study procedures and which could modify the conduct of the study
B. A major safety finding from a newly completed animal study (such as carcinogenicity)
C. Any anticipated end or temporary halt of a study for safety reasons and conducted with the same IMPs in another country by the same sponsor 16.2 Urgent Safety Measures If the trial site or any of its staff or contractors becomes aware of an actual or potential urgent safety issue, then Applicant must be immediately contacted so that appropriate urgent safety measures can be agreed. An urgent safety issue is defined as:

1) An immediate hazard to the health or safety of subjects participating in a clinical study
2) A serious risk to human health or potentially a serious risk to human health An urgent safety issue may include issues with an investigational drug or comparators, study procedures, intercurrent illness (including pandemic infections), concomitant medications, concurrent medical conditions or any other issues related to the safe conduct of the study or that pose a risk to study subjects.

In exceptional circumstances of imminent hazard and in order to safeguard the health or safety of individuals, the trial site may take urgent safety measures before informing Applicant, but Applicant must be informed immediately after the hazard has resolved.

The sponsor is responsible for informing the appropriate regulatory authorities and the EC; the task of reporting urgent safety measures will be delegated to the trial site.

16.3 Reporting 16.3.1 Reporting Serious Adverse Events: The investigator must notify the study sponsor and pharmacovigilance provider of any SAE or serious adverse reaction immediately, and in all cases within 24 h of becoming aware of the event or reaction. A copy of the written report of the event should promptly be sent to the study sponsor for information purposes, in accordance with International Council for Harmonization of Technical Requirements for Pharmaceuticals for Human Use (ICH) guidelines for GCP.

16.3.2 Reporting of Suspected Unexpected Serious Adverse Reactions: It is the responsibility of Applicant to determine whether a reported SAE fits the classification of a SUSAR and to notify the investigator of their decision as soon as possible.

16.3.3 Expedited Reporting of Events: It is the responsibility of Applicant to determine whether an event requires expedited reporting and to notify the investigator of their decision as soon as possible.

Where expedited reporting is required, the following procedures should be followed.

Fatal or life-threatening SUSARs: It is the responsibility of Applicant to report fatal or life-threatening SUSARs to the MHRA as soon as possible, but no later than 7 calendar days after they first became aware of the reaction. Any additional relevant information should be sent within 8 days of the report. The task of reporting fatal or life-threatening SUSARs may be delegated to the pharmacovigilance provider. A separate notification to the EC is not required.

Other SUSARs: It is the responsibility of Applicant to report other SUSARs to the MHRA as soon as possible, but no later than 15 calendar days after they first became aware of the reaction. The task of reporting other SUSARs may be delegated to the pharmacovigilance provider. A separate notification to the EC is not required.

16.3.4 Reporting of Urgent Safety Measures: The trial site is required to notify the MHRA and the EC of an urgent safety measure immediately by telephone and follow-up in writing within 3 calendar days from the date the measures are taken.

16.3.5 Reporting of COVID-19 Vaccine-Related Adverse Events: AEs considered by the investigator to be related to COVID-19 vaccines will be reported to the MHRA via the Yellow Card system.

16.4 Serious Breaches: It is the responsibility of Applicant to notify the MHRA of any serious breach, which is likely to affect, to a significant degree, the safety or mental integrity of the subjects of the study or the scientific value of the study.

All serious breaches will be notified to the MHRA within 7 days. The reporting will be performed by the party who suspects the serious breach.

17 Protocol Amendments and Deviations 17.1 Amendments: After the protocol has been submitted to the MHRA and EC, any amendment must be agreed by the investigator after discussion with Applicant and will be formally documented.

All substantial amendments will be submitted to the MHRA and/or EC for approval and/or an opinion, respectively, as required by current regulations.

If the PIS and ICF are updated as a result of the substantial amendment, the new approved versions will be used to re-consent currently enrolled subjects and must be provided to newly enrolled subjects prior to their entry into the study.

17.2 Protocol Deviations: The study must be conducted in accordance with the Clinical Protocol. Should a protocol deviation occur, it must be promptly assessed in order to decide whether any of these non-compliances should be reported to the MHRA as a serious breach of GCP and the Clinical Protocol.

Protocol waivers are not acceptable.

Deviations from the protocol will be recorded in the source as noted by the clinical staff. If necessary, Applicant will be informed of the deviation.

Any protocol deviations assessed as major will be discussed with Applicant in order to determine if the withdrawal criteria stated in Section 8.3 have been met.

18 Regulatory 18.1 Compliance: This study will be conducted in accordance with the protocol and with the following legislation:

1) ICH GCP Guidelines approved by the Committee for Medicinal Products for Human Use (CHMP) on 17 Jul. 1996, which came into force on 17 Jan. 1997, updated July 2002, Integrated Addendum E6 (R2) dated 9 Nov. 2016.
2) ICH E8 (R1) General Considerations for Clinical Studies, dated October 2021.
3) The Medicines for Human Use (Clinical Trials) Regulations. Statutory Instruments 2004 No. 1031.
4) The Medicines for Human Use (Clinical Trials) Amendment Regulations. Statutory Instruments 2006 No. 1928.
5) The Medicines for Human Use (Clinical Trials) Amendment (No. 2) Regulations. Statutory Instruments 2006 No. 2984.
6) The Medicines for Human Use (Clinical Trials) Amendment Regulations. Statutory Instruments 2008 No. 941.
7. The Medicines for Human Use (Clinical Trials) (Amendment) (EU Exit) Regulations. Statutory Instruments 2019 No. 744.

In addition, the study will be performed according to the ethical principles outlined in the World Medical Association Declaration of Helsinki and its amendments.

18.2 MHRA and Ethical Approval: Prior to the initiation of the study, the clinical trial of an investigational medicinal product (CTIMP) application, the protocol and associated documentation must be approved by the MHRA and given a favorable opinion by an EC. A copy of this written approval and any correspondence with the MHRA and EC will be available at the clinical site and will be provided to Applicant.

18.3 Source Data: A study-specific source document identification list will be finalized with Applicant prior to the start of the clinical phase of the study. The document will identify what data should be considered source data for this study.

For this study, electronic data capture will be used where possible and data will be automatically recorded into an eCRF. In instances where paper source documents are used, data to be transcribed into the eCRF will be identified using a Source Document Identification List, as governed by the trial site's SOPs.

18.4 Declaration of the End of the Study: The end of the study is defined as the last visit of the last subject (e.g. follow-up phone call or unscheduled visit/phone call). Any changes to this definition will be notified as a substantial amendment (see Section 17.1).

The EC and MHRA should be notified of the conclusion of the study within 90 days of the end of the study, or within 15 days if the study is terminated early, clearly explaining the reasons for the termination.

TABLE 5

| Clinical Laboratory Parameters | | | | |
|---|---|---|---|---|
| Hematology | Clinical Chemistry | Virology | Urinalysis | Drugs of Abuse |
| Hemoglobin<br>Hematocrit (HCT; packed cell volume [PCV])<br>Red blood cell (RBC; erythrocyte) count<br>Mean corpuscular volume (MCV)<br>Mean corpuscular hemoglobin (MCH)<br>Mean corpuscular hemoglobin concentration (MCHC)<br>Platelet count<br>White blood cell (WBC; leukocytes) count<br>Neutrophils<br>Lymphocytes<br>Monocytes<br>Eosinophils<br>Basophils | Sodium<br>Potassium<br>Chloride<br>Bicarbonate<br>Urea<br>Creatinine<br>CLcr will be calculated at screening using the Cockcroft-Gault equation<br>Bilirubin (total)<br>Bilirubin (direct; only if total is elevated)<br>Alkaline phosphatase<br>Aspartate aminotransferase (AST)<br>Alanine aminotransferase (ALT)<br>Gamma glutamyl transferase (GGT)<br>Protein (Total)<br>Albumin<br>Calcium<br>Glucose (fasting)<br>Glucose<br>Follicle stimulating hormone (FSH; female subjects who declare that they are post-menopausal) | Hepatitis B surface antigen<br>Hepatitis C virus antibody<br>HIV 1 & 2 antibodies<br>If Required:<br>SARS-CoV-2 antigen | Bilirubin<br>Urobilinogen<br>Ketones<br>Glucose<br>Protein<br>Blood<br>Nitrites<br>pH<br>Specific gravity<br>Leukocytes<br>At discretion of investigator based on urinalysis results<br>Microbiology<br>Urine microscopy<br>Urine Pregnancy<br>Human chorionic gonadotropin (hCG) (all female subjects) | Amphetamines<br>Barbiturates<br>Benzodiazepines<br>Cocaine<br>Cotinine<br>Marijuana/cannabis<br>Methadone<br>Methamphetamine/ecstasy<br>Morphine/opiates<br>Phencyclidine<br>Tricyclic antidepressants |

TABLE 6

| Schedule of Assessments | | | | | | | | | | | | | | | | | | | | | | |
|---|---|---|---|---|---|---|---|---|---|---|---|---|---|---|---|---|---|---|---|---|---|---|
| | | | Periods 1 to 6 | | | | | | | | | | | | | | | | | | | Final Period |
| | Study Day | | | | | | | | | | | | | | | | | | | | | |
| | −28 to −2 | −1 | | | | | | | 1 | | | | | | | | | | 2 | | 3 | 4 to 8 |
| | | | Pre- | Times After Dosing (h) | | | | | | | | | | | | | | | | | | Follow- |
| | Screening | Admission | dose | 0 | 0.2 | 0.5 | 0.7 | 1 | 1.5 | 2 | 3 | 4 | 6 | 8 | 10 | 12 | 18 | 24 | 30 | 36 | 48 | up |
| General Assessments | | | | | | | | | | | | | | | | | | | | | | |
| Informed Consent | X | | | | | | | | | | | | | | | | | | | | | |
| Medical History | X | Xb | | | | | | | | | | | | | | | | | | | | |

TABLE 6-continued

Schedule of Assessments

| | | | | | | | | | | | | | | | | | | | | | | Final Period |
|---|---|---|---|---|---|---|---|---|---|---|---|---|---|---|---|---|---|---|---|---|---|---|
| | | | Periods 1 to 6 | | | | | | | | | | | | | | | | | | | |
| | Study Day | | | | | | | | | | | | | | | | | | | | | |
| | −28 to −2 | −1 | 1 | | | | | | | | | | | | | | | | 2 | | 3 | 4 to 8 |
| | | | Pre- | Times After Dosing (h) | | | | | | | | | | | | | | | | | | Follow- |
| | Screening | Admission | dose | 0 | 0.2 | 0.5 | 0.7 | 1 | 1.5 | 2 | 3 | 4 | 6 | 8 | 10 | 12 | 18 | 24 | 30 | 36 | 48 | up |
| Weight, Height and BMI | X | Xc | | | | | | | | | | | | | | | | | | | Xc | |
| Vein Assessment | X | | | | | | | | | | | | | | | | | | | | | |
| Urine Cotinine Test | X | X | | | | | | | | | | | | | | | | | | | | |
| Drug Screen | X | X | | | | | | | | | | | | | | | | | | | | |
| Alcohol Breath Test | X | X | | | | | | | | | | | | | | | | | | | | |
| IMP Administration[d] | | | | X | | | | | | | | | | | | | | | | | | |
| Safety Assessments | | | | | | | | | | | | | | | | | | | | | | |
| Physical Examination | X | | | | | | | | | | | | | | | | | | | | | |
| Targeted (symptom driven) Physical Examination[e] | | | X | | | | | | | | | | | | | | | | | | X | |
| Safety Blood Samples[f] | X | | X | | | | | | | | | | | | | | | | | | X | |
| CLcr | X | | | | | | | | | | | | | | | | | | | | | |
| Urinalysis | X | X | | | | | | | | | | | | | | | | | | | X | |
| Urine Pregnancy Testg | X | X | | | | | | | | | | | | | | | | | | | | |
| Single 12-Lead ECGs | X | | X | | | X | | X | | X | | X | | X | | | | X | | | X | |
| Supine and Standing Vital Signs[h] | X | | Xi | | | | | | | | | | | | | | | | | | | |
| Vital Signsj | | | Xk | | | X | | X | | | | X | | X | | | | X | | | X | |
| Adverse Events | | | < ---------------------------------------------------------------- X ---------------------------------------------------------------- > | | | | | | | | | | | | | | | | | | | |
| Prior and Concomitant Medication | | | < ---------------------------------------------------------------- X ---------------------------------------------------------------- > | | | | | | | | | | | | | | | | | | | |
| PK Assessments | | | | | | | | | | | | | | | | | | | | | | |
| Plasma Samples for minoxidil or a pharmaceutic | | | X | | X1 | X | X1 | X | X | X | X | X | X | X | X | X | X | X | X | X | X | |

TABLE 7

| Breakfast Content (Fed Dosing) | | | |
|---|---|---|---|
| Meal Description | Total Energy (kcal) | Energy from Fat (%) | Composition |
| High-Fat Breakfast (FDA approved)[a] | 951 | 58 | 1 (40 g) hash brown, 2 (80 g) Unsmoked Rindless Streaky Bacon, 1 medium (45 g) egg fried in 10 g of butter, 2 slices (95 g) of white sliced bread with 20 g of butter, 240 mL of full fat milk |

Example 6: Modified Release Minoxidil or a Pharmaceutically Acceptable Salt Thereof Formulations Compositions of MR oral formulations of minoxidil or a pharmaceutically acceptable salt thereof are provided in Table 8.

characterized by a high/fast dissolution profile. Batches of prototype C tested at day 0 and day 7 demonstrate similar dissolution profiles.

Figure 5:
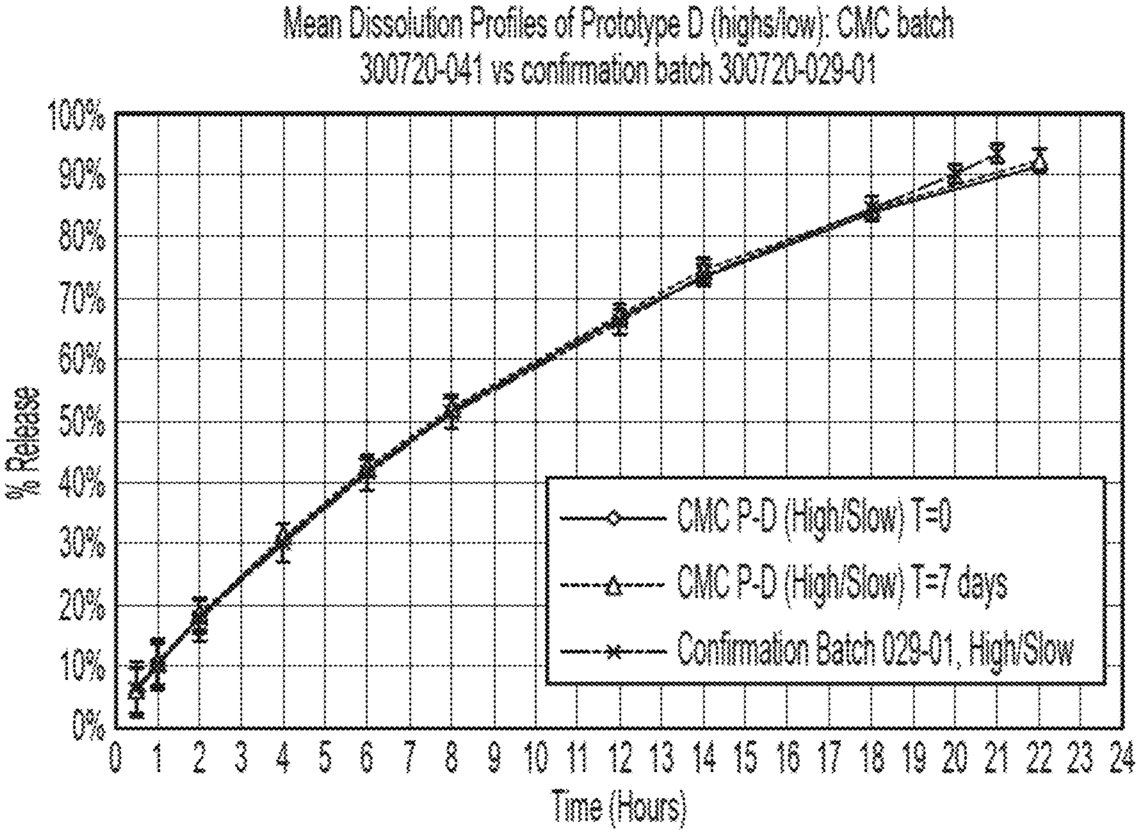
FIG. 5 depicts a mean dissolution profile of a pharmaceutical formulation, prototype D, under single stage dissolution (pH 7.2 phosphate buffer, USP II, 75 rpm (+infinity spin)). Prototype D (batch no. 300720-041, n=6) at T=0 days and T=7 days vs. reference batch (batch no. 300720-029-01, n=3).

Prototype D releases approximately 50% minoxidil or a pharmaceutically acceptable salt thereof by about 8 hours in a single stage dissolution assay (FIG. 5; pH 7.2 phosphate buffer, USP II, 75 rpm (+infinity spin)). Prototype D is characterized by a high/fast dissolution profile. Batches of prototype D tested at day 0 and day 7 demonstrate similar dissolution profiles.

Example 7: Dissolution Profiles for Modified Release Formulation

Figure 6:
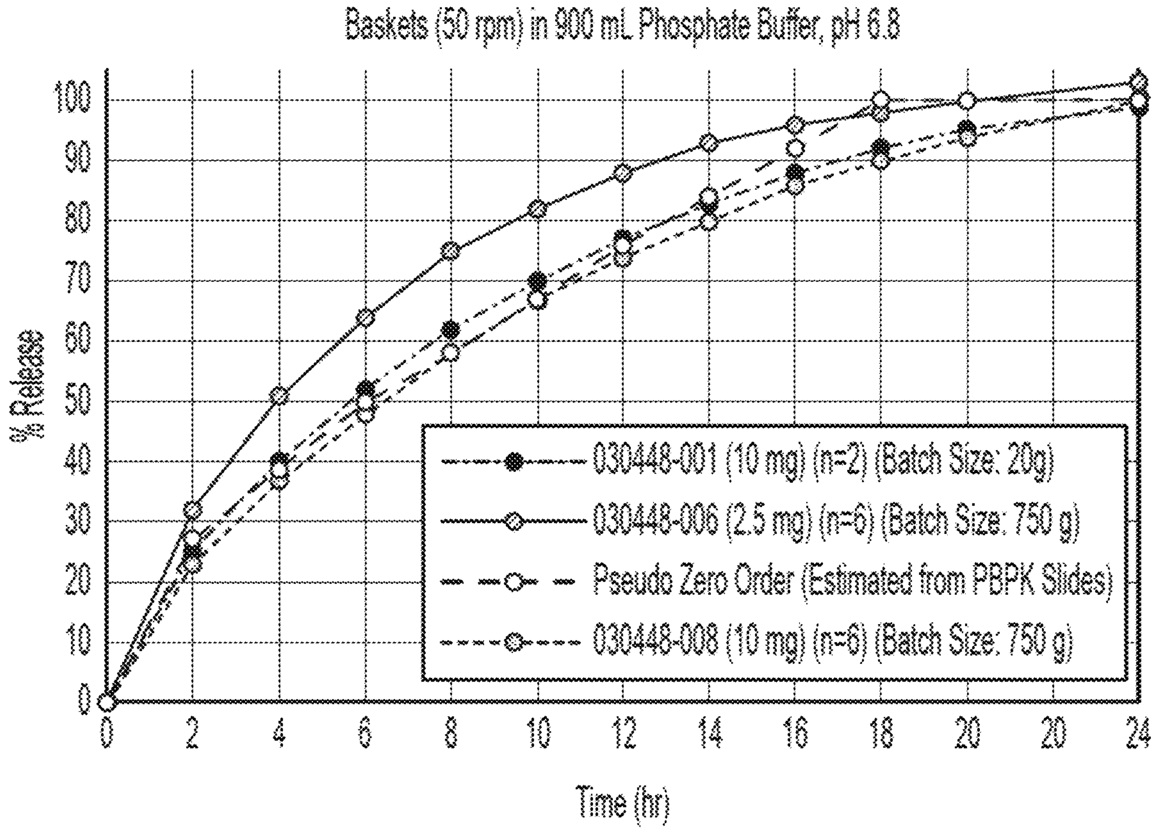
FIG. 6 depicts dissolution of prototype batches comprising 10 mg minoxidil vs. 2.5 mg minoxidil.

Dissolution of 10 mg prototype batch (Batch Nos. 030448-008, n=6, and 030448-001, n=2; 1-stage dissolution) is slower than a 2.5 mg prototype batch (Batch No. 030448-005, n=6) with an f2=40.8%. The 10 mg prototype formulation exhibits pseudo zero order kinetics (Table 9 and FIG. 6). Dissolution was performed in 900 mL phosphate buffer, pH 6.8 (50 rpm).

TABLE 8

MR Oral Formulations of Minoxidil or a Pharmaceutically Acceptable Salt thereof

| Component | Quantity per Tablet (mg): Prototype A Slow Release, Low Dose | Prototype B Fast Release, Low Dose | Prototype C Fast Release, High Dose | Prototype D Slow Release, High Dose | Function | Reference to Standard |
|---|---|---|---|---|---|---|
| Minoxidil or a pharmaceutically acceptable salt thereof Drug Substance[1] | 2.000 | 2.000 | 10.000 | 10.000 | Active | USP |
| HPMC K4M | 0.000 | 45.000 | 30.000 | 0.000 | Release Modifier | Ph. Eur., JP, USP |
| HPMC K200M | 120.000 | 0.000 | 0.000 | 105.000 | Release Modifier | Ph. Eur., JP, USP |
| Microcrystalline Cellulose | 26.950 | 50.975 | 54.475 | 33.950 | Filler | Ph. Eur., JP, NF |
| Lactose Monohydrate | 0.000 | 50.975 | 54.475 | 0.000 | Release Modifier | Ph. Eur., JP, NF |
| Silica, Colloidal Anhydrous | 0.300 | 0.300 | 0.300 | 0.300 | Glidant | Ph. Eur., JP, USP-NF |
| Magnesium Stearate | 0.750 | 0.750 | 0.750 | 0.750 | Lubricant | Ph. Eur., JP, NF |
| Total per Tablet | 150.0 | 150.0 | 150.0 | 150.0 | — | — |

[1]If necessary, the amount of drug substance may be adjusted to take into account the potency of the drug substance. The total amount of filler will be adjusted accordingly to compensate.

Figure 2:
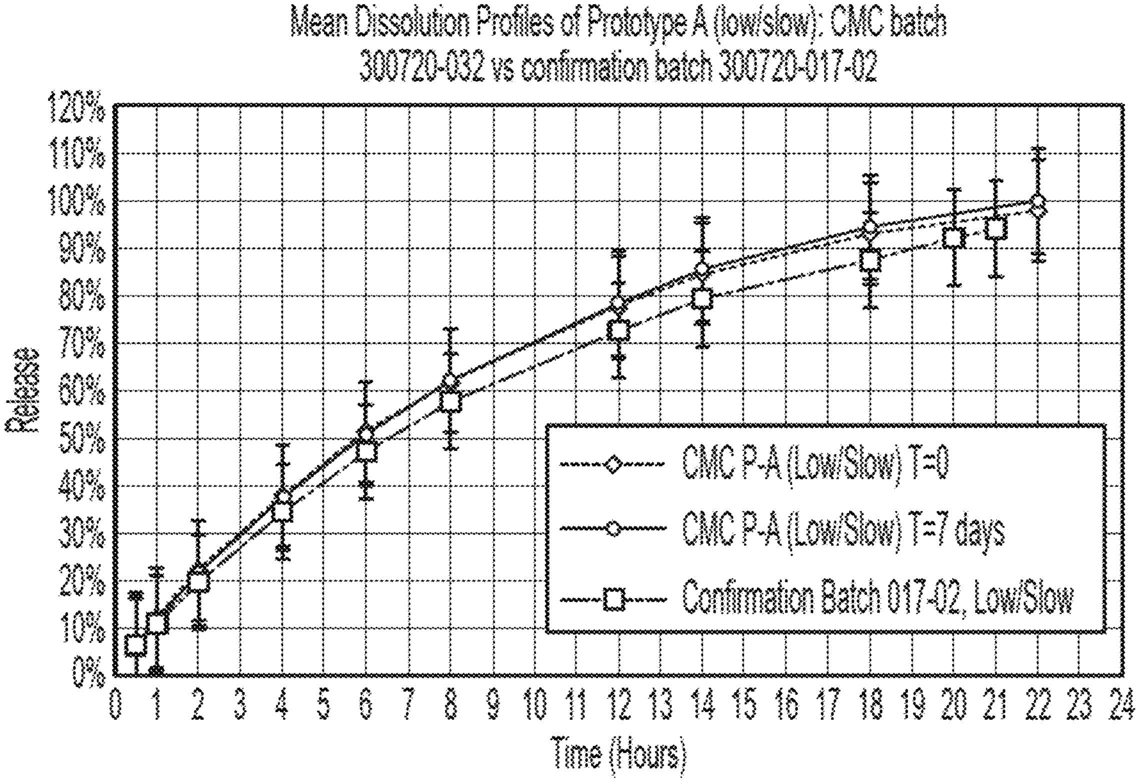
FIG. 2 depicts a mean dissolution profile of a pharmaceutical formulation, prototype A, under single stage dissolution (pH 7.2 phosphate buffer, USP II, 75 rpm (+infinity spin)). Prototype A (batch no. 300720-032, n=6) T=0 days and T=7 days vs. reference batch (batch no. 300720-017-02, n=3).

Prototype A releases approximately 50% minoxidil or a pharmaceutically acceptable salt thereof by about 6 hours in a single stage dissolution assay (FIG. 2; pH 7.2 phosphate buffer, USP II, 75 rpm (+infinity spin)). Prototype A is characterized by a low/slow dissolution profile. Batches of prototype A tested at day 0 and day 7 demonstrate similar dissolution profiles.

Figure 3:
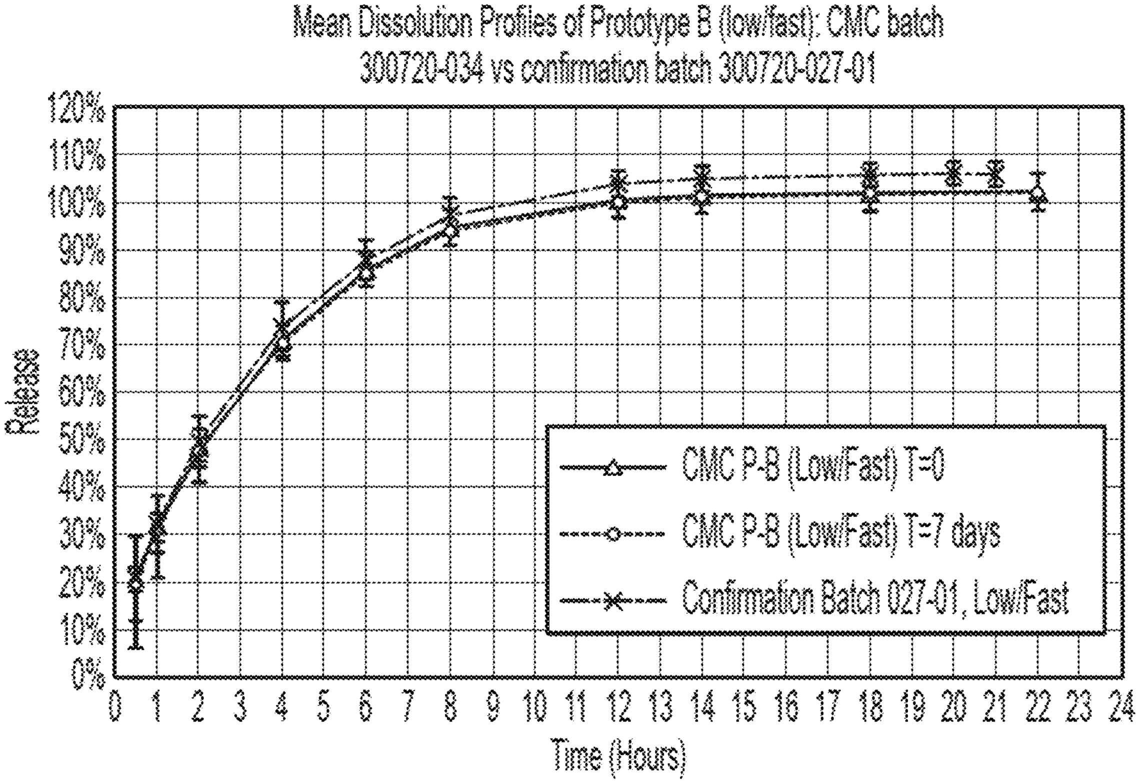
FIG. 3 depicts a mean dissolution profile of a pharmaceutical formulation, prototype B, under single stage dissolution (pH 7.2 phosphate buffer, USP II, 75 rpm (+infinity spin). Prototype B (batch no. 300720-034, n=6) T=0 days and T=7 days vs. reference batch (batch no. 300720-027-01, n=3).

Prototype B releases approximately 50% minoxidil or a pharmaceutically acceptable salt thereof by about 3 hours in a single stage dissolution assay (FIG. 3; pH 7.2 phosphate buffer, USP II, 75 rpm (+infinity spin)). Prototype B is characterized by a low/fast dissolution profile. Batches of prototype B tested at day 0 and day 7 demonstrate similar dissolution profiles.

Figure 4:
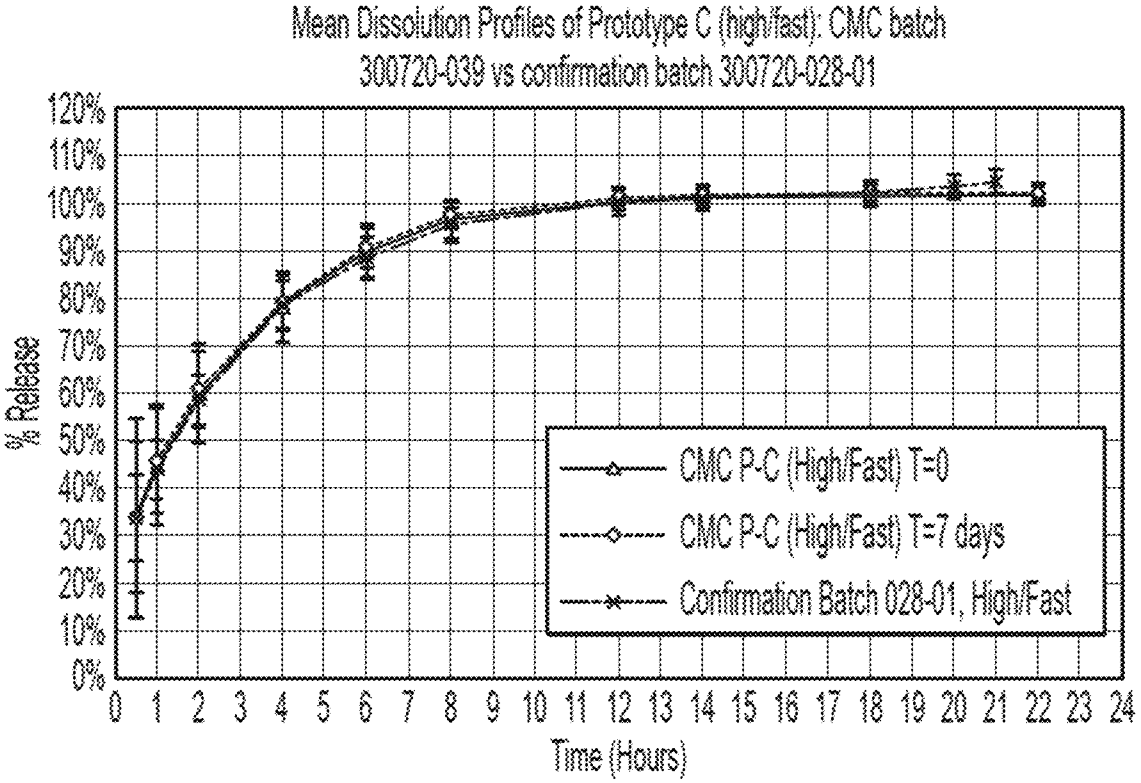
FIG. 4 depicts a mean dissolution profile of a pharmaceutical formulation, prototype C, under single stage dissolution (pH 7.2 phosphate buffer, USP II, 75 rpm (+infinity spin)). Prototype C (batch no. 300720-039, n=6) T=0 days and T=7 days vs. reference batch (batch no. 300720-028-01, n=3).

Prototype C releases approximately 50% minoxidil or a pharmaceutically acceptable salt thereof by about 1.5 hours in a single stage dissolution assay (FIG. 4; pH 7.2 phosphate buffer, USP II, 75 rpm (+infinity spin)). Prototype C is

TABLE 9

Dissolution of Modified Release Formulations of Minoxidil or a pharmaceutically acceptable salt thereof

| Time (h) | 030448-001 (10 mg) n = 2 | 030448-008 (10 mg) n = 6 | 030448-006 (2.5 mg) n = 6 |
|---|---|---|---|
| 0 | 0 | 0 | 0 |
| 2 | 25 | 23 | 32 |
| 4 | 40 | 37 | 51 |
| 6 | 52 | 48 | 64 |
| 8 | 62 | 58 | 75 |
| 10 | 70 | 67 | 82 |
| 12 | 77 | 74 | 88 |
| 14 | 83 | 80 | 93 |
| 16 | 88 | 86 | 96 |
| 18 | 92 | 90 | 98 |
| 20 | 95 | 94 | 100 |

TABLE 9-continued

| Dissolution of Modified Release Formulations of Minoxidil or a pharmaceutically acceptable salt thereof | | | |
|---|---|---|---|
| Time (h) | 030448-001 (10 mg) n = 2 | 030448-008 (10 mg) n = 6 | 030448-006 (2.5 mg) n = 6 |
| 24 | 99 | 100 | 103 |
| % RSD | 0.1-6.7 | 1.5-3.7 | 1.7-4.2 |

Figure 7:
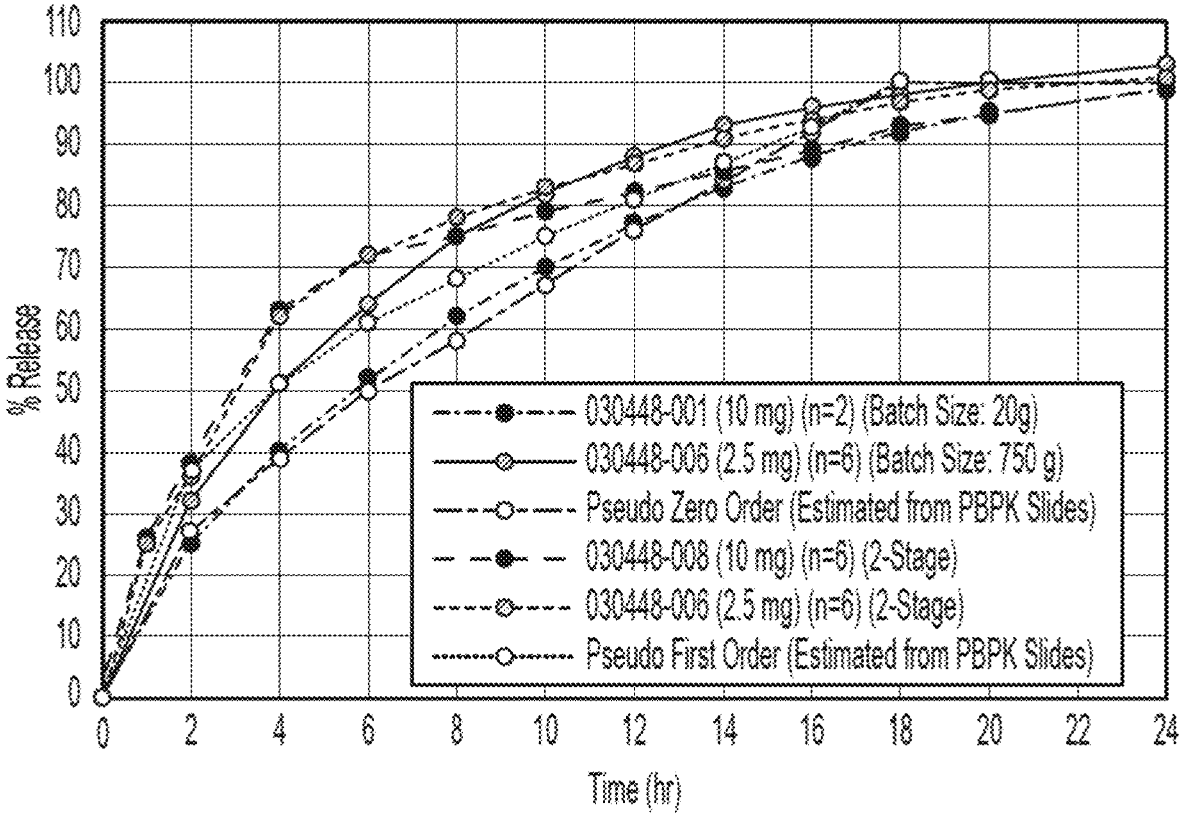
FIG. 7 depicts a two-stage dissolution of prototype batches comprising 10 mg minoxidil and 2.5 mg minoxidil.

2-stage dissolution assays were performed on 10 mg and 2.5 mg modified release formulations of minoxidil or a pharmaceutically acceptable salt thereof. The 2-stage dissolution uses a 0.1 N HCl solution (750 mL) for hours 0-2 and a neutralized solution for hours 2-24 (pH 6.8 formed by adding 250 mL of a concentrated phosphate buffer into the 750 mL acid). 2-stage dissolution increased significantly compared to 1-stage dissolution (+10% to 15%; FIG. 7). A 2-stage dissolution results in more of a first-order release profile with a large burst due to the acid-stage (Table 10 and FIG. 7). Minoxidil or a pharmaceutically acceptable salt thereof likely has pH sensitive solubility, with a high solubility in acid leading to rapid dissolution during the early hours.

TABLE 10

| 2-Stage Dissolution of Formulations of Modified Release Minoxidil or a pharmaceutically acceptable salt thereof | | | | |
|---|---|---|---|---|
| | 030448-008 (10 mg) | | 030448-006 (2.5 mg) | |
| Time (h) | pH 6.8 | 2-stage | pH 6.8 | 2-stage |
| 0 | 0 | 0 | 0 | 0 |
| 2 | 23 | 38 | 32 | 36 |
| 4 | 37 | 63 | 51 | 62 |
| 6 | 48 | 72 | 64 | 72 |
| 8 | 58 | 75 | 75 | 78 |
| 10 | 67 | 79 | 82 | 83 |
| 12 | 74 | 82 | 88 | 87 |
| 14 | 80 | 86 | 93 | 91 |
| 16 | 86 | 89 | 96 | 97 |
| 18 | 90 | 93 | 98 | 97 |
| 20 | 94 | 95 | 100 | 99 |
| 24 | 100 | 99 | 103 | 101 |

Minoxidil or a pharmaceutically acceptable salt thereof demonstrates pH-dependent solubility (Table 11). Solubility at pH 3.6 and below was theoretically determined from data from European Patent No. EP1695708, which is incorporated herein in its entirety (indicated with *).

TABLE 11

| Minoxidil or a pharmaceutically acceptable salt thereof Solubility | |
|---|---|
| pH | Solubility (mg/mL) |
| 6.0 | 2.5 |
| 5.0 | 4.1 |
| 4.6 | 11.3 |
| 3.6* | 22.0 |
| 3.0* | 87.6 |

TABLE 11-continued

| Minoxidil or a pharmaceutically acceptable salt thereof Solubility | |
|---|---|
| pH | Solubility (mg/mL) |
| 2.6* | 220.0 |
| 2.0* | 876.0 |

What is claimed is:

1. A method of improving hair growth, comprising orally administering a dosage form once daily or twice daily to a human being who has experienced hair loss, wherein the dosage form comprises about 8.5 mg of minoxidil or a molar equivalent amount of a pharmaceutically acceptable salt thereof and a release modifier, wherein the dosage form comprising the release modifier provides $C_{max}$ of minoxidil or a salt thereof that limits a likelihood and severity of a cardiovascular effect associated with a dosage form containing an immediate release formulation of 8.5 mg of minoxidil, wherein the human being has a cardiac condition.

2. The method of claim 1, wherein the dosage form is administered once daily.

3. The method of claim 1, wherein the dosage form is administered twice daily.

4. The method of claim 1, wherein the release modifier comprises a hydroxypropyl methylcellulose.

5. The method of claim 1, wherein a blood level of minoxidil or a salt thereof of about 1 ng/ml to about 20 ng/ml is maintained for at least about 8 hours.

6. The method of claim 1, wherein orally administering the dosage form provides a Cmax that is free of unacceptable cardiac effects.

7. The method of claim 1, wherein orally administering the dosage form provides an AUC that is less than the AUC that would result from orally administering 8.5 mg of minoxidil in an immediate release formulation.

8. The method of claim 1, wherein the cardiac condition comprises heart disease.

9. The method of claim 1, wherein the cardiac condition comprises hypotension.

10. The method of claim 1, wherein the cardiac condition comprises orthostatic hypotension.

11. The method of claim 1, wherein the cardiac condition comprises chronic congestive heart failure.

12. The method of claim 1, wherein the cardiac condition comprises cardiomyopathy.

13. The method of claim 1, wherein the cardiac condition comprises tachyarrhythmia.

14. The method of claim 1, wherein the cardiac condition comprises atrial fibrillation.

15. The method of claim 1, wherein the cardiac condition comprises premature ventricular contractions.

16. The method of claim 1, wherein the cardiac condition comprises supraventricular tachycardia.

17. The method of claim 1, wherein the cardiac condition comprises ventricular fibrillation.

18. The method of claim 1, wherein the cardiac condition comprises preexisting pulmonary hypertension.

19. The method of claim 1, wherein the cardiac condition comprises chronic congestive heart failure not secondary to hypertension.

* * * * *